US012736544B2

(12) United States Patent
Landi et al.

(10) Patent No.: US 12,736,544 B2
(45) Date of Patent: Sep. 15, 2026

(54) TREATMENT OF AUTOIMMUNE LIVER DISEASE

(71) Applicants: THE GOVERNORS OF THE UNIVERSITY OF ALBERTA, Edmonton (CA); Ferrucio Bonino, Pisa (IT); Maurizia Rossana Brunetto, Pisa (IT)

(72) Inventors: Abdolamir Landi, Edmonton (CA); Michael Houghton, Danville, CA (US); D. Lorne J. Tyrrell, Edmonton (CA); Ferrucio Bonino, Pisa (IT); Maurizia Rossana Brunetto, Pisa (IT); Aldo Montano-Loza, Edmonton (CA); Ana Clementin, Edmonton (CA)

(73) Assignee: THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 1381 days.

(21) Appl. No.: 17/601,595

(22) PCT Filed: Apr. 17, 2019

(86) PCT No.: PCT/US2019/027975
§ 371 (c)(1),
(2) Date: Oct. 5, 2021

(87) PCT Pub. No.: WO2020/214166
PCT Pub. Date: Oct. 22, 2020

(65) Prior Publication Data

US 2022/0196674 A1 Jun. 23, 2022

(51) Int. Cl.
*G01N 33/68* (2006.01)

(52) U.S. Cl.
CPC ..... *G01N 33/6863* (2013.01); *G01N 33/6857* (2013.01); *G01N 2333/521* (2013.01); *G01N 2800/085* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 2003/0109420 | A1* | 6/2003 | Valkirs | G01N 33/53 435/7.1 |
| 2010/0285020 | A1* | 11/2010 | Aifantis | G01N 33/57426 514/249 |
| 2012/0213799 | A1 | 8/2012 | Nishimura et al. | |
| 2016/0200807 | A1* | 7/2016 | Ruike | A61P 7/00 424/139.1 |
| 2018/0011110 | A1 | 1/2018 | Landi et al. | |

FOREIGN PATENT DOCUMENTS

| | | | | | |
|---|---|---|---|---|---|
| CA | 2859755 | A1 * | 6/2013 | A61K 38/08 |
| EP | 1674454 | A1 * | 6/2006 | A61K 31/519 |
| JP | 2008278889 | A * | 11/2008 | C07K 16/24 |
| WO | WO-2009033743 | A1 * | 3/2009 | C07K 16/18 |
| WO | WO-2011052799 | A1 * | 5/2011 | A61K 39/395 |
| WO | WO-2013165835 | A1 * | 11/2013 | A61F 9/00781 |
| WO | WO-2014151834 | A2 * | 9/2014 | A61K 39/0005 |
| WO | WO-2016004389 | A2 * | 1/2016 | A61K 39/395 |
| WO | WO-2017087318 | A1 * | 5/2017 | A61K 31/506 |

OTHER PUBLICATIONS

Aucott et al. Clinical and Vaccine Immunology Sep. 2016 vol. 23 No. 9 t http://dx.doi.org/10.1128 /CVI.00071-16. (Year: 2016).*
Hsueh et al. Journal of Autoimmunity vol. 66, Jan. 2016, pp. 89-97 Available online Nov. 1, 2015, Version of Record Jan. 8, 2016 https://doi.org/10.1016/j.jaut.2015.10.005 (Year: 2016).*
Heneghan et al. HEPATOLOGY, Jan. 2002 DOI: 10.1053/jhep.2002.30991 (Year: 2002).*
Furuta et al. J Gastroenterol 2008; 43:866-874 DOI 10.1007/s00535-008-2237-y (Year: 2008).*
Landi et al. Cytokine 78 (2016) 27-36 http://dx.doi.org/10.1016/j.cyto.2015.11.018 (Year: 2016).*
CZAJA (2014) "Review Article: chemokines as orchestrators of autoimmune hepatitis and potential therapeutic targets", Aliment Pharmacol Ther, 40:261-279.
CZAJA (2008) "Safety issues in the management of autoimmune hepatitis". Expert Opinion on Drug Safety, 7(3):319-333.
Li et al., (2013) "Investigate circulating levels of chemokines and evaluate the correlation between these chemokines and liver function indicators in autoimmune hepatitis", Zhonghua Gan Zang Bing Za Zhi, 4:299-303, Original in Chinese. English-Abstract Provided.
Landi et al., (2014) "Differential Serum Levels of Eosinophilic Eotaxins in Primary Sclerosing Cholangitis, Primary Biliary, Cirrhosis, and Autoimmune Hepatitis.", J Interferon Cytokine Res., 34(3):204-214.
Oo et al., (2010) "The role of chemokines in the recruitment of lymphocytes to the liver.", Digestive Disease, 28(1):31-44.

* cited by examiner

*Primary Examiner* — Gregory S Emch
*Assistant Examiner* — Fernando Ivich
(74) *Attorney, Agent, or Firm* — Shweta Chandra; Bozicevic, Field & Francis LLP

(57) ABSTRACT

The present disclosure provides methods and compositions that find use in identifying presence of an advanced stage autoimmune liver disease (ALD) is a subject diagnosed as having ALD. Also provided here are methods and compositions that find use in monitoring effectiveness of treatment of an ALD patient receiving a treatment for the ALD. Also provided here are methods and compositions that find use in identifying subjects suffering from a relapse of ALD. The methods and compositions of the present disclosure also find use in facilitating treatment decisions for a subject having ALD. Also provided herein are methods for treating ALD.

11 Claims, 26 Drawing Sheets

| Spearman r | |
|---|---|
| r | 0.4922 |
| 95% confidence interval | 0.2534 to 0.6744 |

| P value | |
|---|---|
| P (two-tailed) | 0.0001 |
| P value summary | *** |

| Spearman r | |
|---|---|
| r | 0.5165 |
| 95% confidence interval | 0.1404 to 0.7623 |

| P value | |
|---|---|
| P (two-tailed) | 0.0082 |
| P value summary | ** |

Table 1: clinic-pathologic features of autoimmune liver diseases

| | *AIH* | *PBC* | *PSC* |
|---|---|---|---|
| Female: male | 4:01 | 9:01 | 1:02 |
| Predominant liver test elevation | AST, ALT | Alk phos, g-GT | Alk phos, g-GT |
| Serum Ig elevation | IgG | IgM | IgG, IgM |
| Autoantibodies | ANA, ASMA, LKM1, SLA/P, pANCA | AMA, AMA-M2, gp210 | p-ANCA |
| HLA association | A3, B8, DR3, DR4 | DR8 (weak association) | DR52 |
| Histology | Interface and lobular hepatitis; prominent plasma cells | Florid bile duct lesion | Fibrosis and obliteration of large bile ducts; ductopenia |
| Diagnosis | AIH score for diagnosis of definite AIH | AMA, cholestatic serum enzyme pattern, Compatible histology | Biliary strictures and dilatation on Cholangiography; Cholestatic serum enzyme pattern, IBD, p-ANCA |
| First-line medical Therapy | Immunosuppression (Corticosteroids+ Azathioprine) | Urso-deoxycholic acid (UDCA) | No proven medical therapy |

FIG. 7

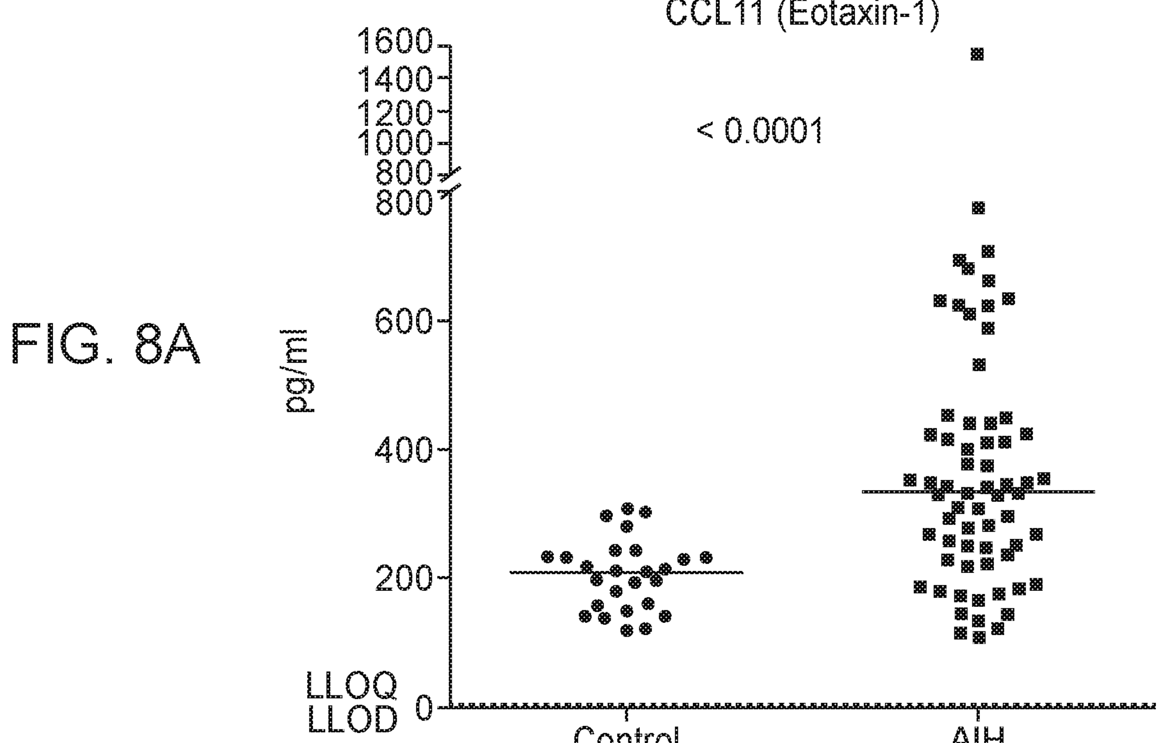
CCL11 (Eotaxin-1)
FIG. 8A
pg/ml
< 0.0001
1600
1400
1200
1000
800
800
600
400
200
0
LLOQ
LLOD
Control
AIH
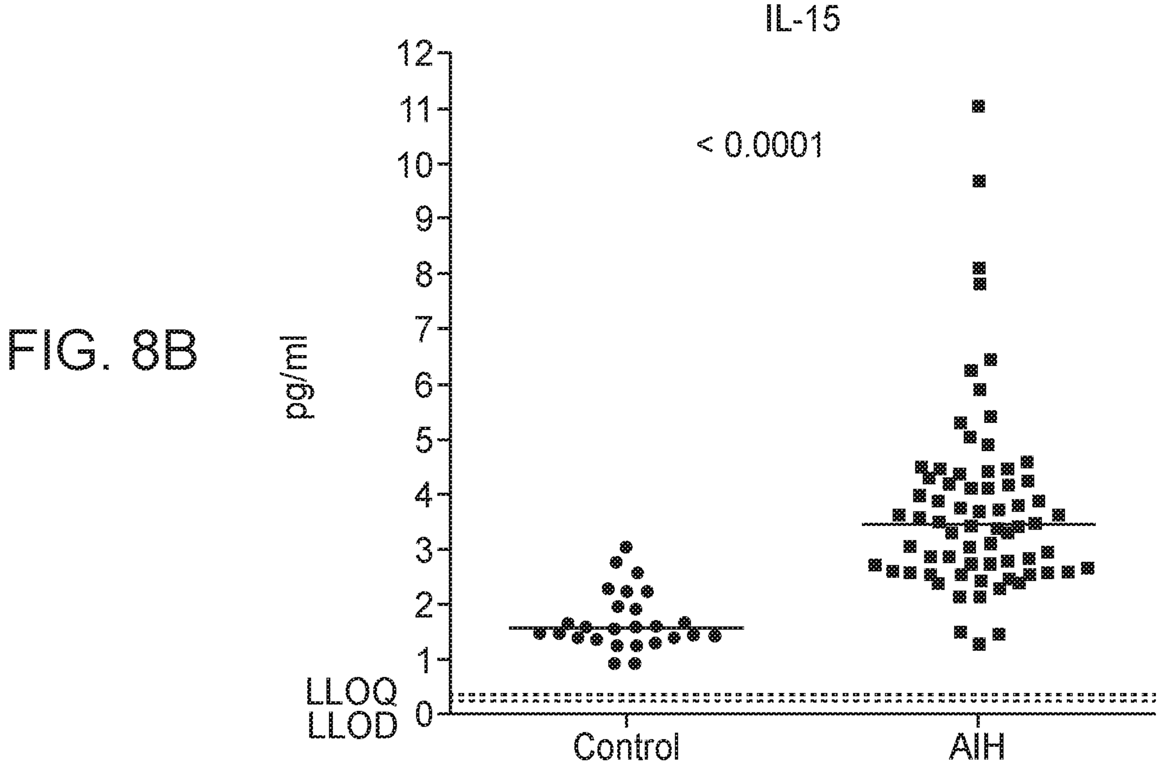
IL-15
FIG. 8B
pg/ml
< 0.0001
12
11
10
9
8
7
6
5
4
3
2
1
0
LLOQ
LLOD
Control
AIH

| Spearman r | |
|---|---|
| r | -0.007097 |
| 95% confidence interval | -0.4114 to 0.3996 |

| P value | |
|---|---|
| P (two-tailed) | 0.9731 |
| P value summary | ns |

IL-7

15
10
5
0
pg/ml
0 1 2 3 4 5
Fibrosis Stage (F1-F4)

| Spearman r | |
|---|---|
| r | -0.2293 |
| 95% confidence interval | -0.5808 to 0.1943 |

| P value | |
|---|---|
| P (two-tailed) | 0.2703 |
| P value summary | ns |

| Spearman r | |
| --- | --- |
| r | -0.1293 |
| 95% confidence interval | -0.5082 to 0.2915 |

| P value | |
| --- | --- |
| P (two-tailed) | 0.5378 |
| P value summary | ns |

| Spearman r | |
| --- | --- |
| r | -0.3206 |
| 95% confidence interval | -0.6425 to 0.09764 |

| P value | |
| --- | --- |
| P (two-tailed) | 0.1182 |
| P value summary | ns |

| Spearman r | |
|---|---|
| r | 0.1945 |
| 95% confidence interval | -0.08272 to 0.4438 |

| P value | |
|---|---|
| P (two-tailed) | 0.1548 |
| P value summary | ns |

| Spearman r | |
|---|---|
| r | -0.1732 |
| 95% confidence interval | -0.4259 to 0.1045 |

| P value | |
|---|---|
| P (two-tailed) | 0.2059 |
| P value summary | ns |

| Spearman r | |
|---|---|
| r | -0.1756 |
| 95% confidence interval | -0.4279 to 0.1022 |

| P value | |
|---|---|
| P (two-tailed) | 0.1998 |
| P value summary | ns |

VEGF-A pg/ml 800
600
400
200
0
0 1 2 3 4 5

Fibrosis Stage (F1-F4)

| Spearman r | |
|---|---|
| r | -0.1360 |
| 95% confidence interval | -0.3942 to 0.1421 |

| P value | |
|---|---|
| P (two-tailed) | 0.3221 |
| P value summary | ns |

TREATMENT OF AUTOIMMUNE LIVER DISEASE

INTRODUCTION

Autoimmune Liver Diseases (ALDs) are subdivided in three well-defined clinic-pathologic entities autoimmune hepatitis (AIH), primary biliary cholangitis (PBC) and primary sclerosing cholangitis (PSC). Although these diseases are considered autoimmune in nature, their etiology and possible environmental triggers remain obscure.

The onset of all three diseases is presented with non-specific symptoms for liver diseases such as fatigue, abdominal pain, nausea, and/or pruritus along with fluctuating levels of liver enzymes that may confirm the presence of a liver disorder only at later stages of the disease with fibrosis and cirrhosis.

The pathology of AIH starts with damage to hepatocytes resulting in interface hepatitis and piecemeal necrosis along with infiltration of leukocytes eventually followed by fibrosis and cirrhosis. In PBC and PSC, the inflammation usually starts around or close to the biliary system resulting in cholestatic disease leading to fibrosis and cirrhosis. Their diagnosis is based upon a constellation of clinical, serologic, and pathognomonic liver pathology findings (Washington, M. K., Mod Pathol, 2007.20 Suppl 1: p. S15-30), including a chronic hepatitis pattern of injury with prominent plasma cells in AIH, destruction of small intrahepatic bile ducts in PBC, and periductal fibrosis and inflammation involving larger bile ducts with variable small duct damage in PSC (see Table 1, adapted from Washington, M. K., supra and Beuers, U., J Hepatol, 2005. 42 Suppl(1): p. S93-9).

Current methodologies available for diagnosing ALD severity are either unreliable or invasive. Further, assays for monitoring efficacy of treatment of ALD and/or diagnosing remission or relapse require improvement. The present disclosure provides methods and compositions for diagnosing ALD, diagnosing ALD severity and for monitoring efficacy of treatment of ALD and/or diagnosing remission or relapse. Also provided herein are methods for treating ALD.

SUMMARY

The present disclosure is based in the finding that serum levels of cytokines such as fractalkine (CX3CL1), MIP-3β (CCL19), MIG (CXCL9), and Eotaxin3 (CCL26) are correlated to ALD and hence are useful for diagnosis of ALD as well as treatment of ALD. These cytokines can be assayed in addition to or in lieu of current diagnostic methods to improve ALD diagnosis. In certain aspects, the assays provided herein can be used for avoidance of surgeries such as liver biopsy currently used to diagnose ALD.

The present disclosure provides methods and compositions that find use in identifying a subject as having ALD. In certain aspects, the method may include assaying in a body fluid sample of the subject a level of CX3CL1, where a level of CX3CL1 greater than a threshold CX3CL1 level indicates that the subject has ALD. In certain aspects, the method may include assaying in a body fluid sample of the subject a level of CCL19, where a level of CCL19 greater than a threshold CCL19 level indicates that the subject has ALD. In certain aspects, the method may include assaying in a body fluid sample of the subject a level of CXCL9, where a level of CXCL9 greater than a threshold CXCL9 level indicates that the subject has ALD. In certain cases, the ALD is AIH.

In certain aspects, the present disclosure provides a method of assaying a body fluid sample of a subject suspected of having AIH, wherein the method comprises measuring a level of at least one cytokine selected from CX3CL1, CCL19, CXCL9, and Eotaxin-3. In certain aspects, the method comprises measuring a level of at least two cytokines selected from CX3CL1, CCL19, CXCL9, and Eotaxin-3. In certain aspects, the method comprises measuring a level of at least three cytokines selected from CX3CL1, CCL19, CXCL9, and Eotaxin-3. In certain aspects, the method comprises measuring a level of CX3CL1, CCL19, CXCL9, and Eotaxin-3 in a body fluid sample of a subject suspected of having AIH. The body fluid sample may be blood, serum, or plasma.

The present disclosure provides methods and compositions that find use in identifying presence of an advanced stage autoimmune liver disease (ALD) is a subject diagnosed as having ALD. Also provided are methods and compositions that find use in monitoring response of an ALD patient to an ALD treatment. Also provided are methods and compositions that find use in identifying subjects suffering from a relapse of ALD. These methods and compositions facilitate treatment decisions for a subject having ALD.

A method for identifying a subject as having an advanced stage autoimmune liver disease (ALD) is disclosed. In certain aspects, the method may include assaying in a body fluid sample of the subject a level of CX3CL1, where a level of CX3CL1 greater than a threshold CX3CL1 level indicates that the subject has an advanced stage ALD. In certain aspects, the subject may have been diagnosed as having autoimmune liver disease (ALD). In certain aspects, the ALD may be autoimmune hepatitis (AIH), primary biliary cholangitis (PBC) or primary sclerosing cholangitis (PSC).

In certain aspects, the advanced stage autoimmune liver disease may be liver fibrosis, liver cirrhosis, or decompensated liver cirrhosis. In certain aspects, a level of CX3CL1 greater than a threshold CX3CL1 level may indicate that the subject has liver fibrosis. In certain aspects, a level of CX3CL1 greater than a threshold CX3CL1 level may indicate that the subject has liver cirrhosis. In certain aspects, a level of CX3CL1 greater than a threshold CX3CL1 level may indicate that the subject has decompensated liver cirrhosis.

The subject may be diagnosed as having primary biliary cholangitis (PBC) or autoimmune hepatitis (AIH). Additional aspects of the disclosed method include treating the subject having an advanced stage ALD, e.g., PBC or AIH, based on the severity of the disease.

The present disclosure also provides a method for monitoring response to treatment for an autoimmune liver disease (ALD) in a subject receiving the treatment. In certain embodiments, the method may include assaying in a body fluid sample of the subject a level of CX3CL1, where a level of CX3CL1 lower than a threshold level of CX3CL1, indicates that the subject is responding positively to the treatment. In other embodiments, the method may include assaying in a body fluid sample of the subject a level of CCL19, wherein a level of CCL lower than a threshold level of CCL19, indicates that the subject is responding positively to the treatment. In yet another embodiment, the method may include assaying in a body fluid sample of the subject a level of CX3CL1 and a level of CCL19, wherein a level of CX3CL1 lower than a threshold level of CX3CL1 and/or a level of CCL19 lower than a threshold level of CCL19, indicates that the subject is responding positively to the treatment. In further embodiments, the method may further include assaying a level of CXCL9, in addition to assaying a level of CX3CL1 and/or CCL19, in a body fluid sample of the subject, wherein a level of CXCL9 lower than the threshold level of CXCL9, indicates that the subject is responding positively to the treatment. In further embodiments, the method may further include assaying a level of Eotaxin-3, in addition to assaying a level of CX3CL1 and/or CCL19, in a body fluid sample of the subject, wherein a level of Eotaxin-3 lower than the threshold level of Eotaxin-3, indicates that the subject is responding positively to the treatment.

The autoimmune liver disease may be autoimmune hepatitis (AIH), primary biliary cholangitis (PBC) or primary sclerosing cholangitis (PSC). The treatment may be an immunosuppressive therapy and/or administering one or more of ursodeoxycholic acid, obeticholic acid, fenofibrate, bezafibrate, or a derivative thereof.

In certain aspects of the method for monitoring effectiveness of treatment of an ALD, when the level of CX3CL1 is higher than the threshold level of CX3CL1, when the level of CCL19 is higher than the threshold level of CCL19, and/or when the level of CXCL9 is higher than the threshold level of CXCL9, the method may include altering the treatment, wherein altering the treatment comprises changing the treatment regimen or changing the active agent administered to the subject.

Certain embodiments of the method may include changing the treatment regimen by increasing dose and/or dosage of the active agent administered to the subject.

In certain aspects of the method for monitoring effectiveness of treatment of an ALD, when the level of CX3CL1 is lower than the threshold level of CX3CL1, when the level of CCL19 is lower than the threshold level of CCL19, when the level of CXCL9 is lower than the threshold level of CXCL9, and/or when the level of Eotaxin-3 is lower than the threshold level of Eotaxin-3, the method may include tapering the dose and/or dosage of the treatment or terminating the treatment.

Certain aspects of the methods include monitoring a subject who has been treated for an ALD and whose treatment has been terminated. Such methods may include assaying in a body fluid sample of the subject, a level of one or more of CX3CL1, CCL19 and CXCL9, wherein a level of CX3CL1 higher than a threshold level of CX3CL1, a level of CCL19 higher than a threshold level of CCL19, and/or a level of CXCL9 higher than a threshold level of CXCL9, indicates that the subject has a relapse of the ALD. The ALD may be autoimmune hepatitis (AIH), primary biliary cholangitis (PBC) or primary sclerosing cholangitis (PSC).

The present method may include treating a subject diagnosed as having a relapse of ALD. The treatment may include an immunosuppressive therapy and/or administering one or more of ursodeoxycholic acid, obeticholic acid, fenofibrate, bezafibrate, or a derivative thereof to the subject.

In another aspect, a method for monitoring progression of ALD in a subject is disclosed. The method may include measuring at a first time point in a body fluid sample of the subject a level of CX3CL1 to obtain a first level of CX3CL1; measuring at a second time point in a body fluid sample of the subject a level of CX3CL1 to obtain a second level of CX3CL1, wherein the second time point is after the first time point; wherein an increased second level of CX3CL1 compared to the first level of CX3CL1 is indicative of increased severity of ALD, wherein a lack of change between first and second levels of CX3CL1 is indicative of lack of change in severity of ALD, and wherein a decreased second level of CX3CL1 compared to the first level of CX3CL1 is indicative of improvement in ALD. In another aspect, the method may include measuring in a body fluid sample of the subject a level of CX3CL1 at multiple points of time over a period, wherein a trend of increased level of CX3CL1 is indicative of increased severity of ALD.

In another aspect, a method for monitoring responsiveness of a subject to a treatment for an autoimmune liver disease (ALD) is provided. The method may include measuring at a first time point in a body fluid sample of the subject a level of CX3CL1 to obtain a first level of CX3CL1; measuring at a second time point in a body fluid sample of a subject level of CX3CL1 to obtain a second level of CX3CL1, wherein the second time point is after the first time point; wherein a decreased second level of CX3CL1 compared to the first level of CX3CL1 indicates a positive response to the treatment, wherein an increased second level of CX3CL1 compared to the first level of CX3CL1 is indicative of increased severity of ALD, and wherein a lack of change between first and second levels of CX3CL1 is indicative of lack of change in severity of ALD.

In another aspect, a method for monitoring responsiveness of a subject to a treatment for an ALD may include measuring at a first time point in a body fluid sample of the subject a level of CCL19 to obtain a first level of CCL19; measuring at a second time point in a body fluid sample of a subject level of CCL19 to obtain a second level of CCL19, wherein the second time point is after the first time point; wherein a decreased second level of CCL19 compared to the first level of CCL19 indicates a positive response to the treatment.

In another aspect, a method for monitoring responsiveness of a subject to a treatment for an ALD may include measuring at a first time point in a body fluid sample of the subject a level of CX3CL1 and CCL19 to obtain a first level of CX3CL1 and CCL19; measuring at a second time point in a body fluid sample of a subject level of CX3CL1 and CCL19 to obtain a second level of CX3CL1 and CCL19, wherein the second time point is after the first time point; wherein a decreased second level of CX3CL1 compared to the first level of CX3CL1 and/or wherein a decreased second level of CCL19 compared to the first level of CCL19 indicates a positive response to the treatment, wherein an increased second level of CX3CL1 compared to the first level of CX3CL1 is indicative of increased severity of ALD, and wherein a lack of change between first and second levels of CX3CL1 is indicative of lack of change in severity of ALD. The method may include measuring in a body fluid sample of the subject a level of CX3CL1 and/or CCL19 at multiple points of time over a period, wherein a trend of decreased level of CX3CL1 and/or CCL19 is indicative of positive response to the treatment. The method may additionally include measuring at the first time point in a body fluid sample of the subject a level of CXCL9 to obtain a first level of CXCL9; measuring at the second time point in a body fluid sample of the subject a level of CXCL9 to obtain a second level of CXCL9; wherein a decreased second level of CXCL9 compared to the first level of CXCL9 indicates a positive response to the treatment. In certain cases, the method comprises measuring in a body fluid sample of the subject a level of CXCL9 at multiple points of time over a period, wherein a trend of decreased level of CXCL9 is indicative of positive response to the treatment.

In certain embodiments, a method for monitoring relapse of an autoimmune liver disease (ALD) in a subject treated for the ALD may include measuring at a first time point in a body fluid sample of the subject a level of CX3CL1 to obtain a first level of CX3CL1; measuring at a second time point in a body fluid sample of the subject a level of CX3CL1 to obtain a second level of CX3CL1, wherein the second time point is after the first time point; wherein an increased second level of CX3CL1 compared to the first level of CX3CL1 indicates relapse of the ALD, and wherein a lack of change between first and second levels of CX3CL1 or a decreased second level of CX3CL1 compared to the first level of CX3CL1 is indicative of a stable disease free state.

In certain embodiments, a method for monitoring relapse of an autoimmune liver disease (ALD) in a subject treated for the ALD may include measuring at a first time point in a body fluid sample of the subject a level of CCL19 to obtain a first level of CCL19; measuring at a second time point in a body fluid sample of the subject a level of CCL19 to obtain a second level of CCL19, wherein the second time point is after the first time point; wherein an increased second level of CCL19 compared to the first level of CCL19 indicates relapse of the ALD.

In certain embodiments, a method for monitoring relapse of an autoimmune liver disease (ALD) in a subject treated for the ALD may include measuring at a first time point in a body fluid sample of the subject a level of CX3CL1 and CCL19 to obtain a first level of CX3CL1 and CCL19; measuring at a second time point in a body fluid sample of the subject a level of CX3CL1 and CCL19 to obtain a second level of CX3CL1 and CCL19, wherein the second time point is after the first time point; wherein an increased second level of CX3CL1 compared to the first level of CX3CL1 and/or an increased second level of CCL19 compared to the first level of CCL19 indicates relapse of the ALD, and wherein a lack of change between first and second levels of CX3CL1 or a decreased second level of CX3CL1 compared to the first level of CX3CL1 is indicative of a stable disease free state. In certain cases, the method includes measuring in a body fluid sample of the subject a level of CX3CL1 at multiple points of time over a period, wherein a trend of increased level of CX3CL1 is indicative of relapse of the ALD. In certain cases, the method includes measuring in a body fluid sample of the subject a level of CCL19 at multiple points of time over a period, wherein a trend of increased level of CCL19 is indicative of relapse of the ALD.

In certain cases, the method additionally includes measuring at the first time point in a body fluid sample of the subject a level of CXCL9 to obtain a first level of CXCL9; measuring at the second time point in a body fluid sample of the subject a level of CXCL9 to obtain a second level of CXCL9; wherein an increased second level of CXCL9 compared to the first level of CXCL9 indicates a relapse of the ALD. In certain aspects, the method may include measuring in a body fluid sample of the subject level of CXCL9 at multiple points of time over a period, wherein a trend of increased level of CXCL9 is indicative of relapse of the ALD.

Also provided herein are methods for treating a subject diagnosed with an autoimmune liver disease (ALD). The method may include administering to a subject an effective amount of an immunosuppressive agent; and/or one or more of ursodeoxycholic acid, obeticholic acid, fenofibrate, bezafibrate, or a derivative thereof, wherein the subject is identified as in need for treatment for an ALD based on having, in a body fluid sample, a level of CX3CL1 higher than a threshold level of CX3CL1.

In other aspects, the method of treating a subject diagnosed with an ALD may include administering to a subject an effective amount of an immunosuppressive agent; and/or one or more of ursodeoxycholic acid, obeticholic acid, fenofibrate, bezafibrate, or a derivative thereof, wherein the subject is identified as in need for treatment for an ALD based on having, in a body fluid sample, a level of CCL19 higher than a threshold level of CCL19.

In other aspects, the method of treating a subject diagnosed with an ALD may include administering to a subject an effective amount of an immunosuppressive agent; and/or one or more of ursodeoxycholic acid, obeticholic acid, fenofibrate, bezafibrate, or a derivative thereof, wherein the subject is identified as in need for treatment for an ALD based on having, in a body fluid sample, a level of CCL19 higher than a threshold level of CCL19 and a level of CX3CL1 higher than a threshold level of CX3CL1.

In certain aspects, the subject may be identified as in need for treatment for an ALD based on additionally having, in a body fluid sample, a level of CXCL9 higher than a threshold level of CXCL9. The ALD may be AIH, PBC, or PSC.

In certain aspects of the methods disclosed herein, the body fluid sample may be a blood, serum, or plasma sample. In certain aspects, assaying the level of CX3CL1 may include contacting the sample with an anti-CX3CL1 antibody; assaying the level of CXCL9 may include contacting the sample with an anti-CXCL9 antibody; assaying the level of CCL19 may include contacting the sample with an anti-CCL19 antibody.

The present disclosure provides methods of treating a subject having autoimmune hepatitis (AIH), primary sclerosing cholangitis (PSC), or primary biliary cirrhosis (PBC), the method comprising administering to the subject an effective amount of an antagonist of CCL19, CX3CL1, and/or CXCL9 activity, e.g., an antagonist of a receptor of CCL19, CX3CL1, and/or CXCL9. An antagonist of CCL19 activity may be an agent that decreases activity of CCL19 or a receptor for CCL19, e.g., CCR7. In certain aspects, an agent that decreases CCL19 activity may be an anti-CCL19 antibody. In certain aspects, an agent that decreases activity of a receptor for CCL19 may be an anti-CCR7 antibody. An antagonist of CX3CL1 activity may be an agent that decreases activity of CX3CL1 or a receptor for CX3CL1, e.g., CX3CR1. In certain aspects, an agent that decreases CX3CL1 activity may be an anti-CX3CL1 antibody. In certain aspects, an agent that decreases activity of a receptor for CX3CL1 may be an anti-CX3CR1 antibody. An antagonist of CXCL9 activity may be an agent that decreases activity of CXCL9 or a receptor for CXCL9, e.g., CXCR3. In certain aspects, an agent that decreases CXCL9 activity may be an anti-CXCL9 antibody. In certain aspects, an agent that decreases activity of a receptor for CXCL9 may be an anti-CXCR3 antibody.

Provided herein is a method for treating a subject identified as having AIH, PBC, or PSC, the method comprising administering an antagonist of CCL19 activity to the subject. In certain aspects, the subject may have a level of CCL19 that is higher than a threshold level of CCL19. In certain aspects, the antagonist of CCL19 activity comprises an anti-CCL19 antibody. In certain aspects, the antagonist of CCL19 activity antagonizes CCR7 activity and may be an anti-CCR7 antibody. In certain aspects, an antagonist CCL19 activity may be used for lowering inflammation in the liver of the subject having AIH, PBC, or PSC.

Also provided herein is a method for treating a subject identified as having AIH, PBC, or PSC, the method comprising administering an antagonist of CX3CL1 activity to the subject. In certain aspects, the subject may have a level of CX3CL1 that is higher than a threshold level of CX3CL1. In certain aspects, the antagonist of CX3CL1 activity comprises an anti-CX3CL1 antibody. In certain aspects, the antagonist of CX3CL1 activity antagonizes CX3CR1 activity and may be an anti-CX3CR1 antibody. In certain aspects, an antagonist CX3CL1 activity may be used for lowering inflammation in the liver of the subject having AIH, PBC, or PSC.

Also provided herein is a method for treating a subject identified as having AIH, PBC, or PSC, the method comprising administering an anti-CCL19 antibody and an anti-CX3CL1 antibody to the subject. In certain aspects, the subject may have a level of CCL19 that is higher than a threshold level of CCL19 and a level of CX3CL1 that is higher than a threshold level of CX3CL1. In certain aspects, the anti-CCL19 antibody and the anti-CX3CL1 may be used for lowering inflammation in the liver of the subject having AIH, PBC, or PSC.

Also provided herein is a method for treating a subject identified as having AIH, PBC, or PSC, the method comprising administering an anti-CCL19 antibody, an anti-CX3CL1 antibody, and an anti-CXCL9 antibody to the subject. In certain aspects, the subject may have a level of CCL19 that is higher than a threshold level of CCL19, a level of CX3CL1 that is higher than a threshold level of CX3CL1, and a level of CXCL9 that is higher than a threshold level of CXCL9. In certain aspects, the anti-CCL19 antibody, the anti-CX3CL1, and the anti-CXCL9 antibody may be used for lowering inflammation in the liver of the subject having AIH, PBC, or PSC.

The present disclosure provides methods of treating a subject having primary sclerosing cholangitis (PSC), the method comprising administering to the subject an effective amount of an antagonist of CCL19, e.g., an anti-CCL19 antibody or an antagonist of a receptor for CCL19, e.g., an anti-CCR7 antibody.

The treatment method disclosed herein may be combined with other treatment methods to enhance beneficial effect from the treatment. For example, the treatment methods may further include administering an antagonist of Eotaxin 3 (E3), e.g., an anti-E3 antibody or an antibody against an E3 receptor, e.g., an anti-CX3CR1 antibody and/or an anti-CCR3 antibody.

BRIEF DESCRIPTION OF THE DRAWINGS

FIG. 7. Table 1 shows clinic-pathologic features of autoimmune liver diseases, (adapted from Washington, M. K., supra and Beuers, U., supra).

FIGS. 8A-8C. CCL11 (Eotaxin-1) (FIG. 8A), IL-15 (FIG. 8B), and IL-16 (FIG. 8C) plasma levels are increased in AIH patients compared to healthy control group.

DETAILED DESCRIPTION OF EMBODIMENTS

Figure 1A:
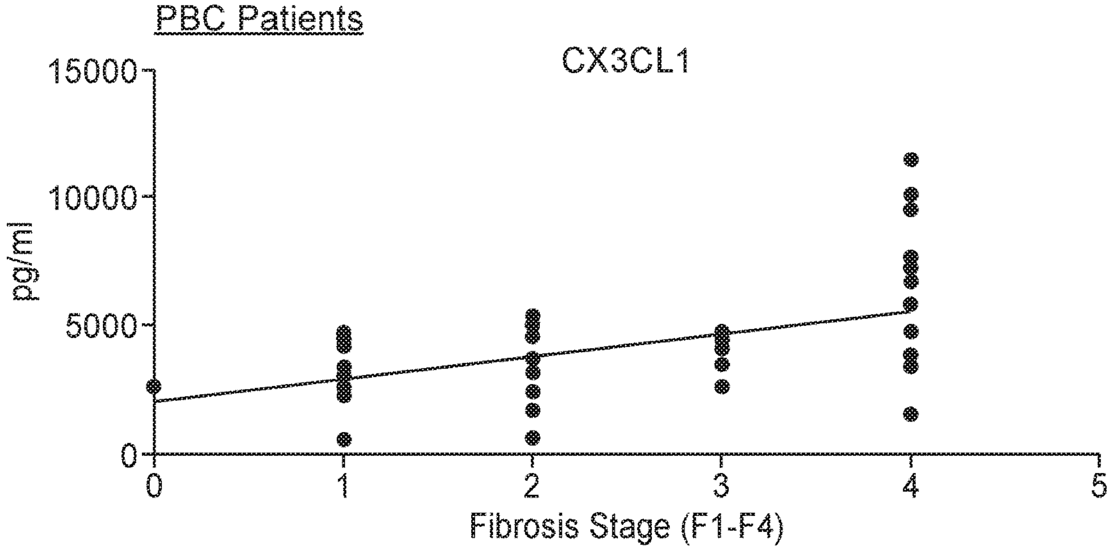
FIG. 1A. CX3CL1 (fractalkine) levels have a highly significant moderate correlation with fibrosis stage in PBC.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms “a”, “and”, and “the” include plural referents unless the context clearly dictates otherwise. Thus, for example, reference to “a sample” includes a plurality of such samples and reference to “the polypeptide” includes reference to one or more polypeptides and equivalents thereof known to those skilled in the art, and so forth.

The publications discussed herein are provided solely for their disclosure prior to the priority date of the present application. Nothing herein is to be construed as an admission that the present invention is not entitled to antedate such publication by virtue of prior invention. Further, the dates of publication provided may be different from the actual publication dates which may need to be independently confirmed.

Examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Definitions

“Autoimmune liver disease” or “ALD” refers spectrum of chronic inflammatory liver diseases caused by the body losing its tolerance for liver tissue and mounting an autoimmune response against cells in the liver. ALD encompasses autoimmune hepatitis (AIH), primary biliary cholangitis (PBC) and primary sclerosing cholangitis (PSC).

“Autoimmune hepatitis” or “AIH” refers to a chronic inflammatory liver disease in which the body’s immune system attacks cells of the liver. This autoimmune response results in inflammation of the liver, which can lead to further complications such as cirrhosis. The pathology of AIH, which is more common in women than men, begins with damage to hepatocytes resulting in interface hepatitis and piecemeal necrosis accompanied by leukocyte infiltration eventually followed by fibrosis and cirrhosis. AIH can be associated with anti-nuclear antibodies (ANA), anti-smooth muscle antibodies (SMA), antibodies to liver/kidney microsome type 1 (anti-LKM1) antibodies to soluble liver/pancreas antigen (anti-SLA/LP), perinuclear anti-neutrophil cytoplasmic antibodies (pANCA), antibodies to liver-specific cytosol antigen type 1 (anti-LC1), and anti-actin antibodies (Manns, et al. Hepatology, 2010. 51(6): p. 2193-213; Czaja, eta 1. Gastroenterology, 2010. 139(1): p. 58-72 e4). Since these autoantibodies are not specific for AIH and may be detected in patients with PBC, PSC, viral hepatitis, drug-induced hepatitis, and alcoholic hepatitis, the International Autoimmune Hepatitis Group has suggested a diagnostic algorithm, which is provided below as a coded panel, for diagnosis of AIH. An algorithm to facilitate a diagnosis definite, probable, or lack of AIH, based on four parameters including the levels of different autoantibodies, the level of IgG, liver histology, and absence of a known viral infection has been described (see, Lohse, et al. J. Hepatol. 2011. 55(1): p. 171-82) and is summarized below:

| | | Points |
|---|---|---|
| Autoantibodies | ANA or SMA or LKM > 1:40 | 1 |
| | ANA or SMA or LKM > 1:80 | 2 |
| | SLA/LP Positive (>20 units) | |
| IgG (or gamma-globulins) | Upper normal limit | 1 |
| | >1.10 times normal limit | 2 |
| Liver histology* | Compatible with AIH | 1 |
| | Typical for AIH | 2 |
| Absence of viral hepatitis | Yes | 2 |
| | No | 0 |

Definite autoimmune hepatitis (AIH): ≥7;
probable AIH: ≥6. ANA, antinuclear antibody;
SMA, smooth muscle antibody;
LKM, liver kidney microsomal;
SLA/LP, anti-soluble liver antigen/liver pancreas AIH may be sub-classified on the basis of the autoantibody profile that might define sub-groups with distinct pathogenesis useful for research purposes. Type 1 AIH (ANA and/or SMA positive) shows a bimodal age distribution (with peaks in adolescents and after 40 years of age): whereas, type 2 AIH (anti-LKM1 positive) prevails in young women and type 3 AIH (SLA/LP antibodies positive) is clinically indistinguishable from type I (Washington, M. K., supra). However, such a sub-classification has little application in clinical practice because treatment options are currently independent from it. As used herein AIH encompasses AIH-type 1, AIH-type 2, and AIH-type 3. However, more recently, AIH patients are sub classified into Type 1 and Type 2 and Type 3 is no longer used. Further, it is unclear whether there is enough clinical, biochemical, histological or genetic reason to subdivide AIH patients into type 1 and type 2 on the basis of autoantibody profile.

“Primary biliary cirrhosis” or “PBC” (which is also known as also called chronic nonsuppurative destructive cholangitis) refers to a chronic non-suppurative destructive granulomatous cholangitis with unknown etiology in which the pathology is more related to the medium-sized intrahepatic bile ducts rather than hepatocytes, resulting in cholestatic features of the disease with a high level of alkaline phosphatase (ALP) in serum (Kaplan et al. The New England Journal of Medicine, 2005. 353(12): p. 1261-73). Inflammation usually starts adjacent the biliary system, resulting in cholestatic disease leading to fibrosis. Although other autoantibodies (e.g., ANA) may be detected in PBC, the anti-mitochondrial antibody (AMA) against acyltransferases of the inner mitochondrial membrane has high sensitivity and specificity for PBC (Kaplan et al. supra) and is reported in 95% of PBC cases. In addition, elevated immunoglobulins, especially IgM, as well as specific histologic features such as bile duct damage, ductopenia, and granulomatous portal inflammation are indicative of a PBC diagnosis. As with AIH, PBC is more common in women and is currently considered as a liver-specific autoimmune disease occurring in genetically predisposed individuals with association to other autoimmune conditions such as Sjogren syndrome and thyroid disease. PBC is generally not reported in children. "Children" as used herein refers to individuals under 12 years old.

"Primary sclerosing cholangitis" or "PSC" refers to a chronic cholestatic condition that affects all sizes of bile ducts (Angulo, et al. Clinics in Liver Disease, 1999. 3(3): p. 529-70; Angulo, et al. Hepatology, 1999. 30(1): p. 325-32). As in PBC, the inflammation in PSC usually starts adjacent the biliary system resulting in cholestatic disease leading to fibrosis and cirrhosis. Up to about 80% of PSC cases are associated with inflammatory bowel disease, in particular ulcerative colitis. The disease can be complicated by the development of bile duct cancer in up to 15%. In addition, the incidence of pancreatic cancer and colonic cancer is increased relative to unaffected individuals. Diagnosis is usually based on the endoscopic retrograde cholangiography (ERC) and/or magnetic resonance cholangiography (MRC), which are showing the typical strictures and dilations in intra- and extra-hepatic bile ducts, along with the exclusion of other causes of the typical multifocal biliary structures and intervening dilatations. On liver biopsy, periductular fibrosis with concentric layers of fibrous tissue called onion skin fibrosis can be observed. PSC is more common in men than women.

The terms "individual," "subject," and "patient," used interchangeably herein, refer to a human.

The term "healthy individual" in the context of the methods of the present disclosure refers to an individual who is unaffected by a detectable illness, particularly a liver disease (for example, hepatitis (e.g., viral or autoimmune hepatitis or an ALD (e.g., AIH, PBC and PSC). Healthy individuals include those who have not reported any complaint, symptom or sign of any diseases at the time of visit and, optionally, for the last month; have not had any history of liver disease; are not undergoing therapy for a disease, particularly for a liver disease; have normal complete blood count (CBC) differential test, as well as normal level of serum ALT (alanine aminotransaminase) and serum GGT (γ-glutamyl transferase); are negative for biliary disease; test negative for viral hepatitis (e.g., HCV infection, HBV infection); test negative for HIV infection; and are negative for nonalcoholic steatohepatitis (NASH), alcohol-induced hepatitis, and drug-induced hepatitis.

The terms "responder" refers to a subject that shows a positive effect in response to a treatment. A responder as used herein encompasses a subject who upon receiving a treatment for an ALD, such as, AIH, PSC, and/or PBC, shows a detectable improvement in one or more symptoms of the disease being treated. Similarly, a subject that responds positively to a treatment refers to a subject who shows a detectable improvement in one or more symptoms of the disease being treated. A "non-responder" refers to a subject that does not show a positive effect in response to a treatment. A non-responder as used herein encompasses a subject who upon receiving a treatment for an ALD, such as, AIH, PSC, and/or PBC, shows no detectable improvement in one or more symptoms of the disease being treated.

The term "advanced stage autoimmune liver disease" or "advanced stage ALD" refers to ALD that progressed from an initial stage where the subject does not have overt symptoms to later stage with more severe symptoms that signifies further deterioration of the subject's liver.

In the case of PSC, an advanced stage signifying progression of the disease into a more severe form includes multiple stages where the initial stage does not have severe symptoms. PSC can be staged based on appearance and changes seen in liver tissue obtained by a biopsy. Such a histological staging of progression of severity of PSC can include stage 1 (Portal: Infiltration of the bile duct by lymphocytes with degeneration of the epithelial cells of the bile duct. These findings are not present outside the portal triads); stage 2 (Periportal: There is more widespread involvement with fibrosis, inflammation infiltration in the periportal parenchyma with piecemeal necrosis of the periportal hepatocytes. The portal triads are enlarged but there is relative absence of bile ducts (bile ductopenia)); stage 3 (Septal: There are portal-to-portal fibrous bridges with severe degeneration of the ducts and ductopenia), and stage 4 (Cirrhosis: End stage liver disease with frank cirrhosis).

In the case of PBC, an advanced stage signifying progression of the disease into a more severe form includes multiple stages where the initial stage does not have severe symptoms. PBC stages include: Portal Stage: Normal sized triads; portal inflammation, subtle bile duct damage. Granulomas—nodules filled with a variety of inflammatory cells—are often detected in this stage; Periportal Stage: Enlarged triads; periportal fibrosis and/or inflammation. Typically characterized by the finding of a proliferation of small bile ducts; Septal Stage: Active and/or passive fibrous septae; and Biliary Cirrhosis: Nodules present; garland or jigsaw pattern.

Advanced stage of an ALD can also be determined by the extent of fibrosis, such as, fibrosis denoted by fibrosis ranking. Fibrosis ranking involves liver biopsy. The methods for determining severity of ALD avoid invasive methods and instead provide alternate methods for determining presence of fibrosis stage (F1-F4; F1=least fibrosis; F4=most fibrosis).

Advanced stage of an ALD can also be determined by severity of cirrhosis in the subject, where decompensated cirrhosis indicates and advanced stage ALD while compensated cirrhosis indicated mild ALD. Patients with compensated cirrhosis do not have symptoms related to their cirrhosis, but may have asymptomatic esophageal or gastric varices. Patients with decompensated cirrhosis have symptomatic complications related to cirrhosis, including those related to hepatic insufficiency (jaundice), and those related to portal hypertension (ascites, variceal hemorrhage, or hepatic encephalopathy).

The terms "polypeptide," "peptide" and "protein", used interchangeably herein, refer to a polymeric form of amino acids of any length, which can include biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. "$NH_2$" refers to the free amino group present at the amino terminus of a polypeptide and "COOH" refers to the free carboxyl group present at the carboxyl terminus of a polypeptide in keeping with standard polypeptide nomenclature, *J. Biol. Chem.,* 243 (1969), 3552-59 is used.

In the context of a polypeptide present in a biological sample, "polypeptide" refers to a naturally-occurring polypeptide present in an individual from whom the sample is obtained.

"Conservative amino acid substitution" refers to a substitution of one amino acid residue for another sharing chemical and physical properties of the amino acid side chain (e.g., charge, size, hydrophobicity/hydrophilicity). "Conservative substitutions" are intended to include substitution within the following groups of amino acid residues: gly, ala; val, ile, leu; asp, glu; asn, gln; ser, thr; lys, arg; and phe, tyr. Guidance for such substitutions can be drawn from alignments of amino acid sequences of polypeptides.

A "biomarker" or "marker" as used herein generally refers to an organic biomolecule (e.g., a polypeptide) which is differentially present in a sample taken from a subject of one phenotypic status (e.g., having a disease) as compared with another phenotypic status (e.g., not having the disease or having a different level or severity of the disease or having a different disease). A biomarker is differentially present between different phenotypic statuses if the mean or median level of the biomarker in a first phenotypic status relative to a second phenotypic status is calculated to represent statistically significant differences. Common tests for statistical significance include, among others, t-test, ANOVA, Kruskal-Wallis, Wilcoxon, Mann-Whitney and odds ratio. Biomarkers, alone or in combination, provide measures of relative likelihood that a subject belongs to a phenotypic status of interest (e.g., having a disease, and/or severity of a disease, and/or remission of the disease, etc.). As such, biomarkers can find use as markers for, for example, disease (diagnostics), severity of disease, therapeutic effectiveness of a treatment, and the like. Biomarkers are thus analytes in assays that facilitate diagnosis, theranostics, monitoring efficacy of treatment, monitoring presence absence or severity of disease, and the like.

A "biological fluid sample" or "body fluid sample" encompasses a variety of fluid sample types obtained from an individual. The definition encompasses whole blood and blood fractions (e.g., serum, plasma); and other liquid samples of biological origin (e.g., saliva, urine, bile fluid). "Blood sample" refers to a biological sample, which is obtained from blood of a subject, and includes whole blood and blood fractions (e.g., plasma or serum) suitable for analysis in the present methods. In general, separation of cellular components and non-cellular components in a blood sample (e.g., by centrifugation) without coagulation provides a blood plasma sample, while such separation of coagulated (clotted) blood provides a blood serum sample. Examples of biological samples of blood include peripheral blood or samples derived from peripheral blood. The definition also includes samples that have been manipulated after their procurement, such as by treatment with reagents, dilution, or enrichment for certain components, such as one or more analyte(s) to be assayed. For example, a biological sample (e.g., blood) can be enriched for a fraction containing an analyte(s) of interest.

"Isolated" refers to an entity of interest that is in an environment different from that in which the compound may naturally occur. "Isolated" is meant to include compounds that are within samples that are substantially enriched for the compound of interest and/or in which the compound of interest is partially or substantially purified.

By "purified" is meant a compound of interest (e.g., a polypeptide) has been separated from components that accompany it in nature. "Purified" can also be used to refer to a compound of interest separated from components that can accompany it during manufacture (e.g., in chemical synthesis). In some embodiments, a compound is substantially pure when it is at least 50% to 60%, by weight, free from organic molecules with which it is naturally associated or with which it is associated during manufacture. In some embodiments, the preparation is at least 75%, at least 90%, at least 95%, or at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample that contains the compound. A substantially pure compound can also be obtained by recombinant or chemical synthetic production. Purity can be measured by any appropriate method, e.g., chromatography, mass spectroscopy, high performance liquid chromatography analysis, etc.

As used herein, the terms "determining", "assessing", "assaying", "measuring" and "detecting" refer to both quantitative and semi-quantitative determinations and as such, the term "determining" is used interchangeably herein with "assaying," "measuring," and the like. Where a quantitative determination is intended, the phrase "determining an amount" of an analyte and the like is used. Where either a quantitative and semi-quantitative determination is intended, the phrase "determining a level" of an analyte or "detecting" an analyte is used.

"Quantitative" assays in general provide information on the amount of an analyte in a sample relative to a reference (control), and are usually reported numerically, where a "zero" value can be assigned where the analyte is below the limit of detection. "Semi-quantitative" assays involve presentation of a numeric representation of the amount of the analyte in the specimen that is relative to a reference (e.g., a threshold, e.g., normal threshold or an abnormal threshold), where a "zero" value can be assigned where the analyte is below the limit of detection. In general, semi-quantitative results are compared against an accompanying reference interval to provide a qualitative interpretation of the result.

"Sensitivity" refers to the fraction of people with a phenotype (e.g., presence or absence of disease, severity of disease, etc.) that a test correctly identifies as positive. "Specificity" refers to the fraction of people without the phenotype (e.g., presence or absence of disease, severity of disease, etc.) that the test correctly identifies as negative. The fractions with respect to sensitivity and/or specificity may be presented as a percentage. Where expressed as percentages, specificity can be calculated as by subtracting the sensitivity value for incorrect diagnosis from 100. For example, if a test used an algorithm for diagnosis of PSC also incorrectly identified PSC in 8% of AIH cases, the specificity for PSC against AIH would be 92%.

"Antibody" as used herein refers to an antigen-binding protein having one or more polypeptides that can be genetically encodable by immunoglobulin genes, or fragments of immunoglobulin genes, and which bind an antigen of interest. "Antibody" as used herein encompasses whole antibodies as well antigen-binding fragments of whole antibodies.

Antigen-binding antibody fragments include, for example, Fab', (Fab')2, and the like. "Fab" as used herein refers to a minimal antigen-binding portion of an antibody that lacks an Fc portion (e.g., a heterodimer of a VH/VL pair of a tetrameric antibody). "(Fab')2" refers to Fab molecules that are covalently linked, usually covalently linked as found in nature, which lack an Fc portion. It should be noted that while various antibody fragments may be defined in terms of the digestion of an intact antibody, one of skill will appreciate that such fragments may be synthesized de novo either chemically or by utilizing recombinant DNA methodology.

Whole antibodies refers to antibodies composed of two pairs of polypeptides, where each pair includes one "light" chain polypeptide and one "heavy" chain polypeptide. The terms variable light chain (VL) and variable heavy chain (VH) refer to the portions of the light and heavy chains that contain the CDRs, respectively. Light chains can be classified according to their constant regions, which can be kappa or lambda. Heavy chains can be classified according to their constant regions, which can be gamma, mu, alpha, delta, or epsilon, which in turn define the immunoglobulin classes, IgG, IgM, IgA, IgD and IgE, respectively.

The term "antibody" encompasses polyclonal and monoclonal antibodies, and further encompasses antibodies of any class (e.g., IgM, IgG, and subclasses thereof). "Antibody" also encompasses hybrid antibodies, bispecific antibodies, heteroantibodies, chimeric antibodies, humanized antibodies, and functional fragments thereof, which retain antigen binding. "Bispecific antibodies" may resemble single antibodies (or antibody fragments) but have two different antigen binding sites (variable regions). Heteroantibodies refers to two or more antibodies, or antigen-binding fragments (e.g., Fab) linked together, each antibody or fragment having a different specificity. The antibodies may be conjugated to other moieties, and/or may be bound to a support (e.g., a solid support), such as a polystyrene plate or bead, test strip, and the like.

The phrase "specifically binds", when referring to a protein or a binding partner that binds a protein (e.g., an antibody that binds an antigen (e.g., marker)), refers to a binding reaction between a protein and a binding partner (e.g., antibody and antigen) which is determinative of the presence of the protein in the presence of a heterogeneous population of proteins and other biologics. Thus, under designated conditions, a specified binding partner (e.g., antibody) binds preferentially to a particular protein and does not bind in a significant amount to other proteins present in the sample.

The terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The phrase "therapeutically effective amount" refers to the administration of an agent to a subject, either alone or as a part of a pharmaceutical composition and either in a single dose or as part of a series of doses, in an amount that is capable of having any detectable, positive effect on any symptom, aspect, or characteristics of a disease, disorder or condition when administered to a patient. The therapeutically effective amount can be ascertained by measuring relevant physiological effects.

The term "pharmaceutically acceptable" as used herein refers to a substance approved or approvable by a regulatory agency or listed in the U.S. Pharmacopeia, European Pharmacopeia, or other generally recognized pharmacopeia for use in animals, including humans.

The terms "pharmaceutically acceptable excipient, carrier, or adjuvant" or "acceptable pharmaceutical carrier" as used herein refer to an excipient, carrier, or adjuvant that can be administered to a subject, together with at least one therapeutic agent (e.g., an antibody), and which does not have an effect on the pharmacological activity of the therapeutic agent. In general, those of skill in the art and the U.S. FDA consider a pharmaceutically acceptable excipient, carrier, or adjuvant to be an inactive ingredient of any formulation.

The term "pharmaceutical formulation" or "pharmaceutical composition" as used herein refers to a preparation that is in such form as to permit the biological activity of the agent (e.g., an antibody) to be effective. A pharmaceutical formulation or composition generally comprises additional components, such as a pharmaceutically acceptable excipient, carrier, adjuvant, buffers, etc.

Methods of Diagnosing Presence of Advanced Stage Autoimmune Liver Disease

The methods disclosed herein provide a non-invasive means for determining progression of an autoimmune liver disease (ALD), such as, autoimmune hepatitis (AIH), primary biliary cholangitis (PBC), and/or primary sclerosing cholangitis (PSC). These methods are useful for determining likelihood of presence of advanced ALD in a subject. In certain aspects, the method can be used for identifying or diagnosing a subject as having an advanced stage ALD and providing a treatment appropriate for the advanced stage of the disease.

In certain aspects, the method may include assaying in a body fluid sample of a subject a level of the chemokine CX3CL1, where a level of CX3CL1 higher than a threshold CX3CL1 level indicates that the subject has increased likelihood of having an advanced stage ALD. In certain cases, advanced stage ALD may be ALD with fibrosis, or cirrhosis, or both. In certain cases, advanced stage ALD may be ALD with stage F4 fibrosis, or cirrhosis, or both. In certain cases, advanced stage ALD may be ALD with decompensated cirrhosis. In certain cases, advanced stage ALD may be ALD with at least one of fibrosis (e.g., stage F4 fibrosis) and decompensated cirrhosis. In certain aspects, the subject may have or may be suspected of having an ALD, such as, AIH, PBC, or PSC.

In certain aspects, the method may include assaying in a body fluid sample of a subject having or suspected of having PBC, a level of the chemokine CX3CL1. A level of CX3CL1 higher than a threshold CX3CL1 level indicates that the subject has increased likelihood of having an advanced stage PBC. In certain embodiments, a level of CX3CL1 higher than a threshold CX3CL1 level indicates that the subject has stage 1 liver fibrosis or higher, such as, stage 2 liver fibrosis, stage 3 liver fibrosis, stage 4 liver fibrosis, or cirrhosis, such as, decompensated cirrhosis. In certain aspects, the subject may be diagnosed as having an advanced stage PBC (such as PBC with one or more of stage F4 liver fibrosis or cirrhosis, e.g., decompensated cirrhosis) when the level of CX3CL1 in a body fluid sample of the subject having or suspected of having PBC, is at or above a threshold CX3CL1 level. In certain aspects, a subject having PBC may be diagnosed as having an advanced stage PBC (with a stage F4 liver fibrosis or cirrhosis, e.g., decompensated cirrhosis) when the level of CX3CL1 in a body fluid sample of the subject having PBC is at or above a threshold CX3CL1 level. Thus in some embodiments, the presently disclosed methods may be used to distinguish a subject with an advanced stage PBC from subjects having PBC at a less advanced stage.

In certain aspects, the method may include assaying in a body fluid sample of a subject having or suspected of having PSC, a level of the chemokine CX3CL1. A level of CX3CL1 higher than a threshold CX3CL1 level indicates that the subject has increased likelihood of having an advanced stage PSC. In certain embodiments, a level of CX3CL1 higher than a threshold CX3CL1 level indicates that the subject has stage 1 liver fibrosis or higher, such as, stage 2 liver fibrosis, stage 3 liver fibrosis, stage 4 liver fibrosis, or cirrhosis, such as, decompensated cirrhosis. In certain aspects, the subject may be diagnosed as having an advanced stage PSC (such as PSC with one or more of stage F4 liver fibrosis or cirrhosis, e.g., decompensated cirrhosis) when the level of CX3CL1 in a body fluid sample of the subject having or suspected of having PSC, is at or above a threshold CX3CL1 level. In certain aspects, a subject having PSC may be diagnosed as having an advanced stage PSC (with a stage F4 liver fibrosis or cirrhosis, e.g., decompensated cirrhosis) when the level of CX3CL1 in a body fluid sample of the subject having PSC is at or above a threshold CX3CL1 level. Thus in some embodiments, the presently disclosed methods may be used to distinguish a subject with an advanced stage PSC from subjects having PSC at a less advanced stage.

In certain aspects, the method may include assaying in a body fluid sample of a subject having or suspected of having AIH, a level of the chemokine CX3CL1. A level of CX3CL1 higher than a threshold CX3CL1 level indicates that the subject has increased likelihood of having an advanced stage AIH. In certain embodiments, a level of CX3CL1 higher than a threshold CX3CL1 level indicates that the subject has stage 1 liver fibrosis or higher, such as, stage 2 liver fibrosis, stage 3 liver fibrosis, stage 4 liver fibrosis, or cirrhosis, such as, decompensated cirrhosis. In certain aspects, the subject may be diagnosed as having an advanced stage AIH (such as AIH with one or more of stage F4 liver fibrosis or cirrhosis, e.g., decompensated cirrhosis) when the level of CX3CL1 in a body fluid sample of the subject having or suspected of having AIH, is at or above a threshold CX3CL1 level. In certain aspects, a subject having AIH may be diagnosed as having an advanced stage AIH (with a stage F4 liver fibrosis or cirrhosis, e.g., decompensated cirrhosis) when the level of CX3CL1 in a body fluid sample of the subject having AIH is at or above a threshold CX3CL1 level. Thus in some embodiments, the presently disclosed methods may be used to distinguish a subject with an advanced stage AIH from subjects having AIH at a less advanced stage.

In certain embodiments, the method may include performing the assaying step and recommending treatment based on the level of CX3CL1 and the diagnosis of presence of advanced stage of the ALD. For example, a subject diagnosed as having advanced stage ALD (e.g., PBC, PSC, or AIH) may be treated using an aggressive treatment regimen. In certain embodiments, a subject diagnosed as having an advanced stage ALD (e.g., having PBC, PSC, or AIH with liver fibrosis, cirrhosis, and/or decompensated cirrhosis) may be treated with liver transplantation. In certain embodiments, a subject diagnosed as having an advanced stage ALD may be treated with one or more of ursodeoxycholic acid (UDCA), obeticholic acid, methotrexate, corticosteroids (e.g., prednisone), immunosuppressants (e.g., 6-mercaptopurine, azathioprine, etc.), cyclosporine, and colchicine. In certain embodiments, a subject diagnosed as having an advanced stage ALD, such as PBC or PSC, may be treated with ursodeoxycholic acid at high doses (28 mg/kg/day to 30 mg/kg/day) and the treatment may be combined with obeticholic acid. In certain embodiments, a subject diagnosed as having an advanced stage ALD, such as, AIH, may be treated with immunosuppressants (e.g., 6-mercaptopurine, azathioprine, etc.) and in certain cases, the treatment with immunosuppressants may be combined with corticosteroids (e.g., prednisone). In certain embodiments, a subject diagnosed as having an advanced stage ALD, such as, AIH, may be treated with corticosteroids (e.g., prednisone) and in certain cases, the treatment with corticosteroids may be combined with immunosuppressants (e.g., 6-mercaptopurine, azathioprine, etc.). In certain embodiments, a subject diagnosed as having PSC may be treated with an experimental therapy or an off-label drug or both.

In certain embodiments, the method may include performing the assaying step over time and recommending treatment based on the level of CX3CL1, where an increasing CX3CL1 level may warrant more frequent tests and/or more aggressive therapy.

"Threshold biomarker level", which may also be referred to herein as a "cutoff value" or "threshold value", refers to a biomarker level that can be used to distinguish between a first condition and a second (e.g., between individuals who do not have an advanced stage ALD and individuals who have such an advanced stage ALD or a subject having AIH vs. a subject not having AIH) such that a biomarker level in a sample that is above a control level indicates an increased likelihood of the second condition in the individual. Thus, a "control biomarker level" or "biomarker threshold value" refers to an assay value (e.g., amount of a biomarker)), which is an approximate value that distinguishes the likelihood that a condition is present in the individual tested from the likelihood that a condition is not present in the individual tested, with a pre-selected specificity and/or sensitivity.

For example, a biomarker threshold value can represent an approximate level of a biomarker that detects affected subjects at a desired sensitivity (e.g., at least 55%, at least about 60%, at least 70%, or at least 80% or more). Thus, for example, an individual having a biomarker level that is greater than a threshold value has at least about 60% or greater likelihood of having that condition.

It will be appreciated that the precise number value for control or threshold values can vary with the type of assay and reagents used to detect the biomarkers as well as the sensitivity and specificity desired from the assay. For example, the assay values upon which the threshold values for CX3CL1, CCL19, and CXCL9 described herein are based on assay values obtained using serum samples and a multiplex ELISA kit from Meso Scale Discovery Company. However, regardless of the assay and reagents used, the correlations between a threshold or cut off value of a biomarker and likelihood of a disease state (e.g., advanced stage of one or more of AIH, PBC, and PSC; relapse or remission of one or more of AIH, PBC, and PSC) will be present regardless of the assays and reagents used. Thus, so long as the test samples are assayed for the biomarker (e.g., CX3CL1, CCL19, and/or CXCL9) using an assay platform and reagents of the same general type (e.g., polypeptide assay) and similar sensitivity as the assay platform and reagents used to determine the control/threshold values of the biomarker (CX3CL1 and/or CXCL9, respectively), the findings upon which the methods of the present disclosure are based will be preserved.

The threshold CX3CL1 level (also referred to as CX3CL1 cutoff value), can be determined as described herein, e.g., by assaying CX3CL1 levels in control populations and in subjects with a known condition (e.g., with advanced stage ALD, e.g., AIH, PBC, or PSC with F4 fibrosis and/or cirrhosis (e.g. decompensated cirrhosis) and, through application of statistical analysis, identifying a CX3CL1 level that is present in at least 20%, at least 25%, at least 30%, at least 40%, at least 50%, at least 55%, at least about 60%, at least 70%, at least 80%, or at least 90% or more of patients having advanced stage ALD and provides a specificity of at least 80%, at least 90%, at least 95%, at least 98%, at least 99%, or at least 100%.

Threshold CX3CL1 level is useful for differentiating a patient with an advanced stage ALD from an ALD patient at an earlier disease state can be readily determined using reagents and methods known in the art, and may vary with the assay used and the biological sample used. For example, where the assay is an immunoassay and the biological sample is serum, the threshold CX3CL1 level can be about 4000-6000 pg/ml serum, about 4500-6000 pg/ml serum, about 5000-6000 pg/ml serum, about 4000-5800 pg/ml serum, about 4000-5700 pg/ml serum, about 4000-5500 pg/ml serum, about 4500-5500 pg/ml serum, about 4700-5700 pg/ml serum, about 4600-5500 pg/ml serum, about 5200-5700 pg/ml serum, about 5000-5700 pg/ml serum, e.g., 6000 pg/ml serum, 5800 pg/ml serum, 5700 pg/ml serum, about 5600 pg/ml serum, 5500 pg/ml serum, about 5400 pg/ml serum, 5300 pg/ml serum, 5200 pg/ml serum, about 5100 pg/ml serum, 5000 pg/ml serum, 4800 pg/ml serum, 4500 pg/ml serum, or 4000 pg/ml serum, such that a measured CX3CL1 level that is greater than or equal to the threshold CX3CL1 level indicates a diagnosis of advanced stage ALD (e.g., AIH, PBC, or PSC with stage F4 fibrosis and/or cirrhosis, e.g., decompensated cirrhosis).

In certain embodiments, the method may include diagnosing stage F4 fibrosis in a patient having PBC or PSC. The method may include assaying level of CX3CL1 in a serum sample of the patient, where a CX3CL1 level higher than or equal to a threshold CX3CL1 level in the range of 4000-6000 pg/ml may indicate presence of stage F4 fibrosis in the PBC or PSC patient.

In certain embodiments, the method may include diagnosing cirrhosis in a patient having PBC or PSC. The method may include assaying the level of CX3CL1 in a serum sample of the patient, where a CX3CL1 level higher than or equal to a threshold CX3CL1 level in the range of 4000-6000 pg/ml may indicate presence of cirrhosis in the PBC or PSC patient.

In certain embodiments, the method may include diagnosing decompensated cirrhosis in a patient having PBC or PSC. The method may include assaying the level of CX3CL1 in a serum sample of the patient, where a CX3CL1 level higher than or equal to a threshold CX3CL1 level in the range of 4000-6000 pg/ml may indicate presence of decompensated cirrhosis in the PSC patient.

Assays using CX3CL1 levels according to the present disclosure to facilitate a diagnosis of advanced stage ALD with a desired sensitivity (e.g., at least 20%, at least 30%, at least 40%, at least 45%, at least 50%, at least 55%, at least 60%, at least 70%, at least 75%, at least 80%, at least 90%, at least 95% or greater), and with a desired specificity (e.g., at least 80%, at least 85%, at least 90%, at least 95% or greater).

In certain aspects, measurement of level of CX3CL1 may be used to monitor progression of disease in a patient diagnosed with ALD. For example, level of CX3CL1 may be measured over a period of time and an increase in level of CX3CL1 over the period of time may indicate increase in severity of the disease. A subject that is identified as having a worsening condition may be treated with an aggressive treatment regimen, such as, a liver transplant. The increase in level may be at least about 20%, at least about 25%, at least about 30%, at least about 35%, at least about 40%, or more compared to the level from a previous measurement.

In certain aspects, threshold level of a cytokine for diagnosing a subject as having ALD may be based on the level of the cytokine in healthy subjects (i.e., subjects who do not appear to have any symptoms of ALD). A threshold level may be a range of the level of the cytokine present in healthy subjects. Thus, a level of the cytokine higher than this threshold is indicative of presence of ALD.

Methods of Monitoring ALD Treatment

Also provided herein are assays and methods for monitoring effectiveness of a treatment for ALD, such as, AIH, PSC, or PBC. In certain embodiments, a subject receiving treatment for an ALD may be monitored by assaying in a body fluid sample of the subject a level of one or more of biomarker selected from the group consisting of: CX3CL1, MIG (CXCL9), and CCL19 (MIP-3β), where a level of one or more of the biomarker lower than a threshold level of the respective biomarker, indicates that the subject is responding positively to the treatment. In certain embodiments, a subject receiving treatment for an ALD may be monitored by assaying in a body fluid sample of the subject a level of CX3CL1, where a level of CX3CL1 lower than a threshold level of CX3CL1, indicates that the subject is responding positively to the treatment. In certain embodiments, a subject receiving treatment for an ALD may be monitored by assaying in a body fluid sample of the subject a level of CCL19, where a level of CCL19 lower than a threshold level of CCL19, indicates that the subject is responding positively to the treatment. In certain embodiments, a subject receiving treatment for an ALD may be monitored by assaying in a body fluid sample of the subject a level of CX3CL1 and MIG (CXCL9), where a level of CX3CL1 lower than a threshold level of CX3CL1 and/or a level of MIG lower than a threshold level of MIG, indicates that the subject is responding positively to the treatment. In certain embodiments, a subject receiving treatment for an ALD may be monitored by assaying in a body fluid sample of the subject a level of CX3CL1 and CCL19, where a level of CX3CL1 lower than a threshold level of CX3CL1 and/or a level of CCL lower than a threshold level of CCL19, indicates that the subject is responding positively to the treatment. In certain embodiments, a subject receiving treatment for an ALD may be monitored by assaying in a body fluid sample of the subject a level of MIG and CCL19, where a level of MIG lower than a threshold level of MIG and/or a level of CCL lower than a threshold level of CCL19, indicates that the subject is responding positively to the treatment. In certain embodiments, a subject receiving treatment for an ALD may be monitored by assaying in a body fluid sample of the subject a level of CX3CL1, MIG and CCL19, where a level of CX3CL1 lower than a threshold level of CX3CL1, a level of MIG lower than a threshold level of MIG, and/or a level of CCL lower than a threshold level of CCL19, indicates that the subject is responding positively to the treatment. In certain embodiments, a subject receiving treatment for an ALD may be monitored by assaying in a body fluid sample of the subject a level of one or more of CX3CL1, MIG, CCL19, and Eotaxin-3, where a level of CX3CL1 lower than a threshold level of CX3CL1, a level of MIG lower than a threshold level of MIG, a level of CCL19 lower than a threshold level of CCL19, and/or a level of Eotaxin-3 lower than a threshold level of indicates that the subject is responding positively to the treatment. In some embodiments, the subject is diagnosed as having AIH and is receiving treatment for AIH. In some embodiments, the subject is diagnosed as having PBC and is receiving treatment for PBC.

In some embodiments, the subject is diagnosed as having AIH and is receiving treatment for AIH and the method for monitoring effectiveness of treatment comprises measuring one or more of CX3CL1, MIG, CCL19, and Eotaxin-3, where a level of CX3CL1 lower than a threshold level of CX3CL1, a level of MIG lower than a threshold level of MIG, a level of CCL19 lower than a threshold level of CCL19, and/or a level of Eotaxin-3 lower than a threshold level of indicates that the subject is responding positively to the treatment.

In certain embodiments, a method for treating a subject diagnosed with AIH is disclosed. The method may include administering a treatment for AIH, where the treatment comprises administering a corticosteroid such as prednisone and/or an immunosuppressant such as azathioprine and measuring one or more of CX3CL1, MIG, CCL19, and Eotaxin-3, where a level of CX3CL1 lower than a threshold level of CX3CL1, a level of MIG lower than a threshold level of MIG, a level of CCL lower than a threshold level of CCL19, and/or a level of Eotaxin-3 lower than a threshold level of indicates that the subject is responding positively to the treatment.

In other embodiments, methods for monitoring effectiveness of a treatment for ALD, such as, AIH, PSC, or PBC may include monitoring level of one or more of CX3CL1, CCL19, MIG and E3 at a plurality of time points during the course of treatment. For example, monitoring effectiveness of a treatment for ALD in a subject may include determining level of CX3CL1 in a body fluid sample of the subject at a first time point and at a second time point to obtain a first CX3CL1 and a second CX3CL1 level, respectively, where the second time point is later than the first time; comparing the first and second CX3CL1 levels, wherein increase in the second CX3CL1 level compared to the first CX3CL1 or a lack of change in the second CX3CL1 level compared to the first CX3CL1 indicates that the subject is not responding positively to the treatment and wherein a decreased second CX3CL1 level compared to the first CX3CL1 indicates that the subject is responding positively to the treatment. For example, monitoring effectiveness of a treatment for ALD in a subject may include determining level of CCL19 in a body fluid sample of the subject at a first time point and at a second time point to obtain a first CCL19 and a second CCL19 level, respectively, where the second time point is later than the first time; comparing the first and second CCL19 levels, wherein increase in the second CCL19 level compared to the first CCL19 or a lack of change in the second CCL19 level compared to the first CCL19 indicates that the subject is not responding positively to the treatment and wherein a decreased second CCL level compared to the first CCL19 indicates that the subject is responding positively to the treatment. In another example, monitoring effectiveness of a treatment for ALD in a subject may include determining level of MIG in a body fluid sample of the subject at a first time point and at a second time point to obtain a first MIG and a second MIG level, respectively, where the second time point is later than the first time; comparing the first and second MIG levels, wherein increase in the second MIG level compared to the first MIG or a lack of change in the second MIG level compared to the first MIG indicates that the subject is not responding positively to the treatment and wherein a decreased second MIG level compared to the first MIG indicates that the subject is responding positively to the treatment. As noted herein, the markers may be combined, such that levels of i) CX3CL1; (ii) CCL19; (iii) CX3CL1 and CCL19; (iv) CX3CL1 and CXCL9; (v) CCL19 and CXCL9; or (vi) CX3CL1, CXCL9, and CCL19 are measured in a method for monitoring effectiveness of a treatment for ALD, such as, AIH, PSC, or PBC.

In certain aspects, the ALD is AIH and the subject is receiving treatment for AIH and the method comprises measuring a level of one or more of the biomarkers: CX3CL1, CXCL9, CCL19, and E3 at a first time point during treatment and a second time point, after the first time point, during treatment and comparing the levels, wherein increase in the level of the one or more biomarker at the second time point compared to the first time point or a lack of change in the level of the one or more biomarker at the second time point compared to the first time point indicates that the subject is not responding positively to the treatment and wherein a decreased level of the one or more biomarker at the second time point compared to the first time point indicates that the subject is responding positively to the treatment. In certain aspects, the treatment comprises administering a corticosteroid such as prednisone and/or an immunosuppressant such as azathioprine.

Monitoring effectiveness of treatment using the assays disclosed herein may be useful for making treatment decisions. In certain embodiments, the method may include receiving results from measuring a level of one or more of CX3CL1, CCL19, CXCL9, and E3 in a body fluid sample of a subject diagnosed as having ALD and receiving a treatment for ALD; wherein (i) when the level of CX3CL1, CCL19, E3, and/or CXCL9 is above a cut-off level indicative of positive response to the treatment, the method may further comprise altering the treatment, wherein altering the treatment comprises changing the treatment regimen by increasing dose and/or dosage of the active agent administered to the subject or changing the active agent administered to the subject or (ii) when the level of CX3CL1, CCL19, E3 and/or CXCL9 is below the cut-off level indicative of positive response to the treatment, the method may further comprise tapering the dose and/or dosage of the treatment or terminating the treatment. Similarly, treatment may be changed based on levels of the one or more of the biomarkers CX3CL1, CCL19, E3 and CXCL9 monitored at a plurality of time points during the course of treatment. In certain aspects, the subject may be receiving treatment for AIH.

Monitoring effectiveness of treatment using the assays disclosed herein may be useful for identifying new treatments for ALD. Accordingly, a method of identifying new treatments for ALD is also disclosed. In certain embodiments, an experimental treatment that may be assessed by the disclosed assays may include administering a candidate drug, such as, a drug used for treating another liver disease, or administering a new therapeutic regimen of drug used for treating ALD, and the like. The method may include administering the experimental treatment to a subject diagnosed with ALD and assaying level of CX3CL1, MIP3b, E3, and/or CXCL9 in a body fluid sample of the subject, wherein a decreased level of CX3CL1, MIP3b, E3, and/or CXCL9 is indicative of effectiveness of the treatment. The level may be decreased compared to a threshold level or a baseline level (level prior to start of treatment). In certain embodiments, the level may be measured at multiple time points and a downward trend in the level identifies the candidate drug or the new therapeutic regimen as a treatment for the ALD.

In certain embodiments, a decrease of about 25% or more, about 30% or more, about 35% or more, about 40% or more, about 45% or more, or about 50% or more is indicative of a positive response to treatment.

Monitoring PBC Treatment

In certain embodiments, a subject receiving treatment for ALD may be a subject who has been diagnosed as having PBC and is receiving treatment for PBC. The treatment may be a standard of care treatment such as an FDA approved treatment for PBC. In certain embodiments, the treatment may be administration of UDCA or a derivative thereof with or without obeticholic acid. In certain embodiments, the treatment may be an immunosuppressive therapy, such as, predniso (lo) ne or budesonide with or without azathioprine.

A subject diagnosed with PBC and receiving a treatment for PBC may be monitored to determine whether the subject is responding to the therapy by measuring level of CX3CL1 and/or MIP-3β in a biological sample, such as, blood, serum, or plasma sample. The assaying may be performed after a predetermined time after commencement of treatment and may be performed once or a number of times, such as, 2-10 times, where the timing of procurement of biological sample from the subject is separated by any suitable time period, which may, be periodic or need-based, e.g., based on worsening of symptoms of the patient. The method may include measuring CX3CL1 and/or MIP-3β level after a period of treatment, such as, after 1 week, 2 weeks, 3 weeks, 1 month, 3 months, 6 months, 1 year, 3 years or more after the start of the treatment and may be before start of treatment (at day 0) to obtain a baseline level. In certain cases, the method may include measuring CX3CL1 and/or MIP-3β in a PBC patient receiving treatment for PBC at a first time point and a second time point subsequent to the first time point in order to determine effectiveness of the treatment.

As noted in the previous section, a threshold level of a biomarker, such as CX3CL1, can be determined by assaying PBC patients known to have responded to the treatment and PBC patients known to not have responded to the treatment. Responders and non-responders can be determined using pre-existing standard-of-care clinical and biochemical tests currently in use to determine whether a patient is responsive to treatment. For example, a PBC patient responsive to a treatment may have an alkaline phosphatase (ALP) blood/serum level under 200 units/liter. In another example, a PBC patient responsive to a treatment may be identified using the scoring system described in Carbone M. et. al., Hepatology. 2016 March; 63(3):930-50. In certain cases, a threshold level of a biomarker, such as CX3CL1, can be determined by assaying PBC patients known to have responded to the treatment and PBC patients known to not have responded to the treatment as determined by analysis of liver biopsy sample from these patients.

The threshold CX3CL1 value (also referred to as CX3CL1 cutoff value) that distinguishes a responder from a non-responder, can be determined as described herein, e.g., by assaying CX3CL1 levels in PBC patients known to be responders and, through application of statistical analysis, identifying a CX3CL1 level that is present in at least 20%, at least 25%, at least 30%, at least 40%, at least 50%, at least 55%, at least about 60%, at least 70%, at least 80%, or at least 90% or more of responders and provides a specificity of at least 80%, at least 90%, at least 95%, at least 98%, at least 99%, or at least 100%.

Threshold CX3CL1 value useful for monitoring efficacy of treatment may vary with the assay used and the biological sample used. For example, where the assay is an immunoassay and the biological sample is serum, the threshold CX3CL1 level can be about 2000-7000 pg/ml, about 2100-7000 pg/ml, about 3000-7000 pg/ml, about 4000-7000 pg/ml, about 5000-7000 pg/ml, about 5500-6500 pg/ml, about 5500-6250 pg/ml, about 5750-6250 pg/ml, or about 5000-6000 pg/ml, 2100-3000 pg/ml, about 2200-3000 pg/ml, about 2300-3000 pg/ml, about 2400-3000 pg/ml, about 2200-2900 pg/ml, about 2200-2800 pg/ml, about 2200-2700 pg/ml, or about 2300-2700 pg/ml, e.g., 2000 pg/ml, 2200 pg/ml, 2500 pg/ml, about 2600 pg/ml, 2700 pg/ml, about 2800 pg/ml, 2900 pg/ml, 3000 pg/ml, 3300 pg/ml, 4000 pg/ml, 4300 pg/ml, 5000 pg/ml, 5300 pg/ml, or 6000 pg/ml, such that a measured CX3CL1 level that is lower than the threshold CX3CL1 level indicates that the patient is responding positively to the treatment and a measured CX3CL1 level that is higher than or equal to the threshold CX3CL1 level indicates that the patient is not responding positively to the treatment.

Threshold CCL19 value useful for monitoring efficacy of treatment may vary with the assay used and the biological sample used. For example, where the assay is an immunoassay and the biological sample is serum, the threshold CCL19 level can be about 500-2500 pg/ml, about 800-1200 pg/ml, about 800-1100 pg/ml, about 9000-1100 pg/ml, about 950-1100 pg/ml, or about 800-1500 pg/ml, e.g., 500 pg/ml, 700 pg/ml, 1000 pg/ml, about 1100 pg/ml, 1200 pg/ml, or about 1500 pg/ml, such that a measured CCL19 level that is lower than the threshold CCL level indicates that the patient is responding positively to the treatment and a measured CCL19 level that is higher than or equal to the threshold CCL19 level indicates that the patient is not responding positively to the treatment.

As noted, in certain cases, both CX3CL1 and CCL19 may be measured and levels of one or both of these markers may be used to determine whether an AIH patient is responding positively to the treatment.

In certain embodiments, monitoring of efficacy of treatment for PBC may be performed by assaying CX3CL1 and/or CCL19 in conjunction with assaying an additional biomarker, CXCL9, in a body fluid sample of the subject, where a decrease in the level CXCL9 compared to a threshold CXCL9 level indicates that the patient is responding positively to the treatment. Similar to CX3CL1, threshold CXCL9 value useful for differentiating a responder from a non-responder can be readily determined using reagents and methods known in the art, and may vary with the assay used and the biological sample used. For example, where the assay is an immunoassay and the biological sample is serum, the threshold CXCL9 level can be about 300-1700 pg/ml, about 400-1700 pg/ml, about 500-1700 pg/ml, about 600-1700 pg/ml, about 700-1700 pg/ml, about 800-1700 pg/ml, about 900-1700 pg/ml, about 1000-1700 pg/ml, about 1200-1700 pg/ml, about 1300-1700 pg/ml, about 1400-1700 pg/ml, about 1400-1600 pg/ml, about 1400-1650 pg/ml, 300-1000 pg/ml, about 400-1000 pg/ml, about 500-1000 pg/ml, about 600-1000 pg/ml, about 400-900 pg/ml, about 400-800 pg/ml, about 500-900 pg/ml, or about 500-800 pg/ml, e.g., 500 pg/ml, 600 pg/ml, 700 pg/ml, about 800 pg/ml, 900 pg/ml, 1000 pg/ml, 1200 pg/ml, 1300 pg/ml, or about 1500 pg/ml, such that a measured CXCL9 level that is lower than the threshold CXCL9 level indicates that the patient is responding positively to the treatment and a measured CXCL9 level that is higher than or equal to the threshold CXCL9 level indicates that the patient is not responding positively to the treatment for PBC.

Monitoring AIH Treatment

In certain embodiments, a subject receiving treatment for ALD may be a subject who has been diagnosed as having AIH and is receiving treatment for AIH. The treatment may be a standard of care treatment such as an FDA approved treatment for AIH. In certain embodiments, the treatment may be administration of immunosuppressants and/or anti-inflammatory agents. In certain embodiments, the treatment may be administration of Prednis(ol)one (20-30 mg/day) with or without azathioprine.

A subject diagnosed with AIH and receiving a treatment for AIH may be monitored to determine whether the subject is responding to the therapy by measuring level of CX3CL1, MIP-3β, MIG, and/or E3 in a biological sample, such as, blood, serum, or plasma sample. The assaying may be performed after a predetermined time after commencement of treatment and may be performed once or a number of times, such as, 2-10 times, where the timing of procurement of biological sample from the subject is separated by any suitable time period, which may, be periodic or need-based, e.g., based on worsening of symptoms of the patient. The method may include measuring CX3CL1, MIP-3β, MIG, and/or E3 level after a period of treatment, such as, after 1 week, 2 weeks, 3 weeks, 1 month, 3 months, 6 months, 1 year, 3 years or more after the start of the treatment and may be before start of treatment (at day 0) to obtain a baseline level. In certain cases, the method may include measuring CX3CL1, MIP-3β, MIG, and/or E3 in an AIH patient receiving treatment for AIH at a first time point and a second time point subsequent to the first time point in order to determine effectiveness of the treatment.

As noted in the previous section, a threshold level of a biomarker, such as CX3CL1, can be determined by assaying AIH patients known to have responded to the treatment and patients known to not have responded to the treatment. Responders and non-responders can be determined using pre-existing standard-of-care clinical and biochemical tests currently in use to determine whether a patient is responsive to treatment. In certain cases, a threshold level of a biomarker, such as CX3CL1, can be determined by assaying AIH patients known to have responded to the treatment and AIH patients known to not have responded to the treatment as determined by analysis of liver biopsy sample from these patients. Normalization of liver enzymes levels, such as, ALT, AST, IgG, or a combination thereof, in the blood/serum may indicate that a patient is responsive to the treatment. In some instances, in order to conclude that a patient is responsive to a treatment, the normalized values have to be observed over a period of time (e.g., over a course of several days, weeks, or months). In some cases, a liver biopsy may be performed to determine whether a subject is responsive to the treatment.

The threshold CX3CL1 value (also referred to as CX3CL1 cutoff value) that distinguishes a responder to AIH treatment from a non-responder, can be determined as described herein, e.g., by assaying CX3CL1 levels in subjects known to be responders to AIH treatment and, through application of statistical analysis, identifying a CX3CL1 level that is present in at least 20%, at least 25%, at least 30%, at least 40%, at least 50%, at least 55%, at least about 60%, at least 70%, at least 80%, or at least 90% or more of responders and provides a specificity of at least 80%, at least 90%, at least 95%, at least 98%, at least 99%, or at least 100%.

Threshold CX3CL1 value useful for differentiating an AIH patient who is a responder from a non-responder can be readily determined using reagents and methods known in the art, and may vary with the assay used and the biological sample used. For example, where the assay is an immunoassay and the biological sample is serum, the threshold CX3CL1 level can be about 7000-13000 pg/ml, about 8000-12000 pg/ml, about 8000-11000 pg/ml, about 9000-11000 pg/ml, about 7000-11000 pg/ml, or about 8500-11000 pg/ml, e.g., 7000 pg/ml, 8000 pg/ml, 9000 pg/ml, about 10000 pg/ml, 11000 pg/ml, or about 1200 pg/ml, such that a measured CX3CL1 level that is lower than the threshold CX3CL1 level indicates that the AIH patient is responding positively to the treatment and a measured CX3CL1 level that is higher than or equal to the threshold CX3CL1 level indicates that the AIH patient is not responding positively to the treatment.

Threshold CCL19 value useful for differentiating an AIH patient who is a responder from a non-responder can be readily determined using reagents and methods known in the art, and may vary with the assay used and the biological sample used. For example, where the assay is an immunoassay and the biological sample is serum, the threshold CCL19 level can be about 500-2500 pg/ml, about 800-1200 pg/ml, about 800-1100 pg/ml, about 9000-1100 pg/ml, about 950-1100 pg/ml, or about 800-1500 pg/ml, e.g., 500 pg/ml, 700 pg/ml, 1000 pg/ml, about 1100 pg/ml, 1200 pg/ml, or about 1500 pg/ml, such that a measured CCL19 level that is lower than the threshold CCL19 level indicates that the AIH patient is responding positively to the treatment and a measured CCL level that is higher than or equal to the threshold CCL level indicates that the AIH patient is not responding positively to the treatment.

As noted, in certain cases, both CX3CL1 and CCL19 may be measured and levels of one or both of these markers may be used to determine whether an AIH patient is responding positively to the treatment.

In certain embodiments, monitoring of efficacy of treatment for AIH may be performed by assaying CX3CL1 and/or CCL19 in conjunction with assaying an additional biomarker, e.g., CXCL9 and CCL26 (E3) in a body fluid sample of the subject, where a decrease in the level CXCL9 compared to a threshold CXCL9 level and/or a decrease in the level E3 compared to a threshold E3 level indicates that the AIH patient is responding positively to the treatment.

Similar to CX3CL1, threshold CXCL9 value useful for differentiating a responder who is responding positively to an AIH treatment from a non-responder can be readily determined using reagents and methods known in the art, and may vary with the assay used and the biological sample used. For example, where the assay is an immunoassay and the biological sample is serum, the threshold CXCL9 level can be about 300-1000 pg/ml, about 400-1000 pg/ml, about 500-1000 pg/ml, about 600-1000 pg/ml, about 400-900 pg/ml, about 400-800 pg/ml, about 400-700 pg/ml, or about 400-600 pg/ml, e.g., 400 pg/ml, 500 pg/ml, 600 pg/ml, or about 700 pg/ml, such that a measured CXCL9 level that is lower than the threshold CXCL9 level indicates that the patient is responding positively to the AIH treatment and a measured CXCL9 level that is higher than or equal to the threshold CXCL9 level indicates that the patient is not responding positively to the AIH treatment.

Similar to CX3CL1, threshold Eotaxin-3 value useful for differentiating a responder who is responding positively to an AIH treatment from a non-responder can be readily determined using reagents and methods known in the art, and may vary with the assay used and the biological sample used. For example, where the assay is an immunoassay and the biological sample is serum, the threshold E-3 level can be about 18-30 pg/ml, such that a measured E3 level that is lower than the threshold E3 level indicates that the patient is responding positively to the AIH treatment and a measured E3 level that is higher than or equal to the threshold E3 level indicates that the patient is not responding positively to the AIH treatment.

Monitoring PSC Treatment

In certain embodiments, a subject receiving treatment for ALD may be a subject who has been diagnosed as having PSC and is receiving treatment for PSC. The treatment may be an experimental treatment. For example, the treatment may be off-label use of a drug, such as UDCA or a derivative thereof, obeticholic acid or a derivative thereof, immunosuppressants, antibiotics, combinations thereof, etc.

A subject diagnosed with PSC and receiving a treatment for PBC may be monitored to determine whether the subject is responding to the therapy by measuring level of CX3CL1 and/or MIP-3β in a biological sample, such as, blood, serum, or plasma sample. The assaying may be performed after a predetermined time after commencement of treatment and may be performed once or a number of times, such as, 2-10 times, where the timing of procurement of biological sample from the subject is separated by any suitable time period, which may, be periodic or need-based, e.g., based on worsening of symptoms of the patient. The method may include measuring CX3CL1 and/or MIP-3β level after a period of treatment, such as, after 1 week, 2 weeks, 3 weeks, 1 month, 3 months, 6 months, 1 year, 3 years or more after the start of the treatment and may be before start of treatment (at day 0) to obtain a baseline level. In certain cases, the method may include measuring CX3CL1 and/or MIP-3β in a PSC patient receiving treatment for PSC at a first time point and a second time point subsequent to the first time point in order to determine effectiveness of the treatment.

As noted in the previous section, a threshold level of a biomarker, such as CX3CL1, can be determined by assaying PSC patients known to have responded to the treatment and PSC patients known to not have responded to the treatment. Responders and non-responders can be determined using pre-existing standard-of-care clinical and biochemical tests currently in use to determine whether a patient is responsive to treatment.

The threshold CX3CL1 value (also referred to as CX3CL1 cutoff value) that distinguishes a responder from a non-responder, can be determined as described herein, e.g., by assaying CX3CL1 levels in PSC patients known to be responders and, through application of statistical analysis, identifying a CX3CL1 level that is present in at least 20%, at least 25%, at least 30%, at least 40%, at least 50%, at least 55%, at least about 60%, at least 70%, at least 80%, or at least 90% or more of responders and provides a specificity of at least 80%, at least 90%, at least 95%, at least 98%, at least 99%, or at least 100%.

Threshold CX3CL1 value useful for monitoring efficacy of treatment, and may vary with the assay used and the biological sample used. For example, where the assay is an immunoassay and the biological sample is serum, the threshold CX3CL1 level can be about 2000-7000 pg/ml, about 2100-7000 pg/ml, about 3000-7000 pg/ml, about 4000-7000 pg/ml, about 5000-7000 pg/ml, about 5500-6500 pg/ml, about 5500-6250 pg/ml, about 5750-6250 pg/ml, or about 5000-6000 pg/ml, 2100-3000 pg/ml, about 2200-3000 pg/ml, about 2300-3000 pg/ml, about 2400-3000 pg/ml, about 2200-2900 pg/ml, about 2200-2800 pg/ml, about 2200-2700 pg/ml, or about 2300-2700 pg/ml, e.g., 2000 pg/ml, 2200 pg/ml, 2500 pg/ml, about 2600 pg/ml, 2700 pg/ml, about 2800 pg/ml, 2900 pg/ml, 3000 pg/ml, 3300 pg/ml, 4000 pg/ml, 4300 pg/ml, 5000 pg/ml, 5300 pg/ml, or 6000 pg/ml, such that a measured CX3CL1 level that is lower than the threshold CX3CL1 level indicates that the patient is responding positively to the treatment and a measured CX3CL1 level that is higher than or equal to the threshold CX3CL1 level indicates that the patient is not responding positively to the treatment.

Threshold CCL19 value useful for differentiating an PSC patient who is a responder from a non-responder can be readily determined using reagents and methods known in the art, and may vary with the assay used and the biological sample used. For example, where the assay is an immunoassay and the biological sample is serum, the threshold CCL19 level can be about 500-2500 pg/ml, about 800-1200 pg/ml, about 800-1100 pg/ml, about 9000-1100 pg/ml, about 950-1100 pg/ml, or about 800-1500 pg/ml, e.g., 500 pg/ml, 700 pg/ml, 1000 pg/ml, about 1100 pg/ml, 1200 pg/ml, or about 1500 pg/ml, such that a measured CCL19 level that is lower than the threshold CCL level indicates that the AM patient is responding positively to the treatment and a measured CCL level that is higher than or equal to the threshold CCL level indicates that the AM patient is not responding positively to the treatment.

As noted, in certain cases, both CX3CL1 and CCL19 may be measured and levels of one or both of these markers may be used to determine whether a PSC patient is responding positively to the treatment.

In certain embodiments, monitoring of efficacy of treatment for PSC may be performed by assaying CX3CL1 and/or CCL19 in conjunction with assaying an additional biomarker, CXCL9, in a body fluid sample of the subject, where a decrease in the level CXCL9 compared to a threshold CXCL9 level indicates that the patient is responding positively to the treatment. Similar to CX3CL1, threshold CXCL9 value useful for differentiating a responder from a non-responder can be readily determined using reagents and methods known in the art, and may vary with the assay used and the biological sample used. For example, where the assay is an immunoassay and the biological sample is serum, the threshold CXCL9 level can be about 300-1700pg/ml, about 400-1700 pg/ml, about 500-1700 pg/ml, about 600-1700 pg/ml, about 700-1700 pg/ml, about 800-1700 pg/ml, about 900-1700 pg/ml, about 1000-1700 pg/ml, about 1200-1700 pg/ml, about 1300-1700 pg/ml, about 1400-1700 pg/ml, about 1400-1600 pg/ml, about 1400-1650 pg/ml, 300-1000pg/ml, about 400-1000 pg/ml, about 500-1000 pg/ml, about 600-1000 pg/ml, about 400-900 pg/ml, about 400-800 pg/ml, about 500-900 pg/ml, or about 500-800 pg/ml, e.g., 500 pg/ml, 600 pg/ml, 700 pg/ml, about 800 pg/ml, 900 pg/ml, 1000 pg/ml, 1200 pg/ml, 1300 pg/ml, or about 1500 pg/ml, such that a measured CXCL9 level that is lower than the threshold CXCL9 level indicates that the patient is responding positively to the treatment and a measured CXCL9 level that is higher than or equal to the threshold CXCL9 level indicates that the patient is not responding positively to the treatment for PSC.

In certain embodiments, the assay may be used to identify a new treatment for PSC. For example, a method of identifying a new treatment for PSC may include administering a treatment to a subject diagnosed as having PSC and determining CX3CL1, MIP-3β, and/or CXCL9 levels in a body fluid sample of the subject, where a CX3CL1, MIP-3β, and/or CXCL9 level lower than a threshold level indicates that the treatment is effective. In another embodiment, a method of identifying a new treatment for PSC may include administering a treatment to a subject diagnosed as having PSC and determining CX3CL1, MIP-3β, and/or CXCL9 levels in a body fluid sample of the subject over a period of time, where a CX3CL1, MIP-3β, and/or CXCL9 level lower than a baseline level indicates that the treatment is effective. The baseline level may be level obtained prior to or immediately after (day 0, day 1-5) of start of treatment. In other embodiments, a downward trend in levels of CX3CL1, MIP-3β, and/or CXCL9 is indicative of effectiveness of the treatment. Downward trend may be established by comparing a levels of a biomarker measured over a period of time. The levels may be measured at 2, 3, 4, 5, 6, or more points of time after start of the treatment and may optionally include a measurement of the level of the biomarker before the start of the treatment. The experimental treatment may be a treatment currently used for treating other types of ALD or liver diseases in general.

Methods of Diagnosing Relapse of ALD

As noted in the preceding section, methods for identifying patients who have responded positively to a treatment for PBC, AIH, and PSC are disclosed. These methods may identify ALD patients who are in remission. In addition, PSC patients, such as, patients having an advanced stage PSC or having liver failure may be treated by liver transplantation. However, patients who have previously been treated for ALD may relapse and develop an ALD.

Provided herein are methods for monitoring a patient who has been treated for an ALD to determine whether the patient has a relapse of the ALD. As noted in the preceding section, PBC or AIH patients that have responded to treatment and are in remission are identifiable based on levels of the biomarker CX3CL1, MIP-3β, and/or CXCL9, where a level of CX3CL1 lower than a CX3CL1 threshold level and/or a level of MIP-3β lower than a MIP-3β threshold level (and optionally, a level of CXCL9 lower than a threshold CXCL9 level) indicates that the patient is responsive and is in remission. As a corollary, the methods provided herein are also useful for diagnosing relapse of PBC or AIH in a patient previously treated for PBC or AIH, where an increased level of CX3CL1, MIP-3β, and/or CXCL9 compared to respective threshold levels of CX3CL1, MIP-3β, and/or CXCL9 indicates that the patient is suffering from a relapse of the disease. These methods are also useful in detecting relapse of PSC in a patient who has received a liver transplant or another treatment, such as, an experimental treatment or off-label drug, as a treatment for PSC.

In certain embodiments, a method for monitoring relapse of autoimmune liver disease (ALD) in a subject treated for the ALD may include assaying in a body fluid sample of the subject a level of CX3CL1 and/or CCL19, wherein a level of CX3CL1 higher than a threshold level of CX3CL1 and/or a level of CCL19 higher than a threshold level of CCL19, indicates that the subject has a relapse of the ALD. In certain embodiments, the assaying may be performed over an extended period of time after the patient has been treated and CX3CL1 level and/or CCL19 level monitored, where an increase in CX3CL1 and/or CCL19 level over the extended period of time indicates that the subject has relapsed. In other embodiments, in addition to assaying a level of one or both CX3CL1 and CCL19, CXCL9 may also be assayed, where a level of CXCL9 higher than a threshold level of CXCL9 level indicates that the subject has a relapse of the ALD. In certain cases, a method for monitoring relapse of ALD may include assaying in a body fluid sample of the subject a level of (i) CX3CL1; (ii) CCL19; (iii) CX3CL1 and CCL19; (iv) CX3CL1 and CXCL9; (v) CCL19 and CXCL9; (vi) CX3CL1, CXCL9, and CCL19; (vii) CX3CL1 and E3; (viii) CCL19 and E3; (ix) CX3CL1, CXCL9, and E3; or (x) CX3CL1, CXCL9, CCL19, and E3.

In certain embodiments, a level of CX3CL1 in a serum sample of a subject, indicative of relapse of AIH in the subject may be 5000 pg/ml or higher, such as, 6000 pg/ml or higher, 7000 pg/ml or higher, 8000 pg/ml or higher, 9000 pg/ml or higher, 10000 pg/ml or higher, 11000 pg/ml or higher, 12000 pg/ml or higher, 13000 pg/ml or higher, 14000 pg/ml or higher, 15000 pg/ml or higher, e.g., 15000-30000 pg/ml, 18000-30000 pg/ml, or 20000-30000 pg/ml, or higher.

In certain embodiments, a level of CCL19 in a serum sample of a subject, indicative of relapse of AIH in the subject may be 1000 pg/ml or higher, 1100 pg/ml or higher, 1200 pg/ml or higher, 1300 pg/ml or higher, 1400 pg/ml or higher, 1500 pg/ml or higher, 1600 pg/ml or higher, 1700 pg/ml or higher, 2000 pg/ml or higher, e.g., 1500-5000 pg/ml, 3000-5000 pg/ml, or 3000-10000 pg/ml, or higher.

In certain embodiments, a level of CXCL9 in a serum sample of a subject, indicative of relapse of AIH in the subject may be 500 pg/ml or higher, 600 pg/ml or higher, 700 pg/ml or higher, 800 pg/ml or higher, 900 pg/ml or higher, 1000 pg/ml or higher, 2000 pg/ml or higher, 3000 pg/ml or higher, 4000 pg/ml or higher, e.g., 4000-15000 pg/ml, 5000-15000 pg/ml, or 10000-15000 pg/ml, or higher.

In certain embodiments, a level of E3 in a serum sample of a subject, indicative of relapse of AIH in the subject may be 18 pg/ml or higher or 20 pg/ml or higher, e.g., 18-1000 pg/ml.

In certain embodiments, a level of CX3CL1 in a serum sample of a subject, indicative of relapse of PBC or PSC in the subject may be 4500-15000 pg/ml, 6000-13000 pg/ml, or 7000-15000 pg/ml, or higher.

In certain embodiments, a level of CXCL9 in a serum sample of a subject, indicative of relapse of PBC or PSC in the subject may be 1500-5000 pg/ml, 1700-4000 pg/ml, or 2000-400 pg/ml, or higher.

In certain embodiments, a level of CCL19 in a serum sample of a subject, indicative of relapse of PBC or PSC in the subject may be 1000-5000 pg/ml, 1500-5000 pg/ml, 1700-4000 pg/ml, or 2000-400 pg/ml, or higher.

Biomarkers

CX3CL1

C-X3-C Motif Chemokine Ligand (CX3CL1), also known as fractalkine, is a chemokine present in soluble form and membrane bound form. The soluble form is chemotactic for T-cells and monocytes, but not for neutrophils. The membrane-bound form promotes adhesion of those leukocytes to endothelial cells and may play a role in regulating leukocyte adhesion and migration processes at the endothelium. Examples of human CX3CL1 include those comprising an amino acid sequence of Accession No. NP_002987.1. (UniProt Acc. No. P78423) and naturally-occurring variants thereof.

CX3CL1 detection encompasses detection of full-length CX3CL1, as well as detection of naturally-occurring fragments or other metabolites of CX3CL1 found in a biological sample, and detection of fragments or other derivatives generated by manipulation of a biological sample, with the proviso that detection of such fragments, metabolites, or derivatives is specific for detection of CX3CL1. CX3CL1 fragments are usually at least 10, 15, 20, 25, 30, 35, 40, 45, 50, 55, or 60 amino acids or more in length. CX3CL1 may be detected by using an antibody or an antigen-binding fragment thereof that specifically binds to CX3CL1 in a body fluid sample of a human subject. Exemplary antibodies include commercially available anti-CX3CL1 antibody, such as a monoclonal or polyclonal anti-CX3CL1 antibody available from R&D SYSTEMS™, MESO SCALE DISCOVERY™, ORIGENE™, and NOVUS BIOLOGICALS™.

CXCL9

C-X-C motif chemokine 9 (CXCL9), also known as Monokine Induced By Interferon-Gamma (MIG) is a cytokine that affects the growth, movement, or activation state of cells that participate in immune and inflammatory response. CXCL9 is chemotactic for activated T-cells and binds to CXCR3. Examples of human CXCL9 include those comprising an amino acid sequence of Accession No. NP_002407.1 (UniProt Acc. No. Q07325-1); and naturally-occurring variants thereof.

CXCL9 detection encompasses detection of full-length CXCL9, as well as detection of naturally-occurring fragments or other metabolites of CXCL9 found in a biological sample, and detection of fragments or other derivatives generated by manipulation of a biological sample, with the proviso that detection of such fragments, metabolites, or derivatives is specific for detection of CXCL9. CXCL9 fragments are usually at least 10, 15, 20, 25, 30, 35, 40, 45, 50, 55, or 60 amino acids or more in length. CXCL9 may be detected by using an antibody that specifically binds to CXCL9 in a body fluid sample of a human subject. Exemplary antibodies include commercially available anti-CXCL9 antibody, such as a monoclonal or polyclonal anti-CXCL9 antibody available from R&D SYSTEMS™, MESO SCALE DISCOVERY™, ORIGENE™, and NOVUS BIOLOGICALS™.

CCL19

C-C motif chemokine ligand 19 (CCL19), also known as ELC; CKβ11; Macrophage inflammatory protein 3 beta (MIP3(3); MIP-3β; SCYA19 is a ligand for C—C Motif Chemokine Receptor 7 (CCR7). The interaction between CCL19 and CCR7 is essential for the motility of mature DCs and T cells to the lymph nodes, establishment of a close physical contact between them, initiation of a primary immune response and finally proliferation of antigen-specific T cells. Examples of human CCL19 include those comprising an amino acid sequence of UniProt Acc. No. Q99731; and naturally-occurring variants thereof.

CCL19 detection encompasses detection of full-length CCL19, as well as detection of naturally-occurring fragments or other metabolites of CCL19 found in a biological sample, and detection of fragments or other derivatives generated by manipulation of a biological sample, with the proviso that detection of such fragments, metabolites, or derivatives is specific for detection of CCL19. CCL19 fragments are usually at least 10, 15, 20, 25, 30, 35, 40, 45, 50, 55, or 60 amino acids or more in length. CCL19 may be detected by using an antibody that specifically binds to CCL19 in a body fluid sample of a human subject. Exemplary antibodies include commercially available anti-CCL19 antibody, such as a monoclonal or polyclonal anti-CCL19 antibody available from R&D SYSTEMS™, MESO SCALE DISCOVERY™, ORIGENE™, and NOVUS BIOLOGICALS™.

CCL26

"Chemokine, CC Motif, Ligand 26" (CCL26) is also known as "Eotaxin-3" or "E3" and Small Inducible Cytokine Subfamily A, member 26 (SCYA26). E3 is produced as prepolypeptide comprising a signal peptide that is cleaved to generate a mature polypeptide. Examples of human E3 include those comprising an acid sequence of Accession No. AB016542.1; NP_006063; Q9Y258; and BAA84579; and naturally-occurring variants thereof.

E3 detection encompasses detection of full-length E3, as well as detection of naturally-occurring fragments or other metabolites of E3 found in a biological sample, and detection of fragments or other derivatives generated by manipulation of a biological sample, with the proviso that detection of such fragments, metabolites, or derivatives is specific for detection of E3. E3 fragments are usually at least 10, 15, 20, 25, 30, 35, 40, 45, 50, 55, or 60 amino acids or more in length. E3 detection can involve direct detection of E3 or a fragment thereof found in a biological sample, or indirect detection (e.g., by detecting binding of an anti-E3 binding partner, e.g., an anti-E3 antibody).

According to certain embodiments, E3 detection (e.g., serum E3 detection) involves binding of an anti-E3 antibody to E3. Aspects of these embodiments may include binding a detectably-labeled anti-E3 antibody to E3, such that detecting E3 involves detecting the detectable label of the anti-E3 antibody bound to E3. Other aspects of these embodiments may include binding an anti-E3 antibody to E3, followed by binding a detectably-labeled secondary antibody to the anti-E3 antibody, such that detecting E3 involves detecting the detectable label of the secondary antibody. The anti-E3 antibody may be any antibody that specifically binds to E3. According to certain aspects, the anti-E3 antibody is a commercially available anti-E3 antibody, such as a monoclonal or polyclonal anti-E3 antibody available from Abcam®, ABNOVA™, Abgent, Santa Cruz Biotechnology®, United States Biological, PROSCI™, R&D SYSTEMS™, Fitzgerald, MESO SCALE DISCOVERY™, or any other commercially available antibody.

The biomarkers (analytes) used in the methods of the present disclosure, as well as the methods of detection and analysis are described in more detail below.

Subjects

The methods of the present disclosure can be used to facilitate a diagnosis and/or monitoring of severity of an ALD in any suitable subject having or suspected of having an ALD. In certain aspects, the subject has, is suspected of having, or at risk of having, an ALD, and includes subjects having, suspected of having, or at risk of having an ALD such as one or more of AIH, PBC, and PSC. Such subjects include patients undergoing therapy, e.g., undergoing therapy to treat a suspected or diagnosed ALD or undergoing therapy which places the subject at risk of an ALD, e.g., a liver disease of one or more of AIH, PBC and PSC.

According to certain embodiments, subjects to be tested using a method of the present disclosure include individuals who present with or have presented with one or more symptoms of ALD, and includes individuals who present with or have presented with symptoms associated with one or more of AIH, PBC, and PSC, including symptoms of an overlap syndrome of one or more of AIH, PBC, and PSC. Examples of such symptoms include any symptoms indicative of a liver disease such as fatigue, right upper quadrant (RUQ) abdominal pain, nausea, pruritus, jaundice, and/or any abnormal levels of liver enzymes.

Subjects at risk of a liver disease of one or more of AIH, PBC and PSC include those with inflammatory bowel disease (IBD) or a family history of IBD, an autoimmune disease, AIH, PBC, and/or PSC.

A subject can be male or female, and may or may not have any prior history of liver disease. In some instances, the subject may or may not have viral hepatitis (e.g., HCV), or may be suspected of having a viral hepatitis (e.g., HCV). In some instances, the subject has a negative diagnosis for pathogen-induced hepatitis (e.g., a negative diagnosis for viral hepatitis (e.g., hepatitis caused by infection by hepatitis A, B, C, D, or E; Epstein-Barr virus (EBV), cytomegalovirus (CMV)), a negative diagnosis for alcohol-induced liver disease, and/or a negative diagnosis for a drug-induced liver disease.

In certain aspects, the methods of the present disclosure are used to monitor a relapse of ALD (e.g., one or more of AIH, PBC and PSC) in subjects that have previously been treated for the ALD. For example, the methods of the present disclosure may be used to monitor relapse of ALD in a subject who exhibits no apparent clinical symptoms of the ALD (e.g., an apparently healthy subject). Such subjects may exhibit no morbidity at all (e.g., a subject undergoing a routine medical screening (or "check-up")). As such, in certain aspects, the methods find use in monitoring a subject with a relapse of ALD prior to the subject exhibiting any outward manifestations of ALD. In other aspects, the methods of the present disclosure are used to monitor relapse of ALD in a subject who presents with an unspecified morbidity, e.g., a morbidity that may be attributable to a number of etiologies, where liver disease is only one of such etiologies.

In certain embodiments, the subject may have been diagnosed as having ALD, such as, one or more of AIH, PBC, and PSC by using criteria known in the field. For example, the subject may have been diagnosed as having ALD using the methods provided in U.S. Pat. No. 9,535,071, which is herein incorporated by reference in its entirety and particularly for the details of the diagnostic methods disclosed therein.

Biological Samples

Suitable biological samples useful in the methods of the present disclosure include biological fluids (e.g., a blood sample, e.g., whole blood, blood fraction (e.g., serum, plasma)). Where the biological sample is a blood sample, the blood sample can be obtained from fresh blood or stored blood (e.g., in a blood bank). The biological sample can be a blood sample expressly obtained for an assay of the present disclosure or a blood sample obtained for another purpose which can be subsampled for an assay of the present disclosure. Cell free biological fluid samples include serum and plasma.

Samples can be manipulated after or during procurement, such as, by treatment with reagents (e.g., anti-coagulants), dilution, and/or enrichment for certain components for an analyte (s) to be assayed. Samples can be pre-treated as necessary by dilution in an appropriate buffer solution, concentrated if desired, or fractionated by any number of methods including but not limited to ultracentrifugation, fractionation by fast performance liquid chromatography (FPLC), or precipitation. Any of a number of standard aqueous buffer solutions, employing one of a variety of buffers, such as phosphate, Tris, or the like, at physiological pH can be used. In general, after isolation, samples (such as blood samples) are stored at −80° C. until assaying.

Assay Formats and Detection Methods

Biomarkers for analysis in connection with the methods of the present disclosure (e.g., CX3CL1, CXCL9, CCL19, CCL26, etc.) can be detected using a variety of methods, with methods suitable for quantitative and semi-quantitative assays being of particular interest. Examples of detection methods include, but are not limited to, methods for detection of a biomarker polypeptide by binding to a specific binding partner (e.g., antibody) (e.g., ELISA (e.g., non-multiplex, multiplex (e.g., LUMINEX®, MESO DISCOVERY®), flow cytometry and the like), mass spectrometric methods, mass spectrophotometry, HPLC, gas chromatography, cytokine/chemokine arrays (e.g., using cytokine/chemokine binding partners), and the like).

The following are examples of materials and assay formats for use in the methods of the present disclosure.

Methods for Detection of Polypeptides Using Bio Marker Binding Reagents

The methods of the present disclosure can be conducted using binding reagents that bind a biomarker polypeptide, e.g., an anti-biomarker antibody; a binding reagent comprising a ligand-binding portion of a receptor for the biomarker polypeptide, and the like. Where antibodies are used, such methods may be referred to as immunoassays, which, can be conducted in a variety of different formats, some of which are provided below as examples.

The ordinarily skilled artisan will appreciate that any suitable binding reagent can be used in the biomarker polypeptide detection methods of the present disclosure. For example, a binding reagent that comprises a receptor, or at least a ligand-binding portion of a receptor, for a biomarker polypeptide can be used in lieu of an antibody in immunoassays. Receptors and ligand-binding portions of receptors for biomarkers are available and known in the art. For example, a receptor that binds CX3CL1 includes CX3CR1; a receptor that binds CXCL9 includes CXCR3. It should be understood that the biomarker polypeptide detection methods may be described herein with reference to antibodies and "immunoassays", but such references are solely for purposes of brevity and clarity, and is not meant to be limiting.

It will be appreciated that any suitable binding partner can be used in lieu of an antibody in immunological methods available in the art, with the proviso that the assay design is such that the desired specificity of detection of the biomarker is adequately preserved. For example, a binding partner in the form of a receptor or ligand-binding portion thereof can be used as a capture reagent. In such an embodiment, binding of the biomarker to the binding partner can be detected using, for example, an antibody specific for the biomarker to detecting binding partner-biomarker complexes. In another example, a binding partner in the form of a receptor or ligand-binding portion thereof can be used as a detection reagent to detect, for example, biomarker in a complex with a specific anti-biomarker antibody/biomarker complex.

Assays involving use of a biomarker polypeptide and a binding reagent generally involve the detection of binding between a binding reagent (e.g., an anti-biomarker antibody (e.g., an anti-CX3CL1, an anti-CCL19, or anti-CXCL9 antibody that specifically binds its respective target antigen)) and its target biomarker polypeptide (e.g., CX3CL1, CCL19, CXCL9, and CCL26, respectively) in a biological sample obtained from a patient.

Antibodies suitable for use in the methods of the present disclosure in accordance with the methods of the present disclosure include those that bind any suitable region of a biomarker. Antibodies useful in biomarker detection methods can be polyclonal or monoclonal antibodies. For example, assays can use polyclonal antibodies as a capture reagent and monoclonal antibodies as a detection reagent, or vice versa. Antibodies may be of any origin, e.g., mammalian (mouse, goat, rat, and the like), non-mammalian (e.g., avian, e.g., chicken), and may have been produced by any method or combination of methods (e.g., immunization of a host (e.g., a non-human animal), isolation as polyclonal sera, hybridoma-expressing monoclonal antibody, recombination production, and the like).

Assays can be conducted in any of a variety of formats, and may be performed quantitatively or semi-quantitatively. In general, the assay will measure specific binding between a biomarker binding reagent (e.g., an anti-biomarker antibody) and a patient sample by detection of the presence or absence of complex (e.g., an immunocomplex) of the anti-biomarker binding reagent (e.g., antibody) and the biomarker. Examples of immunological methods include, e.g., enzyme-linked immunosorbent assay (ELISA), radioimmunoassay (RIA), and the like. Such immunological methods can be readily adapted for use with a polypeptide comprising at least a ligand binding portion of a biomarker receptor.

Assays can be performed by first immobilizing either proteins from a test sample, or anti-biomarker binding reagents (e.g., anti-biomarker antibodies), on a surface of an insoluble support. Suitable supports are well known in the art and include, for example, immunoaffinity column materials, polystyrene beads, latex beads, magnetic beads, colloid metal particles, glass and/or silicon chips and surfaces, nitrocellulose strips, nylon membranes, wells of assay plate (e.g., multi-well plates), test strips, plastic tubes, etc. An insoluble support can comprise any of a variety of substances, including, e.g., glass, polystyrene, polyvinyl chloride, polypropylene, polyethylene, polycarbonate, dextran, nylon, amylose, natural and modified celluloses, polyacrylamides, and agaroses.

Binding to the support may be accomplished by any suitable means, depending upon the nature of the surface, either directly or indirectly, and may be either covalently or non-covalently bound, e.g., binding by ionic, hydrophobic, and/or covalent interactions. The particular manner of binding is not crucial so long as it is compatible with the reagents and overall detection methods. Where the anti-biomarker binding reagents (e.g., antibodies) are bound to the support and the assay is to detect more than one biomarker in the sample in a single reaction mixture, it may be desirable to bind the binding reagents (e.g., anti-biomarker antibodies) for the different biomarkers to be detected to discrete and separate locations on the support so that the presence or absence of biomarker-binding reagent (e.g., antigen-antibody) complexes at the different locations can be correlated with the presence or absence of the corresponding biomarker in the sample. Assays in which more than one biomarker is detected from the same sample in a single reaction mixture are often referred to as "multiplex assays.

The insoluble supports can be of any suitable material which is readily separated from soluble material, and which is otherwise compatible with the overall method of detecting a biomarker in a sample. The surface of such supports may be solid or porous and of any convenient shape. Examples of suitable insoluble supports to which the receptor is bound include beads, e.g. magnetic beads, latex particles, membranes and microtiter well surfaces.

Before contacting samples or fractions thereof to the assay support, it may be desirable to block non-specific binding sites on the insoluble support so as to reduce non-specific binding of sample or other reaction mixture components to sites on the support not occupied by polypeptide or antibody. Examples of blocking agents include non-interfering proteins such as bovine serum albumin, casein (or other milk proteins), gelatin, and the like. Alternatively, several detergents at non-interfering concentrations, such as Tween, NP40, TX100, and the like may be used. Samples, fractions or aliquots thereof can be added to separate supports or to a single support with discrete, separately assayable locations to which anti-biomarker antibodies or are bound (e.g., as in an array).

The assay can include a series of suitable standards, e.g., a reagent for detection of a biomarker that serves as an internal control (which internal control may be present in the biological sample as obtained from the subject or spiked to include a known amount of the control), a separately assayed sample containing a known concentration of one or more biomarkers, and the like. Controls can be positive controls or negative controls. Where desired, multiple samples and standards can be assayed so that mean values can be obtained for each.

The support having bound test sample (or bound anti-biomarker binding reagents) is incubated with the anti-biomarker binding reagent (or with test sample, where the support has bound anti-biomarker binding reagents) for a time sufficient for formation of specific biomarker-binding reagent complexes (e.g., antigen-antibody complexes). After incubation, the insoluble support can be washed of non-bound components. For example, the support can be washed with a dilute non-ionic detergent medium at an appropriate pH, generally 7-8. Washing can be repeated as desired so as to provide for removal of non-specifically bound proteins to an acceptable level.

After washing, the presence or absence of specific biomarker-binding reagent (e.g., antigen-antibody complexes (also referred to as "specific immunocomplexes" or "specific immune complexes")) is detected. Where the test sample is bound to the support, the presence or absence of specific complexes can be detected directly, e.g., by detection of a detectable label on the anti-biomarker binding reagent. Where the binding reagent is not detectably labeled and the assay involves immobilized test sample, specific complexes can be detected by contacting the sample with a solution containing a detection reagent, e.g., an antibody-specific detection reagent to detect antibody bound to immobilized test protein (e.g., a secondary antibody (i.e., an anti-antibody)). The detection reagent may be any compound that binds a binding reagent (e.g., antibody) with sufficient specificity such that the bound binding reagent is distinguished from other components present. For example, detection reagents can be antibodies specific for the anti-biomarker binding reagent (e.g., biomarker receptor, antibody). Where the detection reagent is an antibody, the antibody may be a monoclonal antibody or polyclonal sera, e.g. goat anti-mouse antibody, rabbit anti-mouse antibody, etc.

The detection reagent can be labeled to facilitate direct, or indirect detection of binding. Suitable detectable labels include any composition detectable by spectroscopic, photochemical, biochemical, immunochemical, electrical, optical or chemical means. Examples include, but are not limited to, magnetic beads, fluorescent dyes (e.g., fluorescein isothiocyanate, texas red, rhodamine, a green fluorescent protein, a red fluorescent protein, a yellow fluorescent protein, and the like), radiolabels (e.g., $^{3}H$, $^{125}I$, $^{35}S$, $^{14}C$, or $^{32}P$), enzymes (e.g., horse radish peroxidase, alkaline phosphatase, luciferase, and others commonly used in an enzyme-linked immunosorbent assay (ELISA)), and colorimetric labels such as colloidal gold or colored glass or plastic (e.g. multistyrene, multipropylene, latex, etc.) beads. Examples of labels which permit indirect measurement of binding include enzymes where the substrate may provide for a colored or fluorescent product. For example, the detection reagent can be an antibody labeled with a covalently bound enzyme capable of providing a detectable product signal after addition of suitable substrate. Examples of suitable enzymes for use in conjugates include horseradish peroxidase, alkaline phosphatase, maleate dehydrogenase and the like. Where not commercially available, such antibody-enzyme conjugates are readily produced by techniques known to those skilled in the art.

Alternatively, the detection reagent may be unlabeled. In this case, a labeled second detection reagent specific for the first detection reagent is used, where the second detection reagent can be labeled in any of the above manners. Such compounds can be selected such that multiple compounds bind each molecule of bound second receptor. Examples of second detection reagent/first detection reagent-specific pairs include antibody/anti-antibody and avidin (or streptavidin)/biotin. Since the resultant signal is thus amplified, this technique may find particular use where only a small amount of biomarker may be present, or where the background measurement (e.g., non-specific binding) is unacceptably high. An example is the use of a labeled antibody specific to the first detection reagent.

Where the anti-biomarker binding reagent (e.g., antibody) is bound to the support, formation of specific complexes can be accomplished using an antibody to detect the presence or absence of specific biomarker-binding reagent complexes. The detection antibody can be the same or different from the bound antibody, with the proviso that the epitopes to which the detection antibody binds are available for detection antibody binding when the biomarker is in the complex with the bound anti-biomarker binding reagent. As described above, the detection antibody can be labeled or unlabeled, and the formation of specific complexes of bound anti-biomarker binding reagent-biomarker-detection antibody detected directly (e.g., by virtue of the detectable label on the detection antibody) or indirectly (e.g., by use of a third reagent that detects the detection antibody in the complex).

After incubation with the reagents for a time sufficient to allow binding of specific complexes, the insoluble support can again be washed to reduce non-specifically bound detection reagent(s). After washing, the signal produced by the bound conjugate is detected by any suitable means compatible with the assay format. For example, where an enzyme conjugate is used, an appropriate enzyme substrate is provided so a detectable product is formed. For example, where the detection involves peroxidase in an enzyme conjugate, the substrate is usually a combination of hydrogen peroxide and O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art.

The presence or absence binding of anti-biomarker binding reagent (e.g., antibody) binding may be determined by various methods that are compatible with the detectable label used, e.g., microscopy, radiography, scintillation counting, etc. A level of specific binding reagent-biomarker complexes may be compared to a level of one or more control samples, and the results evaluated to facilitate a conclusion. Control samples can be run in parallel to provide comparison levels, or the levels of specific complexes in a control level provided as standard values for purposes of comparison.

The assays described here can take a variety of forms. Exemplary formats include, but are not limited to, competitive binding assays, in which formation of complexes is performed in the presence of different amounts of a competitor protein which competes for binding to the anti-biomarker binding reagent (e.g., antibody). The competitor molecule can be labeled and detected as previously described, where a decrease in competitor binding will be proportional to the level of biomarker present in the sample.

The detection assays can be carried out in solution. For example, the anti-biomarker antibody(ies) can be combined with the test sample (e.g., serum or any other test sample of interest), and immune complexes of anti-biomarker antibody (ies) and biomarker(s) are detected.

Mass Spectrometric Methods

The methods of the present disclosure can be accomplished by other detection techniques. For example, mass spectrometric assays can be adapted for detection of biomarker(s) in a biological sample. Mass spectrometry-based methods exploit the differences in mass of biomarkers to facilitate detection. Mass spectrometry can be combined with immunoassays, e.g., by first forming specific biomarker-antibody immunocomplexes, and detecting the presence or absence of the specific immunocomplexes by mass spectroscopy. For example, an anti-biomarker antibody can be used to capture the biomarker of interest (e.g., CX3CL1 and/or CXCL9). The anti-biomarker antibody can be bound to a support, such as a bead, a plate, a membrane or a chip. After unbound materials are washed away, the captured biomarkers can be detected by mass spectrometry. Examples of mass spectrometers are time-of-flight, magnetic sector, quadrupole filter, ion trap, ion cyclotron resonance, electrostatic sector analyzer and hybrids of these.

Analysis of mass spectrometry data can be accomplished by available methods. For example, assaying of analytes by time-of-flight mass spectrometry generates a time-of-flight ("TOF") spectrum. The TOF spectrum ultimately analyzed typically generally does not represent the signal from a single pulse of ionizing energy against a sample, but rather the sum of signals from a number of pulses. This reduces noise and increases dynamic range. This TOF data can then be subjected to data processing. For example, in Ciphergen's PROTEINCHIP® software, data processing typically includes TOF-to-M/Z transformation to generate a mass spectrum, baseline subtraction to eliminate instrument offsets and high frequency noise filtering to reduce high frequency noise.

Data generated by mass spectrometry methods can be analyzed with the use of a programmable computer. The computer program executes a program to analyze the data to indicate the number of biomarkers detected, and the strength of the signal (indicative of the amount of the biomarker), and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's PROTEINCHIP® software package, that can automate the detection of peaks. In general, this software functions by identifying signals having a signal-to-noise ratio above a selected threshold and labeling the mass of the peak at the centroid of the peak signal. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

Compositions

The present disclosure provides compositions that find use, e.g., in practicing the methods of the present disclosure. In certain aspects, the compositions include an agent for detecting a biomarker of interest (e.g., CX3CL1 and/or CCL19 and/or CXCL9 and/or CCL26 detection agent). With respect to CX3CL1, for example, the detection agent may be any agent useful for detecting CX3CL1 in a sample of interest (e.g., a serum sample of a subject), including but not limited to, an anti-CX3CL1 antibody, or the like. In addition to CX3CL1 and/or CCL19 and/or CXCL9 detection agent, compositions of the present disclosure may include one or more detection agents useful for detecting one or more additional biomarkers of interest. Such additional detection agents may include, but are not limited to, one or more agents (e.g., an antibody or primer pair) for detecting eotaxin-1 (E1), macrophage-derived chemokine (MDC), interleukin-15 (IL-15), alkaline phosphatase (AP), or any combination thereof. For example, the compositions may include an E3 detection agent and an E1 detection agent; or an E3 detection agent, an E1 detection agent, and an MDC detection agent; or an E3 detection agent, an E1 detection agent, an MDC detection agent, and an IL-15 detection agent; or an E3 detection agent, an E1 detection agent, an MDC detection agent, an IL-15 detection agent, and an AP detection agent. Such compositions may be used for diagnosing presence of ALD as well as diagnosing the severity (e.g., stage) of the disease.

According to certain embodiments, the composition does not include any detection agents other than, optionally, a detection agent for detecting a control (e.g., "housekeeping") protein to facilitate and control for quantitation of biomarker signals in addition to: CX3CL1 and/or CXCL9 detection agent, an E3 detection agent; or an E3 detection agent and an E1 detection agent; or an E3 detection agent, an E1 detection agent, and an MDC detection agent; or an E3 detection agent, an E1 detection agent, an MDC detection agent, and an IL-15 detection agent; or an E3 detection agent, an E1 detection agent, an MDC detection agent, an IL-15 detection agent, and an AP detection agent.

The compositions of the present disclosure may include a biological sample from a subject (e.g., a subject suspected of having liver disease, an apparently healthy subject undergoing routine medical screening, a subject with an unspecified morbidity under investigation, a control subject, or other subject) or a control sample (e.g., serum, buffer, or the like in which one or more biomarkers of interest are present (e.g., added) for purposes of providing a control (e.g., a benchmark control that includes serum from a healthy individual spiked with each of the biomarkers to be detected in the assay) for the assay). For example, in certain aspects, the compositions include an CX3CL1 and/or CCL19 and/or CXCL9 detection agent (e.g., an anti-CX3CL1 antibody) and a serum sample, a plasma sample, or a whole blood sample from a subject suspected of having or having liver disease, e.g., a disease such as autoimmune hepatitis (AIH), primary sclerosing cholangitis (PSC), primary biliary cirrhosis (PBC), or any combination thereof. As described above, the compositions may further include one or more agents for detecting additional biomarkers of interest, such as detection agents useful for detecting E1, MDC, IL-15, AP, or any combination thereof.

In certain aspects, the compositions of the present disclosure are present in a container, such as a storage container and/or assay container. The container may be any convenient container suitable for, e.g., storing a CX3CL1 detection agent (e.g., in combination with one or more detection agents for detecting CXCL9, CCL19, E1, MDC, IL-15, AP, or any combination thereof), or carrying out a detection assay (e.g., a solution- or solid phase-based assay) for detecting CX3CL1 and any additional biomarker(s) of interest, such as CXCL9, CCL19, E1, MDC, IL-15, AP, or any combination thereof. Containers of interest include a tube, e.g., a tube of any convenient size (e.g., ranging from 0.2 ml to 15 ml, such as 0.2 ml, 0.5 ml, 1.0 ml, 1.5 ml, 2.0 ml, 5 ml, 10 ml, 15 ml or the like) and material (e.g., polypropylene, or any other material suitable for storing or using the composition). In certain aspects, the composition is present in a container that is a series of tubes, such as a one- or two-dimensional array of tubes (e.g., a strip of tubes, or tubes in a "plate" format, such as a 24-well, 48-well, 96-well, 384-well, or other convenient plate format).

According to certain embodiments, the composition is disposed on a planar substrate (e.g., the bottom of a well, array, chip (e.g., microfluidic chip), and/or the like). When the composition is disposed on a substrate, any detection agents present in the composition (e.g., a CX3CL1 detection agent, optionally in combination with a CCL19 and/or a CXCL9 detection agent) may be present in a solution or suspension disposed on the substrate, or alternatively, may be attached to the substrate, e.g., directly attached to the surface of the substrate, or attached via a linker moiety (e.g., an antibody (such as an anti-species antibody) or other suitable linker moiety). Such compositions find use, for example, in performing solid phase assays (e.g., ELISA-based or non-enzyme-based solid phase protein detection assays, solid-phase nucleic acid amplification, or the like) for detecting one or more biomarkers of interest.

Computer-Implemented Methods, Systems and Devices

The methods of the present disclosure can be computer-implemented, such that method steps (e.g., assaying, comparing, calculating, and/or the like) are automated in whole or in part. Accordingly, the present disclosure provides methods, computer systems, devices and the like in connection with computer-implemented methods of facilitating a diagnosis of severity of at least one of AIH, PBC, and PSC; relapse of at least one of AIH, PBC, and PSC; or remission of at least one of AIH, PBC, and PSC.

For example, the method steps, including obtaining values for biomarker levels, comparing biomarker levels to a control level, generating a report, and the like, can be completely or partially performed by a computer program product. Values obtained can be stored electronically, e.g., in a database, and can be subjected to an algorithm executed by a programmed computer.

For example, the methods of the present disclosure can involve inputting a biomarker level into a computer programmed to execute an algorithm to perform the comparing and calculating step(s) described herein, and generate a report as described herein, e.g., by displaying or printing a report to an output device at a location local or remote to the computer.

The present invention thus provides a computer program product including a computer readable storage medium having a computer program stored on it. In certain aspects, the storage medium is non-transitory (e.g., a storage medium that is not a transitory wave or signal). The program can, when read by a computer, execute relevant calculations based on values obtained from analysis of one or more biological sample from an individual. The computer program product has stored therein a computer program for performing the calculation(s).

The present disclosure provides systems for executing the program described above, which system generally includes: a) a central computing environment; b) an input device, operatively connected to the computing environment, to receive patient data, wherein the patient data can include, for example, biomarker level or other value obtained from an assay using a biological sample from the patient, as described above; c) an output device, connected to the computing environment, to provide information to a user (e.g., medical personnel); and d) an algorithm executed by the central computing environment (e.g., a processor), where the algorithm is executed based on the data received by the input device, and wherein the algorithm calculates a value, which value is indicative of the likelihood the subject has a condition as described herein.

Embodiments may be described in a general context of computer-executable instructions, such as program modules, being executed by a computer. Generally, program modules include routines, programs, objects, components, data structures, etc., that perform particular tasks or implement particular abstract data types. An embodiment may also be practiced in a distributed computing environment where tasks are performed by remote processing devices that are linked through a communications network. In a distributed computing environment, program modules may be located in both local and remote computer storage media (e.g., non-transitory storage media, where the medium is not a transitory wave or signal) including memory storage devices.

The present disclosure provides computer program products that, when executed on a programmable computer such as that described above can carry out the methods of the present disclosure. As discussed above, the subject matter described herein may be embodied in systems, apparatus, methods, and/or articles depending on the desired configuration. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g. video camera, microphone, joystick, keyboard, and/or mouse), and at least one output device (e.g. display monitor, printer, etc.).

Examples of Applications of Method Results

The methods of the present disclosure can provide results which can then be applied to facilitate decisions as to the care of the subject. Examples are provided below.

Assay-Guided Therapy

The methods of the present disclosure can facilitate a clinician in making a treatment decision for the subject, e.g., whether the results of the method suggest the subject may or may not benefit from therapeutic intervention for treatment of ALD such as, AIH, PSC, or PBC. For example, based on the method results, a therapy can be selected for the subject based on the likelihood s/he has or is at risk of an advanced stage ALD.

In addition, methods for assessing severity or extent of progression of ALD can be used for monitoring a subject over time and adjusting treatment and/or prioritizing the subject for liver transplant.

Methods for assessing severity or extent of progression of ALD as disclosed herein can be combined with other methods currently used to monitor ALD severity. In certain aspects, methods for assessing severity or extent of progression of ALD may further include using elastography to determine extent of liver fibrosis; using levels of alanine transaminase (ALT), aspartate transaminase (AST), and gamma globulin (IgG); or using alkaline phosphatase, gamma-glutamyl transferase (GGT), and bilirubin levels to determine disease severity.

In certain aspects, the method of determining presence of advanced stage AIH (e.g., assaying level of CX3CL1) can be combined with measuring levels of alanine transaminase (ALT), aspartate transaminase (AST), and gamma globulin (IgG).

In certain aspects, the method of determining presence of advanced stage PSC or PBC (e.g., assaying level of CX3CL1) can be combined with measuring levels of alkaline phosphatase, gamma-glutamyl transferase (GGT), and bilirubin levels.

The method results can guide a clinician as to whether or not any therapy for treatment of an advanced stage ALD should be administered. For example, a subject diagnosed as having an advanced stage ALD may be prioritized for liver transplant. A subject diagnosed as having an advanced stage ALD may be treated with a higher dose of immunosuppressive therapy or may be treated with a combination therapy.

In certain aspects, the method results can guide a clinician in adjusting therapy (e.g., whether or not to continue therapy (e.g., so as to avoid relapse), increase or decrease dose, change therapy regimen (e.g., from monotherapy to combination therapy, or from non-surgical therapy to surgical therapy) where the patient is not receiving adequate therapeutic benefit (e.g., the patient is not responding to therapy), and the like). Such methods of monitoring therapy are useful in guiding further treatment decisions, such as whether continued administration of a drug regimen indicated, or whether the patient should receive a liver transplant. The methods of monitoring therapy of the present disclosure may be used in combination with other methods for assessing whether a subject responds to therapy (is a "responder") or is not exhibiting a sufficient therapeutically beneficial response (is as "nonresponder").

The methods of the present disclosure can be useful in selecting therapy where a diagnosis of PBC is indicated. The standard of care for PBC is administration of UDCA. Liver transplantation is indicated where the subject is at risk of liver failure. The methods of the present disclosure may be used to monitor efficacy of a non-surgical therapy (e.g., UDCA) for a PBC patient. Where a diagnosis of PBC persists, the clinician may be guided to modify therapy (e.g., dose, dosage, and/or type of therapy, e.g., combination therapy versus monotherapy), including making a decision to treat the patient surgically.

The methods of the present disclosure can be useful in selecting therapy where a diagnosis of PSC is indicated. Currently, there are no available non-surgical curative therapies that have proven effective, at least in part due to the lack of therapeutic endpoints. Thus, where a diagnosis of PSC is indicated, the clinician may be guided to treat the patient surgically, depending on other factors, such as the severity of other patient signs and symptoms. In general, so long as a PSC patient has a functional liver, palliative and symptomatic therapies are may be administered, including antibiotic therapies and palliative surgical biliary drainage, endoscopic dilatation and stenting. Alternatively or in addition, the clinician may elect to treat the patient non-surgically and monitor efficacy of therapy using the methods of the present disclosure. Non-surgical therapies may include administration of UDCA, cholestyramine, and/or hydroxyzine HCL for alleviation of symptoms (e.g., pruritus). Administration of antibiotics may be indicated where infectious cholangitis is suspected. However, should the disease progress such that the patient is at risk of liver failure, liver transplantation is indicated. Alternatively, prior to resorting to liver transplantation, the patient may be offered experimental treatment such as off-label use of a drug.

In AIH, immunosuppressive agents such as corticosteroids (e.g., prednisone or prednisolone) with or without azathioprine can be administered to control the disease. In cases without liver cirrhosis the topical steroid budesonide can be administered. Because of the side effects associated with immunosuppressive treatments, a firm diagnosis of advanced stage or relapse before treatment is started would be desirable. About 40% of patients achieve complete remission meaning normal serum transaminases (ALT and AST) and normal IgG levels between months 6 and 12. A therapeutic challenge are the so called AIH non-responders to standard of care with predniso(lo)ne plus minus azathioprine. Treatment has to be continued in remission at least 2-3 years and liver biopsy has to be performed to confirm lack of disease activity by histopathology; otherwise patients will relapse after cessation of treatment. Up to 80% of patients experience relapse and then immunosuppressive treatment has to be started again. Thus, the methods of the present disclosure can find use in monitoring response to therapy and reduce risk of relapse and/or detect relapse at an earlier stage. If a patient is at risk of relapse as indicated by use of the methods disclosed herein, the clinician may be guided to reinitiate therapy, and may indicate surgical intervention (e.g., liver transplant).

In addition, the present methods are useful in providing reports to clinicians with information such as presence of an advanced stage of disease of AIH, PBC, and/or PSC; positive response or lack of response to therapy; and/or relapse of the disease after treatment.

Reports can include guidance to a clinician as to a treatment recommendation for the subject based on the likelihood of the presence of an advanced stage liver disease of at least one of AIH, PBC, and PSC. For example, reports can include a recommendation regarding further evaluation and/or avoiding expensive and invasive evaluations and/or a recommendation regarding therapeutic intervention (e.g., administering a drug, recommending surgical intervention, etc.), modifying a treatment regimen (e.g., adjusting a drug dose (e.g., increasing or decreasing a dose), adjusting a dosage regimen (e.g., increasing or decreasing dose frequency and/or amount), and the like.

A report can further include one or more of: 1) patient information (e.g., name, medical information (e.g., age, gender, symptoms (e.g., symptoms that may be relevant to diagnosis of an inflammatory liver disease), viral infection status (e.g., presence/absence of viral hepatitis), etc.), 2) information about the biological sample (e.g., type, when obtained); 3) information regarding where and how the assay was performed (e.g., testing facility, assay format); 4) service provider information; and/or 5) an interpretive report, which can provide a narrative providing an at least partial interpretation of the results so as to facilitate clinical decisions by a clinician. In certain embodiments, the report may indicate that the patient's condition is worsening and may recommend a follow up liver biopsy as a confirmatory test. A positive confirmatory test may lead to assignment of a higher priority for receiving a liver transplant.

Accordingly, the methods disclosed herein can further include a step of generating or outputting a report providing the method results and, optionally, other information such as treatment guidance as described herein. The report can be provided in the form of an electronic medium (e.g., an electronic display on a computer monitor), or in the form of a tangible medium (e.g., a report printed on paper or other tangible medium). An assessment as to the likelihood can be referred to as "risk report" or, simply, a "diagnostic result". The person or entity that prepares a report ("report generator") may also perform steps such as sample gathering, sample processing, and the like. Alternatively, an entity other than the report generator can perform steps such as sample gathering, sample processing, and the like. A report can be provided to a user. A "user" can be, for example, a health professional (e.g., a clinician, a laboratory technician, a physician, etc.).

Treatment of ALD

The present disclosure provides methods of treating AIH, PBC and PSC by administering to a subject in need thereof an effective amount of an antagonist of CCL19, CX3CL1, and/or CXCL9 activity. Also provided are methods of treating PSC by administering to a subject in need thereof an effective amount of an antagonist of CCL19 activity (optionally in combination with an antagonist of CX3CL1, CXCL9, and/or E3 activity).

"Antagonist" as used herein refers to a drug (e.g., antibody) that reduces or blocks activity of its target. An antagonist may reduce activity of its target directly or indirectly. For example, an antagonist of CCL19 activity may reduce CCL19 activity by reducing CCL19 levels available for binding to its receptor or by reducing availability of the receptor. Representative antagonists, include, but are not limited to, antibodies (including antigen-binding antibodies), nucleic acids (e.g., antisense molecules, such as ribozymes and RNA interfering agents), immunoconjugates (e.g., an antibody conjugated to a therapeutic agent), small molecule drug inhibitors, fusion proteins, aptamers, and the like. Reduction of activity of a target (e.g., CCL19) can be accomplished by, for example, reducing an amount of active target present in the bloodstream of a subject or an CCL19-producing tissue of the subject, and/or reducing activity of the target, e.g., by reducing availability of the CCL19 receptor, CCR7.

In one embodiment, the antagonist is an antibody or an antigen-binding fragment of an antibody that specifically binds and blocks the action of CCL19. Such an antibody may be anti-CCL19 antibody or anti-CCR7 antibody.

In another embodiment, the antagonist is a small molecule. As used herein, "small molecule" refers to synthetic chemical molecules that are less than about 1000 daltons in molecular weight, such as less than 750 daltons, including molecules less than 700 daltons, and inhibit activity of the chemokine (e.g., CCL19).

In another embodiment, the antagonist is an antisense nucleic acid molecule (e.g., an antisense RNA, silencing RNA (siRNA), short hairpin RNA (shRNA), microRNA (miRNA), or other nucleic acid molecule of interest) that is complementary to a mRNA encoding the chemokine (e.g., CCL19), or to a portion of that mRNA, or a recombinant expression vector encoding such a nucleic acid molecule. As used herein, an "antisense" RNA, siRNA, shRNA or miRNA nucleic acid comprises a nucleotide sequence specific to the gene and/or mRNA encoding the chemokine (e.g., CCL19).

Antisense nucleic acids can be designed according to the rules of Watson and Crick base pairing. The antisense nucleic acid molecule can be complementary to the entire coding region of the chemokine (e.g., CCL19) mRNA, or to only a portion of the coding or noncoding region of the chemokine (e.g., CCL19) mRNA. For example, the antisense oligonucleotide can be complementary to the region surrounding the translation start site of the chemokine (e.g., CCL19) mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Antisense nucleic acid can be produced biologically using an expression vector into which a nucleic acid has been subcloned in an antisense orientation, e.g., such that RNA transcribed from the inserted nucleic acid will be if an antisense orientation to a target nucleic acid of interest.

The antagonists of the chemokine (e.g., CCL19) include RNA interfering agents (RNAi), which include, but are not limited to, nucleic acid molecules including RNA molecules which are homologous to the chemokine (e.g., CCL19), "short interfering RNA" (siRNA), "short hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA.

In general, the methods of treatment involve identifying a subject as having one or more of AIH, PBC, or PSC, and administering an amount of an antagonist CCL19 activity, an antagonist of CX3CL1 activity, or both, effective to provide a therapeutic benefit in the patient. "Therapeutic benefit", "treat", "treatment" includes at least reduction the severity of, or amelioration of one or more symptoms of a disease. For example, the antagonist may be used to reduce liver inflammation, reduce liver fibrosis, reduce liver cirrhosis, and/or increase liver function, etc. Therapy can optionally be combined with other therapy for AIH, PBC or PSC, as appropriate. Antagonist(s) of CCL19, CX3CL1, Eotaxin-3, and CXCL9 activity can be administered by any appropriate route, which may be selected according to the agent to be administered. Administration is normally parenteral, and includes injection by an intravenous routes as well as injection into tissue, e.g., involved liver tissue of the subject. In one embodiment, the antagonists CCL19, CX3CL1, Eotaxin-3, and/or CXCL9 activity are administered by intravenous infusion, and may be administered by injection for delivery to liver (e.g., via a hepatic artery).

In certain aspects, the antagonists (e.g., anti-CCL19 antibody) described herein may be present in a pharmaceutical composition comprising a pharmaceutically acceptable excipient. In certain aspects, antagonists (e.g., anti-CCL19 antibody) are present in a therapeutically effective amount in the pharmaceutical composition. A therapeutically effective amount can be determined based on an observed effectiveness of the composition.

The pharmaceutical compositions of the present disclosure can be formulated to be compatible with the intended method or route of administration; exemplary routes of administration are set forth herein. Suitable pharmaceutically acceptable or physiologically acceptable diluents, carriers or excipients include, but are not limited to, nuclease inhibitors, protease inhibitors, a suitable vehicle such as physiological saline solution or citrate buffered saline.

In certain aspects, the antibody or an antigen binding fragment thereof used for antagonizing a biological marker of AIH as disclosed herein may be a chimeric antibody, a humanized antibody or a human antibody.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Materials and Methods

Cohort: The serum samples from PBC, PSC, and AIH patients along with controls were evaluated for the levels of different cytokines/chemokines using multiplex ELISA technology. The pre-coated ELISA kits from MESO SCALE DISCOVERY™ (MSD, Gaithersburg, MA, USA) were used. That includes Chemokine Panel 1, Cytokine Panel 1, and Proinflammatory Panel 1 Human V-PLEX Plus Kits along with Human Eotaxin-2 Kit, and a custom-designed 3-Plex kit. All experiments were performed according to the manufacturer's instruction with minimal modifications and optimization and the MSD electrochemiluminescence detection system was used for reading the signals. Briefly, 50 μl of each 1:2 diluted sample and controls was added to each well of the 96-well plate along with standards and incubated for 2 h 30 min with continuous automatic shaking at room temperature (RT). The plates were then washed three times with 1× Wash Buffer (MSD), and Sulfotag Detection Antibody Cocktail (MSD) was added to each well, and the plates were incubated for additional 2 h with shaking at RT. Finally, the plates were washed for three times and were scanned by a SECTOR® Imager 6000 Reader (MSD), after adding 150 μl of 2× Read Buffer (MSD), followed by a blind analysis and validation of data. The obtained concentrations were corrected for dilution and then the values were compared between healthy individuals and patients.

Statistical Analysis: For the standard curves, a four-point logarithmic curve was used based on a commonly accepted method of "Fit-for-Purpose Method Development and Validation for Successful Biomarker Measurement" (Lee, J. W., et al., Pharm Res, 2006. 23(2): p. 312-28). To measure the inter-assay (-plate) coefficient variance (Inter-CV) in order to properly compare collected date form different plates, we added four control samples on each plate that were set at different levels of concentration on standard (STD) curves. Intra-assay (Intra)-CVs were calculated for each plate and the average of all plates are reported for each analyte. Lower level of detection (LLOD) was calculated based on the limit of blank and was set at 2.5 standard deviation (SD) above the blank. Lower level of quantification (LLOQ) was the lowest standard point that its mean recovery value was within the 20% of the actual value (accuracy of 20%) and a CV of 20% (precision of 20%) for that point. Signal analysis was also done to confirm that the calculated concentration for each cytokine and chemokine is compatible with the actual signal that is reported by the scanner to rule-out any matrix effect related to the samples.

The final calculated concentrations from both healthy and patient groups were analyzed using statistical software (GRAPHPAD PRISM™ Version 6.00, Prism Software Corporation, Irvine, CA, USA). As data points from each group appeared to not be normally distributed, the median values between pairs of groups were compared using the Mann-Whitney U test. Differences were considered significant if the two-tailed P value was lower than 0.05.

Example 1: CX3CL1 is an Indicator of Disease Severity in PBC and PSC

In non-autoimmune liver diseases fibrosis is typically monitored using transient elastography (i.e. Fibroscan). Elastography is a technique that can be used to determine the stiffness of tissue using an ultrasound device. Tissue stiffness, in the liver, generally corresponds with the degree of fibrosis, but it is significantly influenced by the necro-inflammation (Coco, B., et al., J Viral Hepat, 2007. 14(5): p. 360-9), which is a typical feature of autoimmune liver disease. Thus, data on fibrosis quantification and cirrhosis with Fibroscan in autoimmune liver disease has remained scarce (Sclair, S. N., et al., Clin Transl Gastroenterol, 2015. 6: p. e109), because using this method to evaluate disease progression might lead to false conclusions.

In AIH, the level of alanine transaminase (ALT), aspartate transaminase (AST), and gamma globulin (IgG) may be used to evaluate the disease severity and to monitor the treatment, by determining if disease is in remission or relapse state (Manns, M. P., et al., Hepatology, 2010. 51(6): p. 2193-213). However, normalization of serum levels of transaminases does not warrant remission of liver disease at histology, and 15-25% of cases (particularly children and elderlies) have normal IgG at baseline (Zachou, K., et al., Aliment Pharmacol Ther, 2013. 38(8): p. 887-913; Gatselis, N. K., et al., World J Gastroenterol, 2015. 21(1): p. 60-83).

Alkaline phosphatase, gamma-glutamyl transferase (GGT), and bilirubin levels are currently used to predict disease progression for PSC and PBC patients. However, their predictive capacity is controversial (Poordad, F., Gastroenterol Hepatol (N Y), 2016. 12(9): p. 561-564). The level of ALP and GGT are currently used to evaluate the severity of diseases and to monitor the treatment (in case of PBC) by showing if disease is in remission or relapse state, however their levels do not correlate with the fibrosis stage (Joshi, S., et al., Hepatology, 2002. 35(2): p. 409-13).

PSC can also be monitored by endoscopic retrograde cholangiopancreatographies (ERCP) or Magnetic resonance cholangiopancreatographies (MRCP) that permit visualization of the bile ducts, where the progressive narrowing of the ducts correlates with progression of disease. Unfortunately, these techniques are expensive and, in the case of ERCP, invasive. Therefore, it is recommended that only one per year be performed (Lindor, K. D., et al., Am J Gastroenterol, 2015. 110(5): p. 646-59; quiz 660).

Liver biopsies can accurately indicate cirrhosis, but they are invasive and unsuitable for frequent monitoring.

Figure 1B:
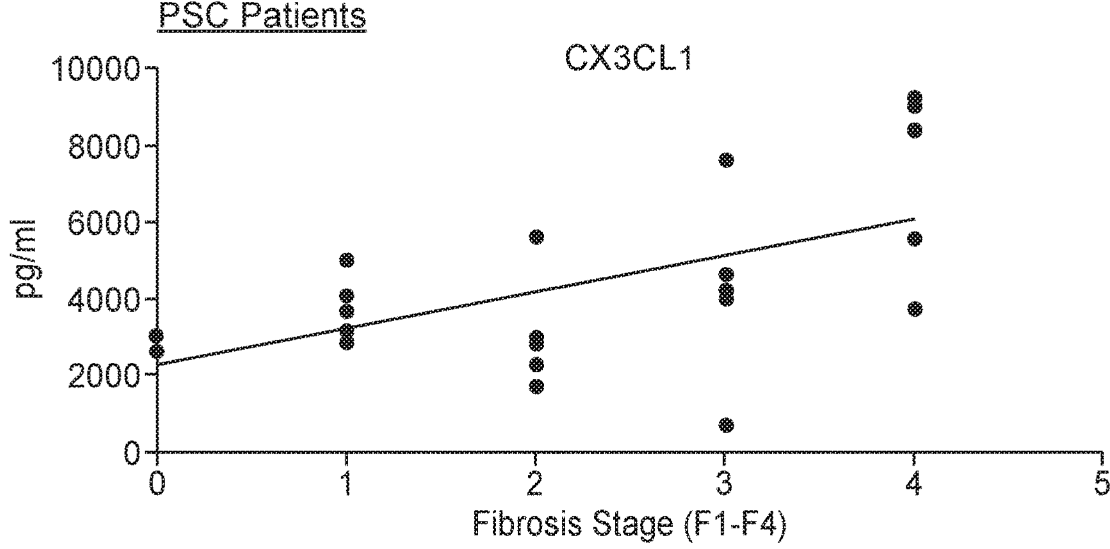
FIG. 1B. CX3CL1 (fractalkine) levels have a highly significant moderate correlation with fibrosis stage in PSC patients.

Data provided here shows that CX3CL1 levels measured in plasma samples from PSC and PBC patients have a highly significant correlation with fibrosis (FIGS. 1A, 1B). Moreover, CX3CL1 levels are significantly higher in PSC and PBC patients with cirrhosis compared to non-cirrhotic patients (FIGS. 2A, 2B) and PSC with decompensated cirrhosis had significantly higher CX3CL1 levels compared to non-decompensated patients (FIG. 3).

Based on the data on CX3CL1 in PBC and PSC patients, cut-offs were defined that discriminate patients with advanced liver fibrosis, cirrhosis, and/or decompensated cirrhosis from patients with milder conditions.

PBC

If CX3CL1 levels were greater than or equal to 5000 pg/ml, then 50% of PBC patient with stage F4 fibrosis would be detected (5 out of 10 PBC cases with F4 fibrosis=sensitivity of 50%). This cut-off gives a specificity of 98%, since only 1 patient out of 41 PBC patients with fibrosis stage of less than F4 showed a CX3CL1 level greater than or equal to 5000 pg/ml.

If CX3CL1 levels were greater or equal to 5000 pg/ml, then 26% of PBC patients with cirrhosis are picked up (6 patients out of 21 cirrhotic patients=sensitivity of 26%). In this case, the specificity was 100% as none of the 28 patients without cirrhosis had a CX3CL1 level that was higher than or equal to 5000 pg/ml.

PSC

If CX3CL1 levels were greater or equal to 5000 pg/ml, then 52% of PSC patients with cirrhosis are picked up (11 patients out of 21 cirrhotic patients=sensitivity of 52%). In this case, the specificity was 94% as only 2 of the 33 patients without cirrhosis had a CX3CL1 level that was higher than or equal to 5000 pg/ml.

When the cut-off was set to a higher level (5700 pg/ml), then the sensitivity reduced to 33% (7 patients out of 21), while the specificity increased to 100% (0 patient out of 33 PSC patients without cirrhosis).

If CX3CL1 levels were greater or equal to 5000 pg/ml, then 67% of PSC patients with decompensated cirrhosis could be detected (10 patients out of 15 with decompensated cirrhosis=sensitivity of 67%). In this case, the specificity was 92% as only 3 of the 39 patients without decompensated cirrhosis had a CX3CL1 level that was higher than or equal to 5000 pg/ml.

By setting cut-off to 5700 pg/ml, the sensitivity reduced to 47% (7 patients out of 15), while the specificity increased to 100% (0 patient out of 39 PSC patients without decompensated cirrhosis).

If CX3CL1 levels were greater than or equal to 8000 pg/ml, then 60% of PSC patient with stage F4 fibrosis would be detected (3 out of 5 PSC cases with F4 fibrosis=sensitivity of 60%). This cut-off gives a specificity of 100%, since no patient out of 20 PSC patients with fibrosis stage of less than F4 showed a CX3CL1 level greater than or equal to 8000 pg/ml.

FIG. 1A. CX3CL1 (fractalkine) levels have a highly significant moderate correlation with fibrosis stage in PBC.

FIG. 1B. CX3CL1 (fractalkine) levels have a highly significant moderate correlation with fibrosis stage in PSC patients.

Figure 2A:
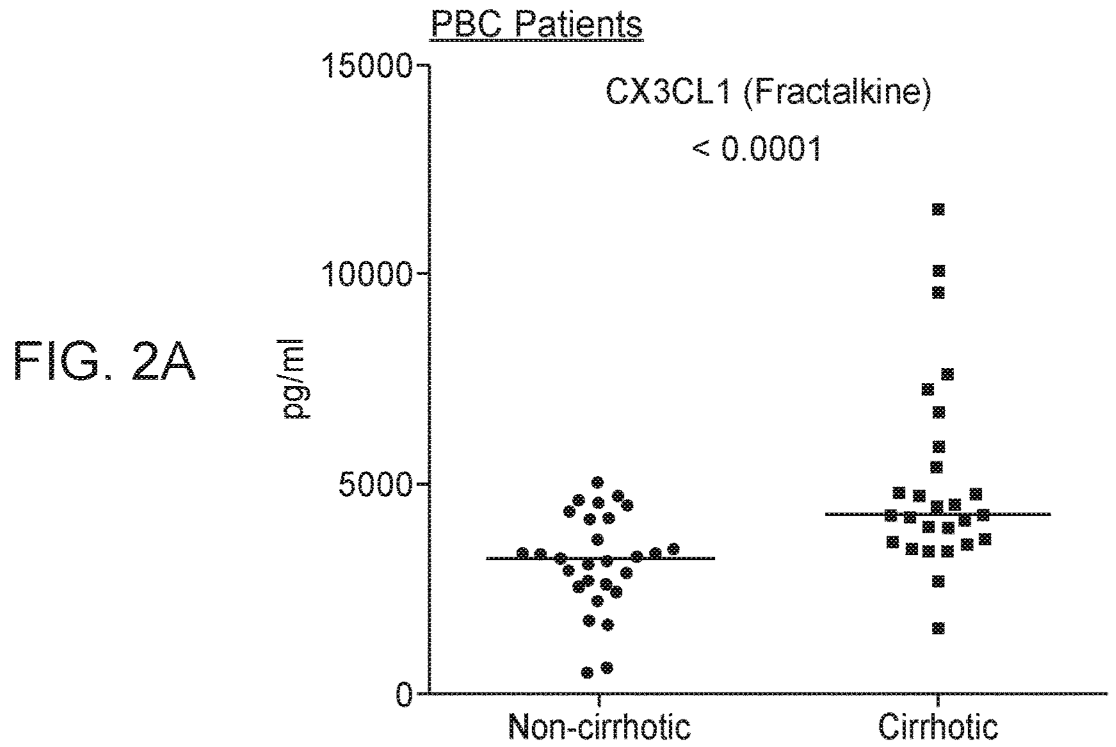
FIG. 2A. CX3CL1 (fractalkine) levels are significantly higher in PBC patients with cirrhosis compared to non-cirrhotic patients.
Figure 3:
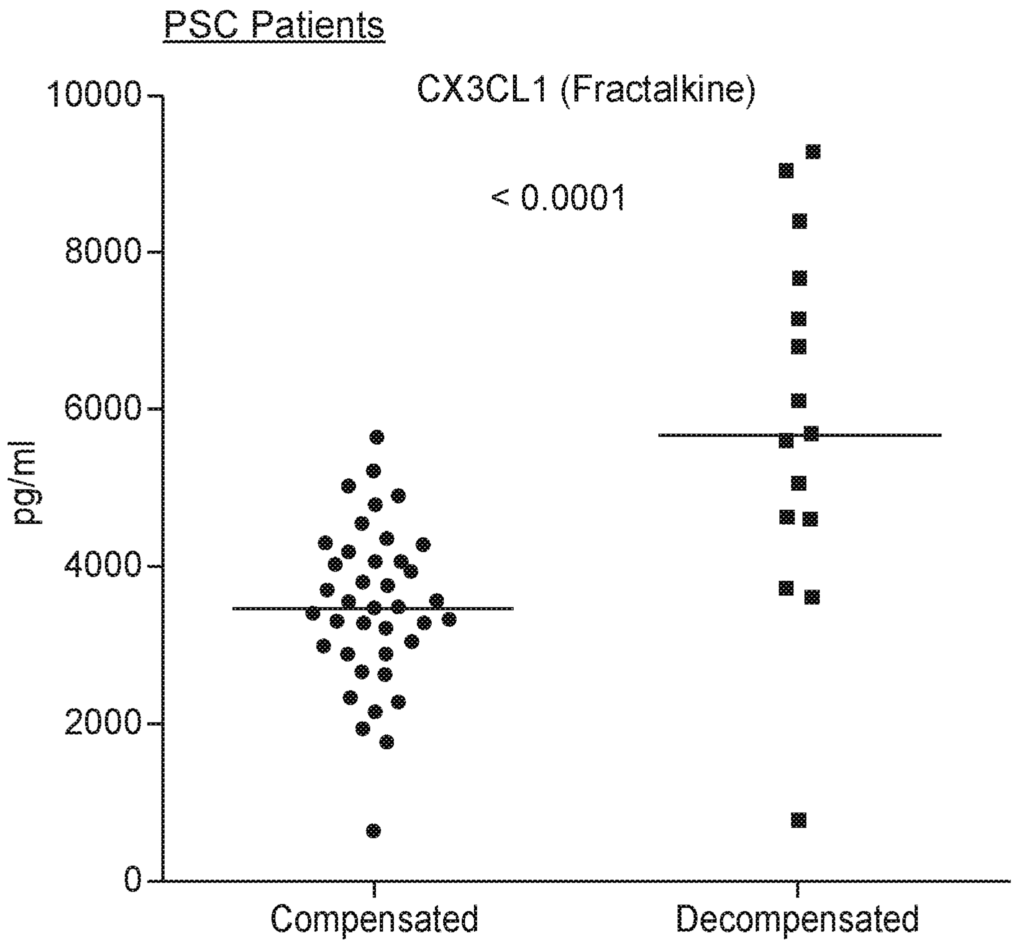
FIG. 3. CX3CL1 (fractalkine) levels are significantly higher in PSC patients with decompensated cirrhosis compared to compensated patients.

FIG. 2A. CX3CL1 (fractalkine) levels are significantly higher in PBC patients with cirrhosis compared to non-cirrhotic patients.

Figure 2B:
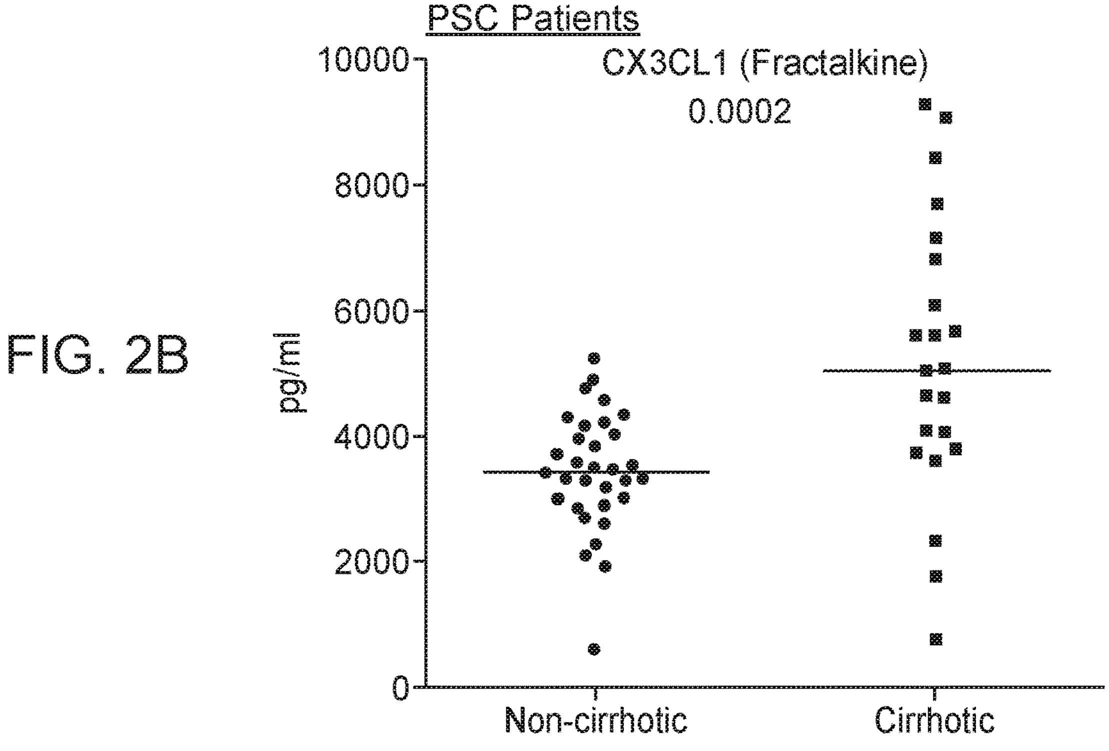
FIG. 2B. CX3CL1 (fractalkine) levels are significantly higher in PSC patients with cirrhosis compared to non-cirrhotic patients.

FIG. 2B. CX3CL1 (fractalkine) levels are significantly higher in PSC patients with cirrhosis compared to non-cirrhotic patients.

FIG. 3. CX3CL1 (fractalkine) levels are significantly higher in PSC patients with decompensated cirrhosis compared to compensated patients.

Example 2: Markers for Disease Remission or Response to Treatment in PBC and AIH Immunosuppressive therapy includes predniso (lo) ne or budesonide in non-cirrhotic patients with or without azathioprine (Manns, M. P., et al., supra). Biochemical response (normalization of serum transaminases) can be achieved in about 80% of patients, but unfortunately inflammatory histological activity persists despite biochemical remission and hepatitis relapse after the withdrawal of immunosuppression is almost universal (van Gerven, N. M., et al., J Hepatol, 2013. 58(1): p. 141-7; Dhaliwal, H. K., et al., Am J Gastroenterol, 2015. 110(7): p. 993-9). Persistent histologic inflammatory activity in patients with biochemical response is associated with disease progression and reduced survival. Thus, there is an unmet need for non-invasive markers of inflammatory activity to distinguish patients who need a stronger immunosuppressive therapy and those whose remission correlates with complete therapy response.

Figure 4A:
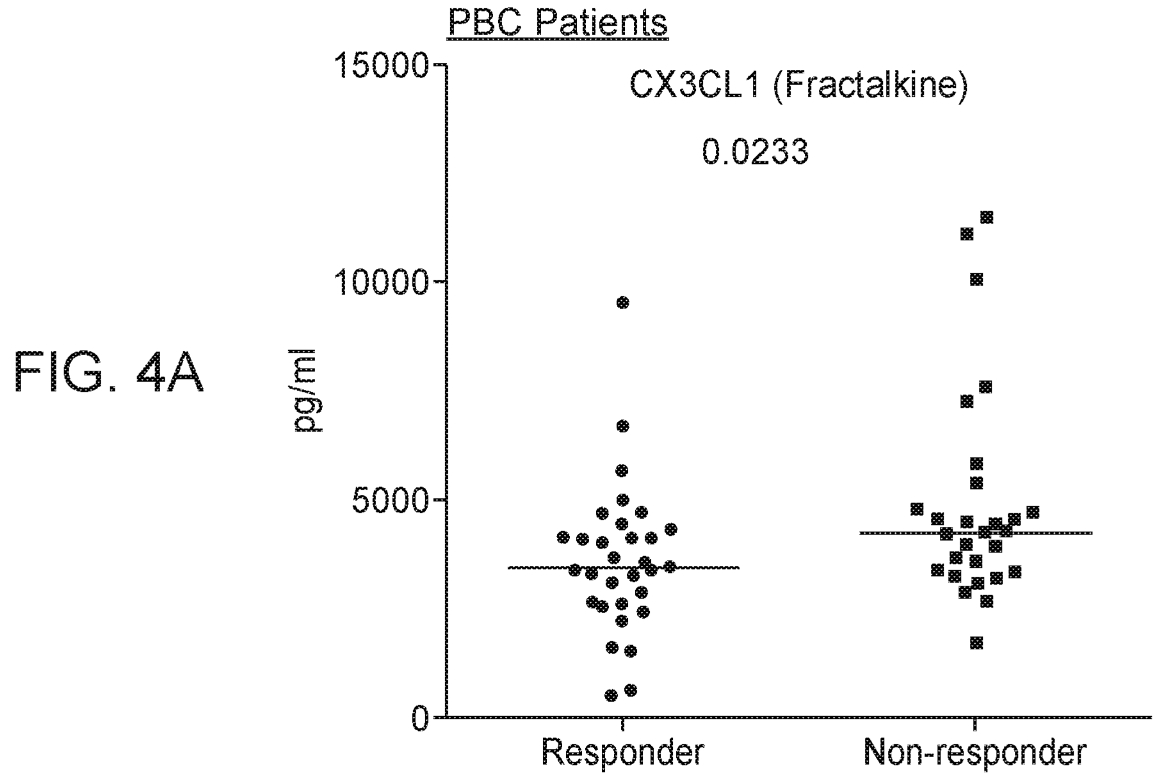
FIG. 4A. CX3CL1 (fractalkine) level is significantly higher in PBC patients that do not respond to treatment with ursodeoxycholic acid.
Figure 4B:
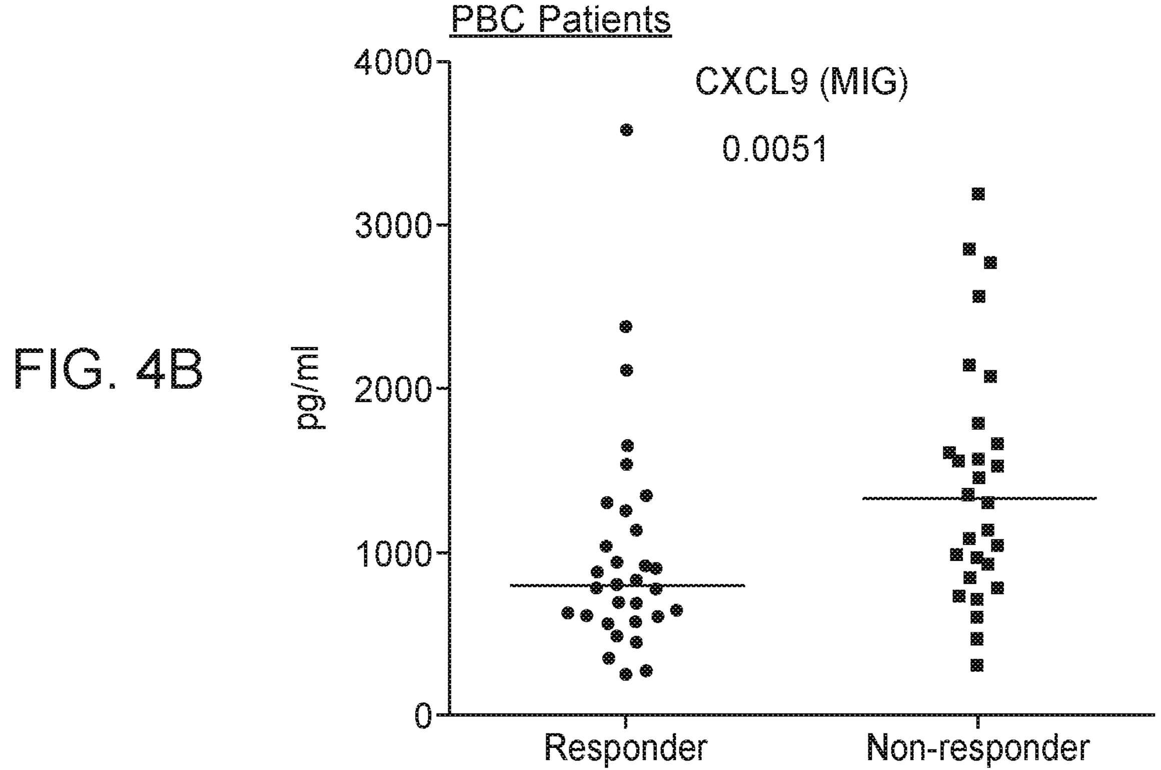
FIG. 4B. CXCL9 (MIG) level is significantly higher in PBC patients that do not respond to treatment with ursodeoxycholic acid.

Data provided in FIGS. 4A-4B shows that the levels of CX3CL1 and CXCL9 are significantly lower in PBC patients that responded to ursodeoxycholic acid treatment (FIGS. 4A and 4B). Response is described using pre-existing standard-of-care clinical and biochemical tests.

Figure 5A:
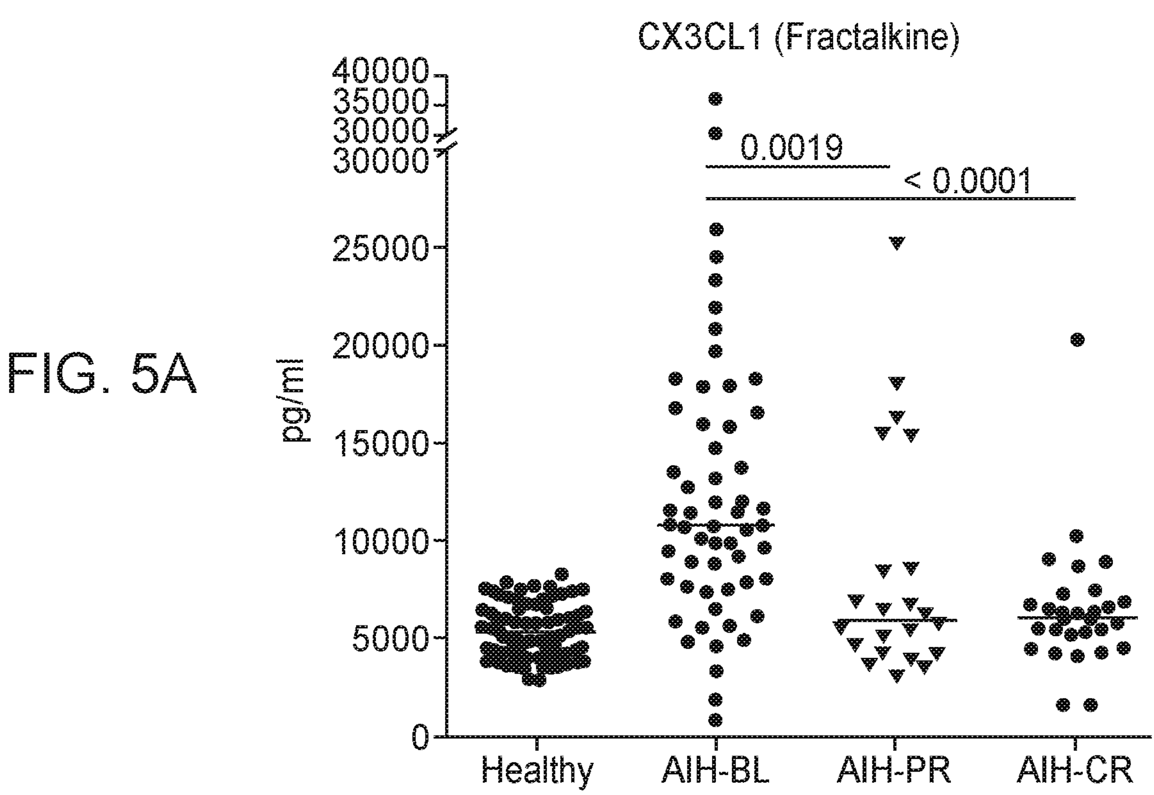
FIGS. 5A-5D. CX3CL1 (fractalkine) (FIG. 5A); CXCL9 (MIG) (FIG. 5B); CCL19 (MIP-3β) (FIG. 5C); and CCL26 (Eotaxin-3) (FIG. 5D) levels are significantly decreased in AIH patients in partial-remission (PR) or complete remission (CR) after treatment as compared to the baseline (BL) level before start of treatment.
Figure 5B:
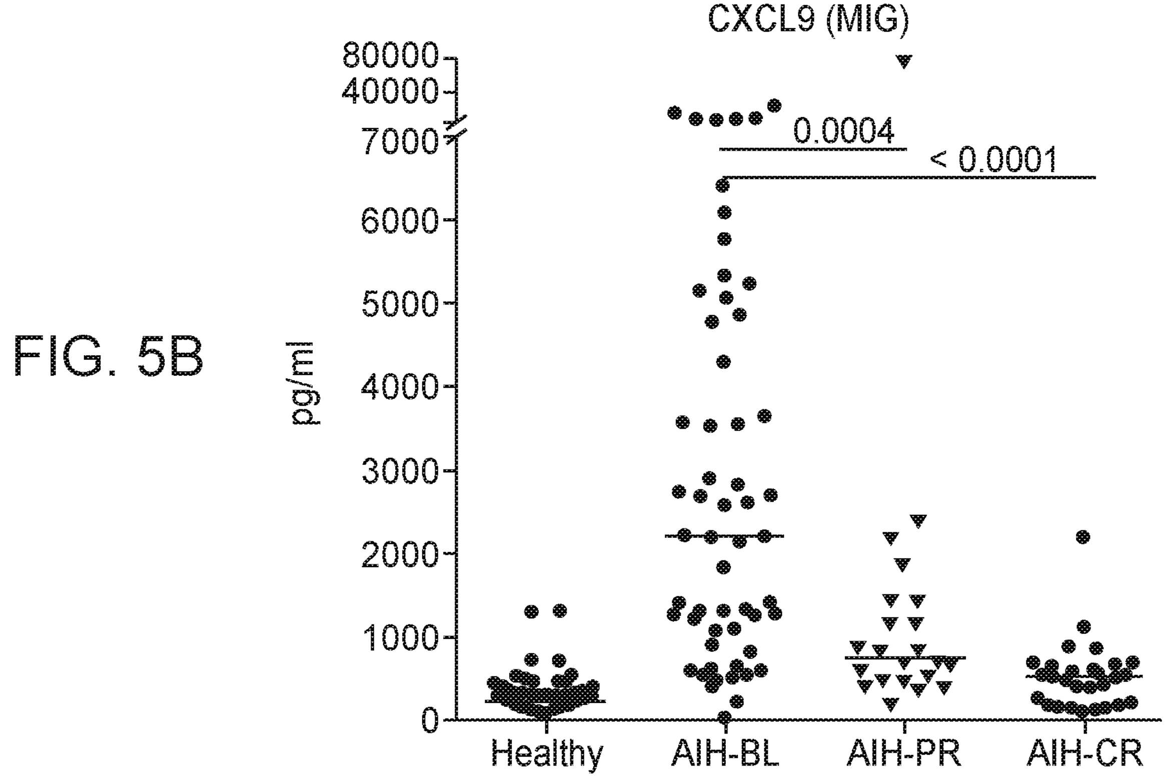
Figure 5C:
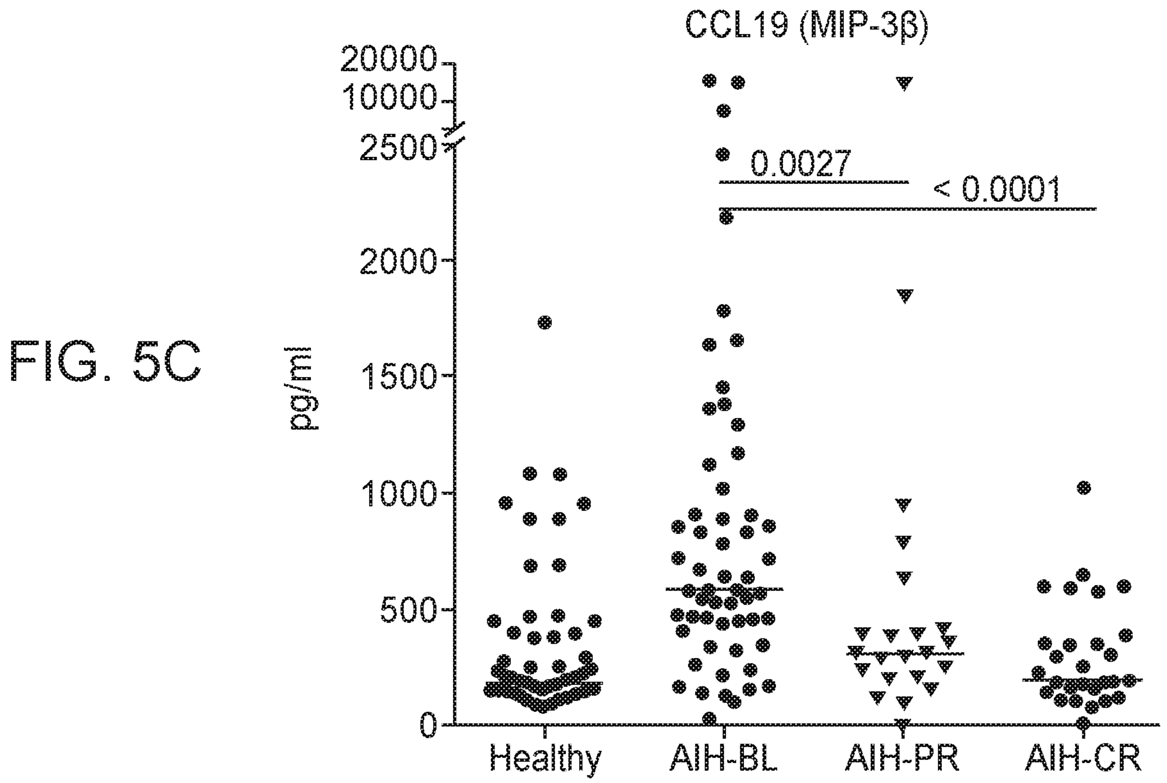
Figure 5D:
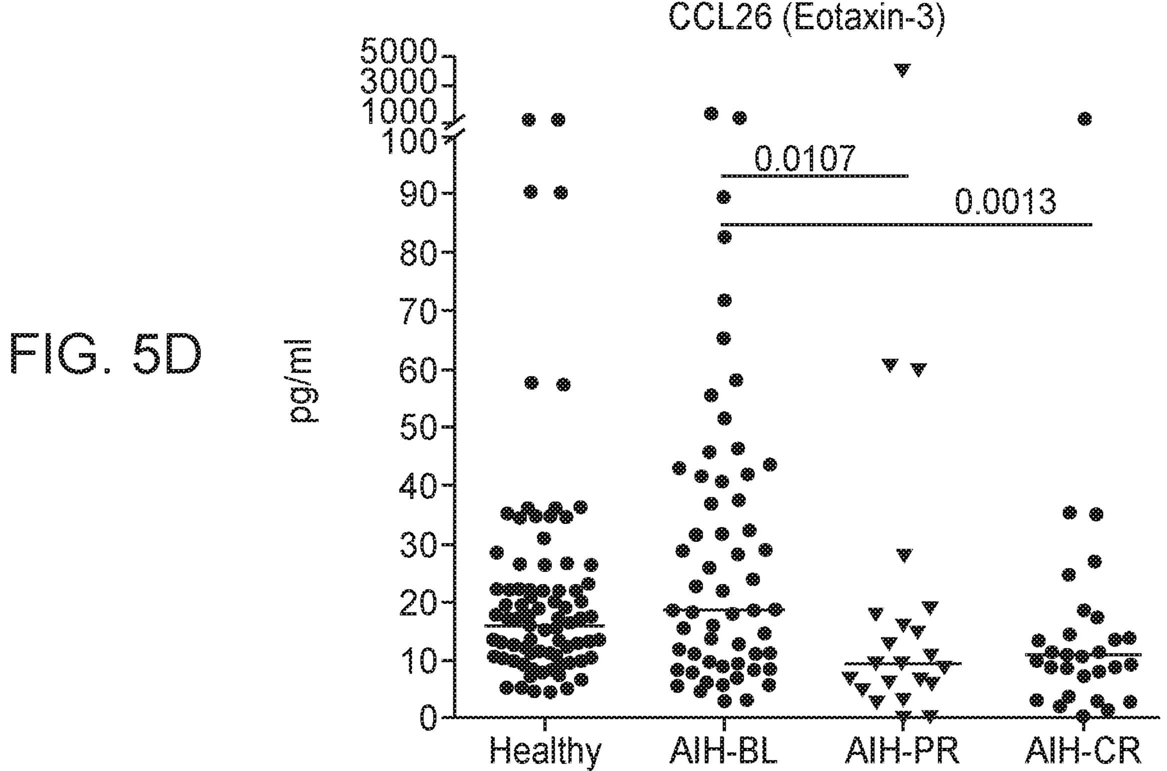

FIGS. 5A-5D. CX3CL1 (fractalkine) (FIG. 5A); CXCL9 (MIG) (FIG. 5B); CCL19 (MIP-3β) (FIG. 5C); and CCL26 (Eotaxin-3) (FIG. 5D) levels are significantly decreased in AIH patients in partial-remission (PR) or complete remission (CR) after treatment as compared to the baseline (BL) level before start of treatment.

Figure 6A:
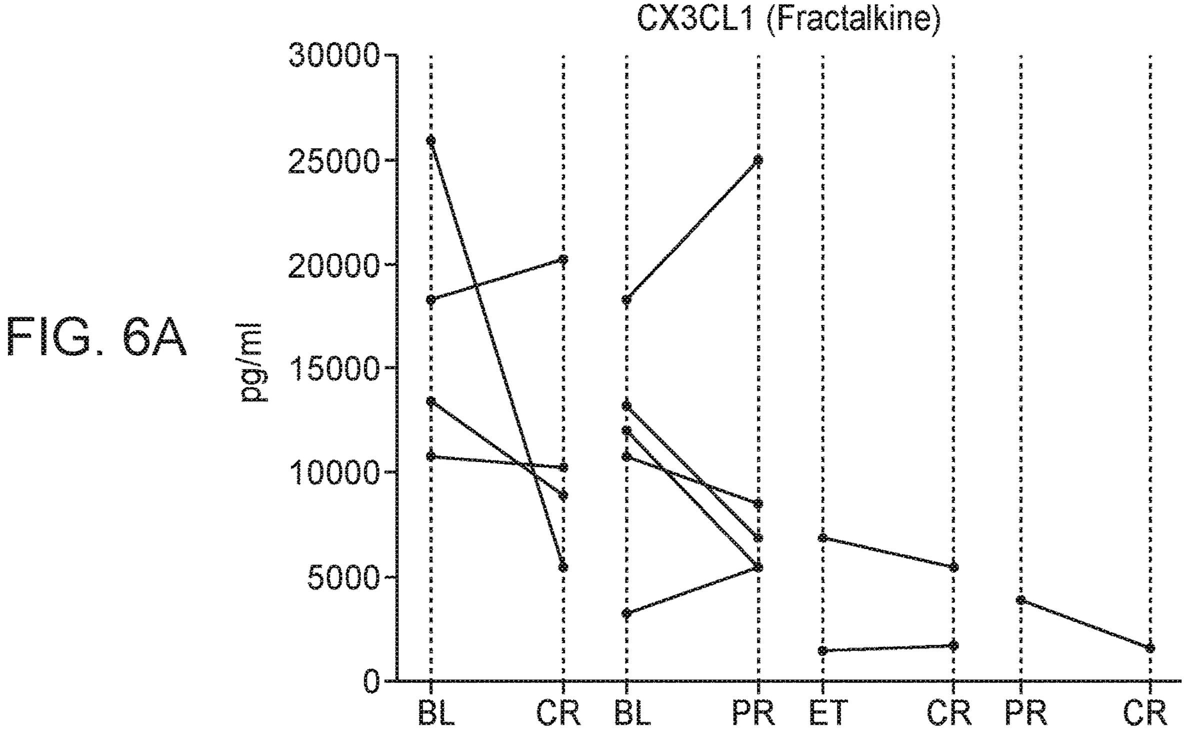
FIGS. 6A-6D. CX3CL1 (fractalkine) (FIG. 6A); CXCL9 (MIG) (FIG. 6B); CCL19 (MIP-3β) (FIG. 6C); and CCL26 (Eotaxin-3) (FIG. 6D) levels in individual AIH patients at diagnosis (baseline-BL), early treatment (ET), partial remission (PL) and complete remission (CR).
Figure 6B:
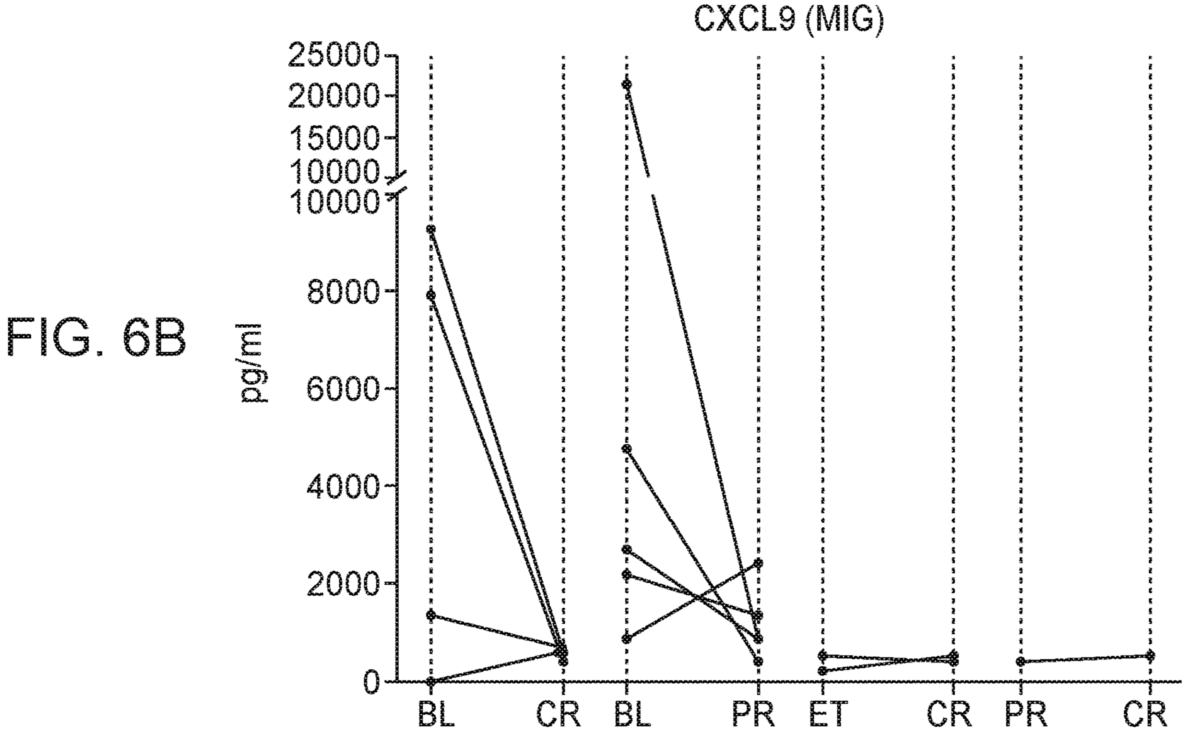
Figure 6C:
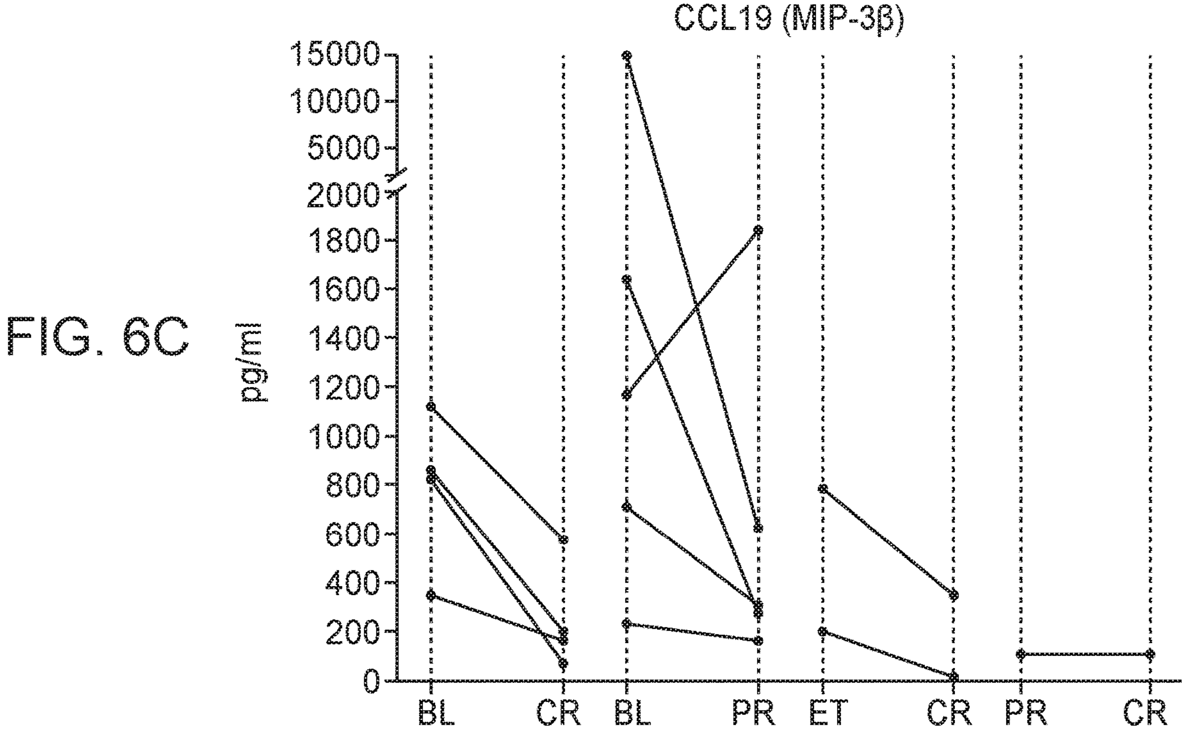
Figure 6D:
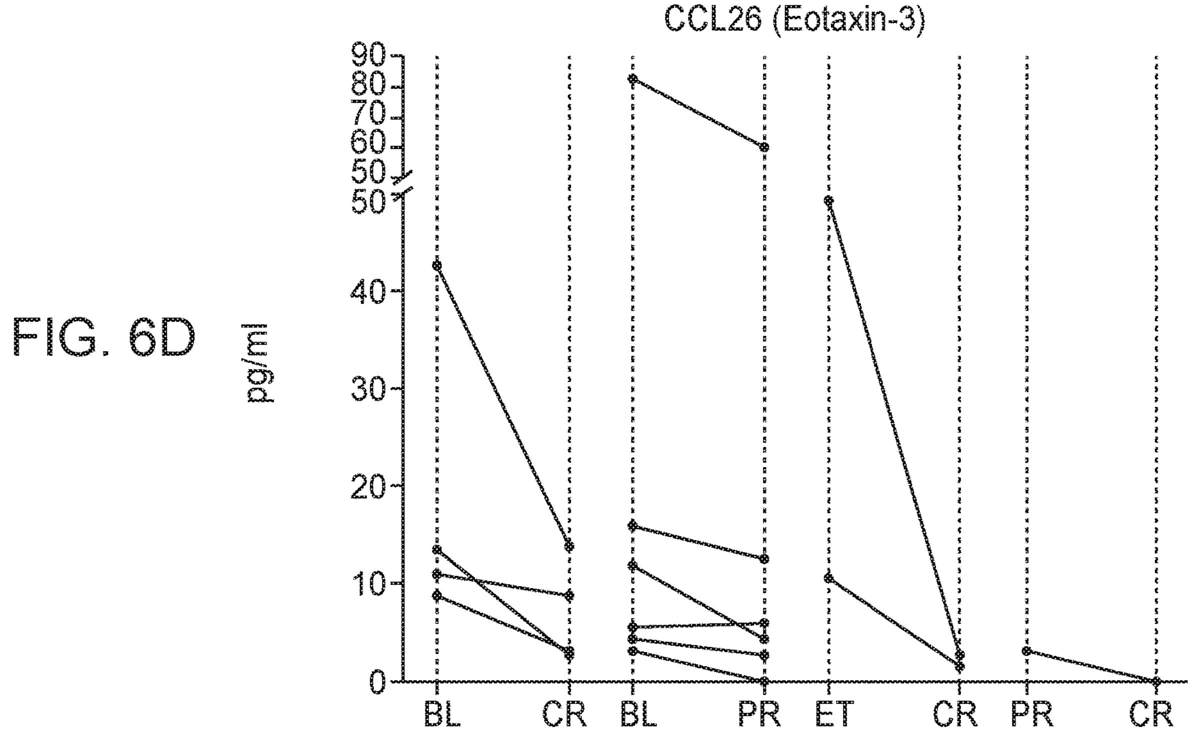

FIGS. 6A-6D. CX3CL1 (fractalkine) (FIG. 6A); CXCL9 (MIG) (FIG. 6B); CCL19 (MIP-3β) (FIG. 6C); and CCL26 (Eotaxin-3) (FIG. 6D) levels in individual AIH patients at diagnosis (baseline-BL), early treatment (ET), partial remission (PL) and complete remission (CR).

To evaluate disease remission and relapse, cut-offs were defined that can describe if the disease is in remission or relapse state.

PBC

To test if the level of CXCL9 can be used as an index to suggest if a patient has responded to a treatment or not, we set a cut-off at 700 pg/ml as the upper limit for normal range. Using this limit, 42% of responders (13 out of 31) displayed a level of CXCL9<700 pg/ml, while only 11% of non-responder (3 out of 28) had a level of CXCL9<700 pg/ml (42% sensitivity and 89% specificity). By adding CX3CL1 in this calculation, where the level of CXCL9 is <700 pg/ml or the level of CX3CL1 is <2500 pg/ml, the sensitivity for detection increased to 58% (18 out of 31), with a slight decrease in specificity (4 out of 28; 86% compared to 89%).

Thus, a cut-off 700 pg/ml plasma level for CXCL9 (and optionally a cut off of 2500 pg/ml CX3CL1) can be used to differentiate responders (who will have CXCL9 and if measured, CX3CL1, lower than the cut off) from non-responders (who will have CXCL9 plasma level and if measured, CX3CL1 plasma level, at or higher than the cut off). Reciprocally, for a patient who has been treated, a relapse is indicated when CXCL9 plasma level is equal to or higher than 700 pg/ml or when CXCL9 plasma level is equal to or higher than 700 pg/ml and CX3CL1 plasma level is equal to or higher than 2500 pg/ml.

AIH

In case of AIH, we first defined a normal range from CX3CL1, CXCL9, and CCL19 based on their mean value in healthy control group+/−3 standard deviation (SD). The upper limits of normal range for CX3CL1, CXCL9, or CCL19 were 9829 pg/ml, 506.1 pg/ml, or 1062.9 pg/ml, respectively. Using these cut-offs, if each of CX3CL1, CXCL9, or CCL19 is used alone, 50%, 57%, or 11% of the patients have responded to the treatment and are in remission state, respectively. If the reduction of either of one or two chemokines is used, the sensitivity will increase to 68%.

These results suggest that CX3CL1, CXCL9, and CCL19 are correlated with response to treatment and thus disease remission in patients with AIH.

Figure 8C:
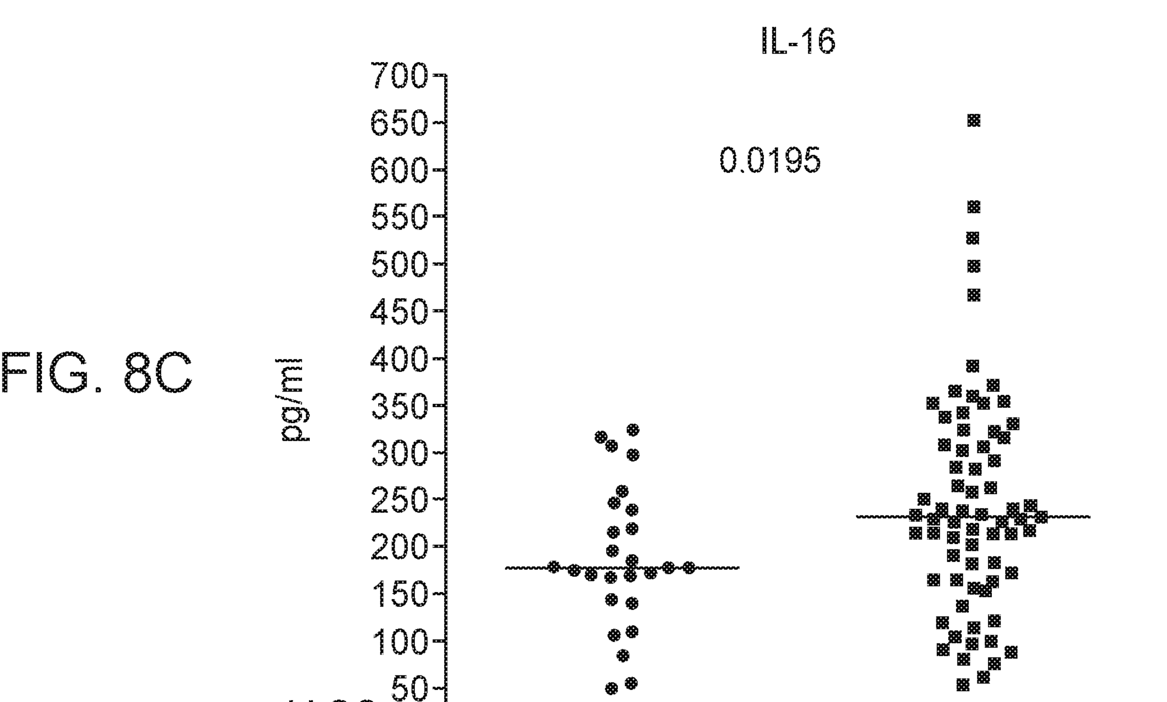
Figure 9A:
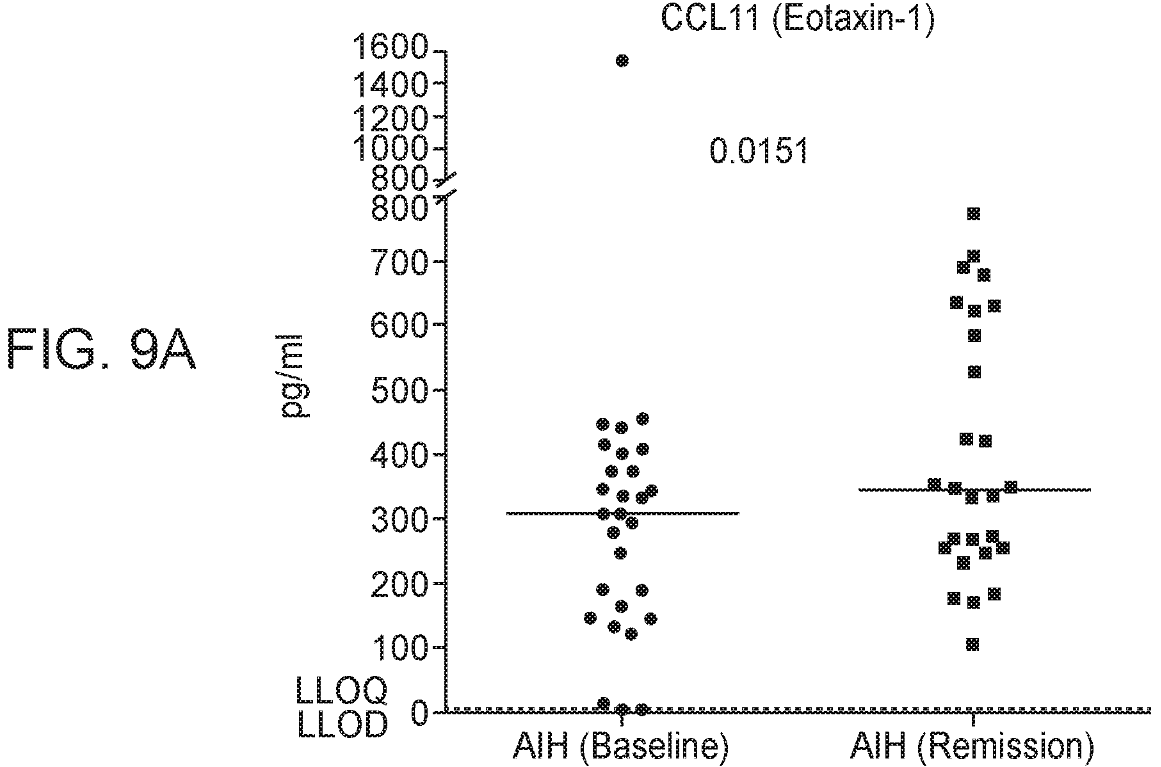
FIGS. 9A-9C. CCL11 (Eotaxin-1) (FIG. 9A), IL-15 (FIG. 9B), and IL-16 (FIG. 9C) plasma levels are not significantly decreased after treatment in AIH patients responsive (in remission) to treatment in comparison to their level at diagnosis (baseline).
Figure 9B:
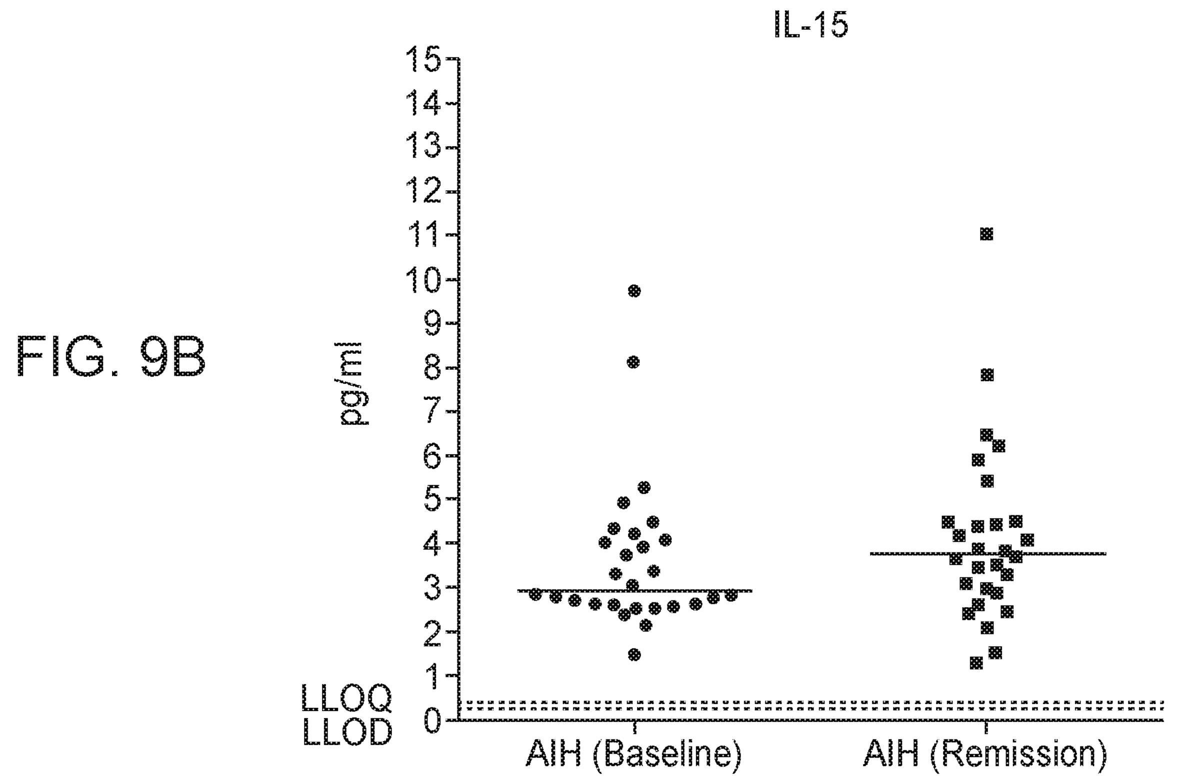
Figure 9C:
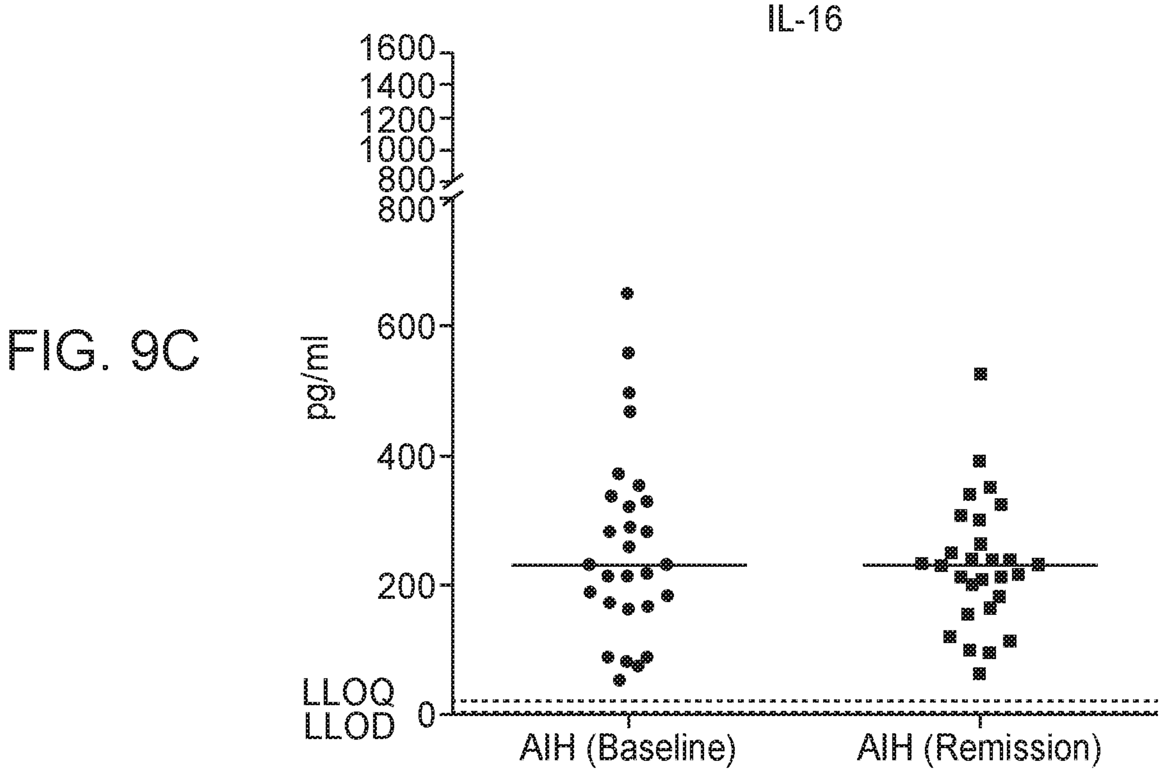
Figure 10A:
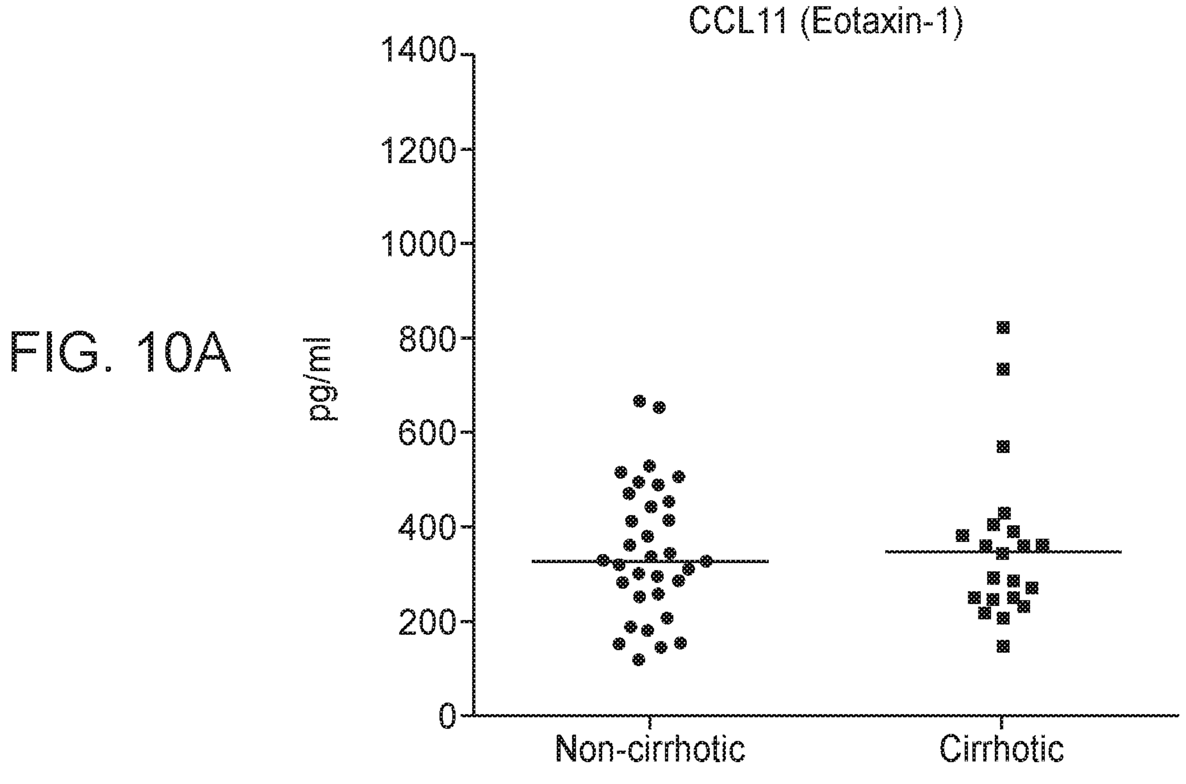
FIGS. 10A-10D. Levels of cytokines/chemokines CCL11 (Eotaxin-1) (FIG. 10A), IL-7 (FIG. 10B), CCL26 (FIG. 10C), and VEGF-A (FIG. 10D) that are not different in PSC patients with cirrhosis versus non-cirrhotic PSC patients.
Figure 10B:
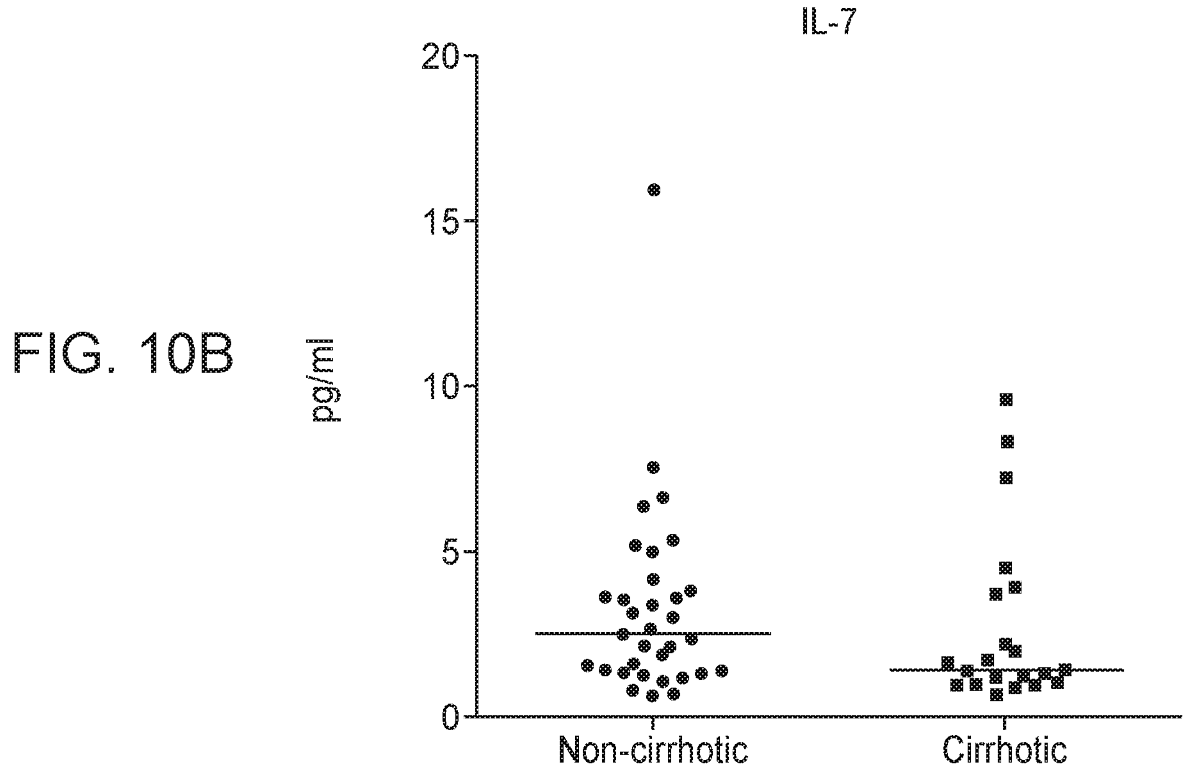
Figure 10C:
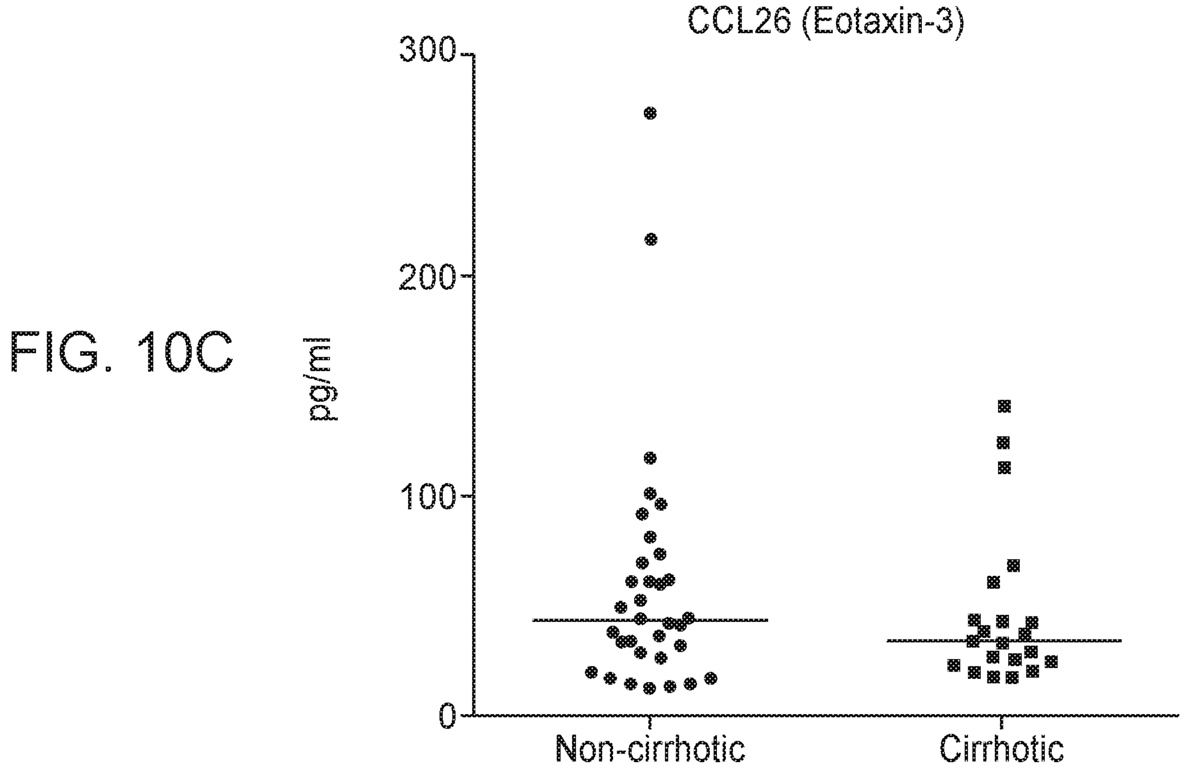
Figure 10D:
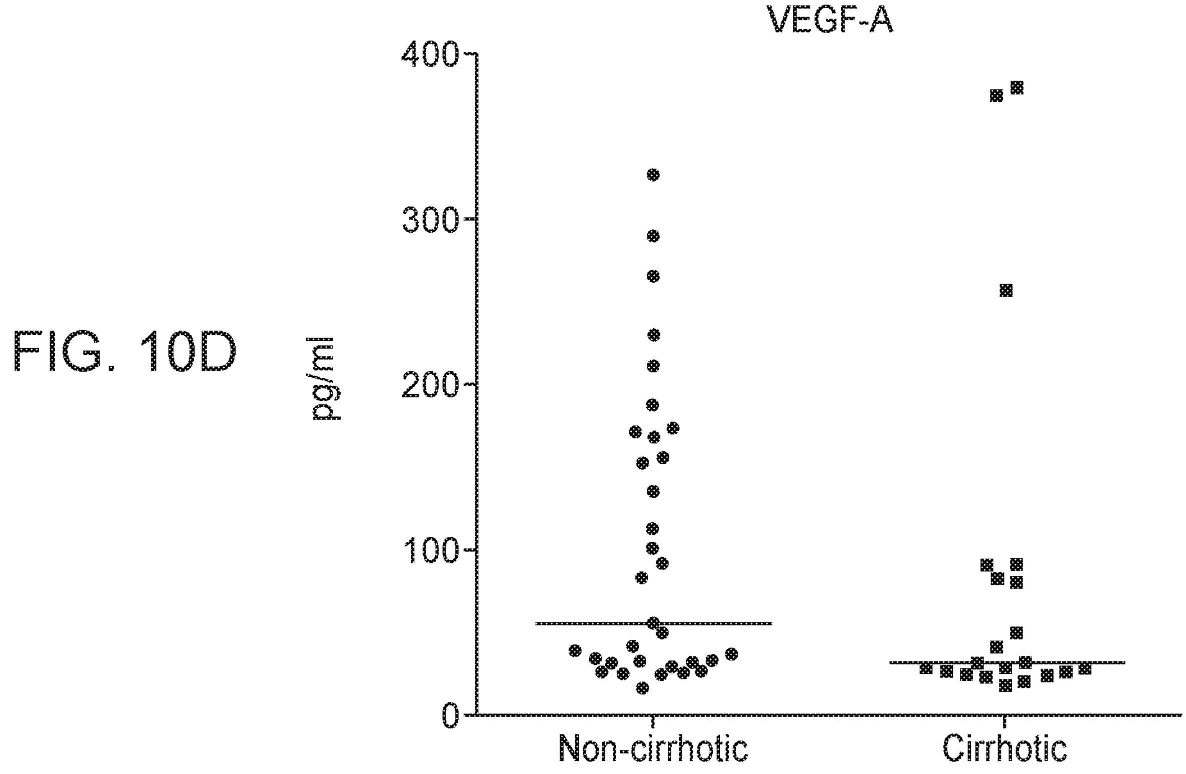
Figure 11A:
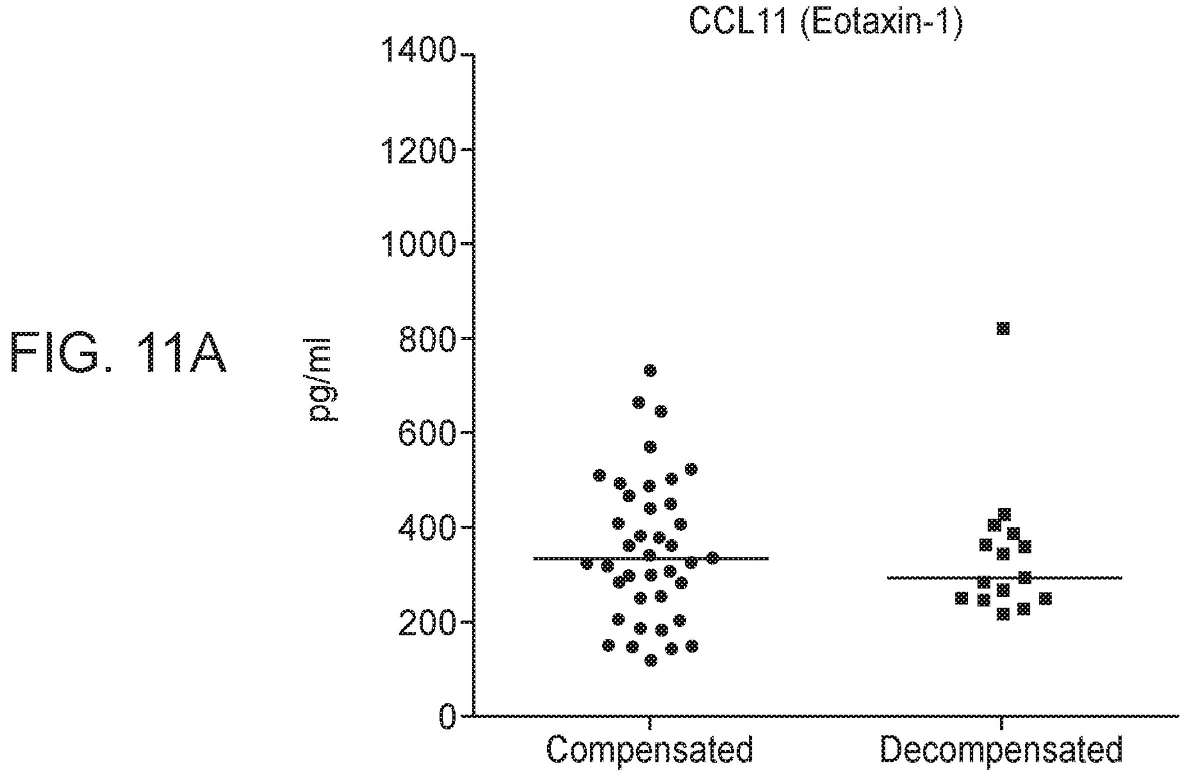
FIGS. 11A-11D. Levels of cytokines/chemokines CCL11 (Eotaxin-1) (FIG. 11A), IL-7 (FIG. 11B), CCL26 (FIG. 11C), and VEGF-A (FIG. 11D) that are not different in PSC patients with decompensated versus compensated cirrhosis.
Figure 11B:
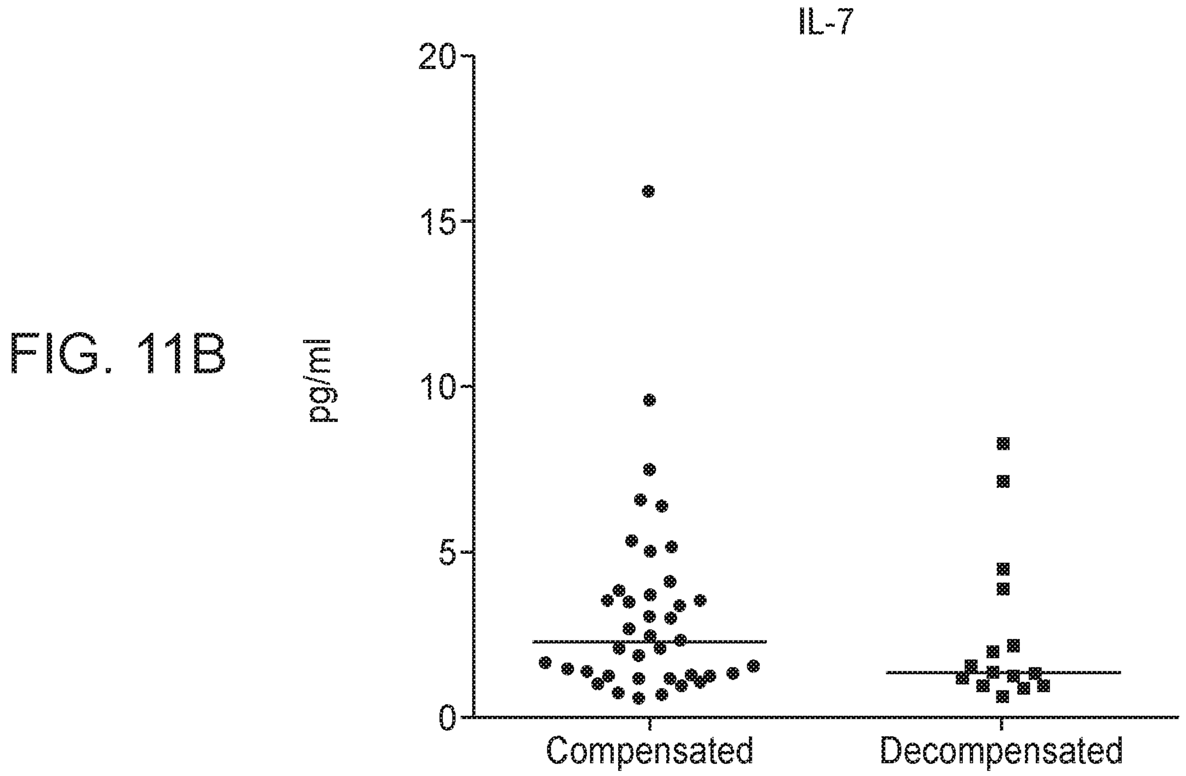
Figure 11C:
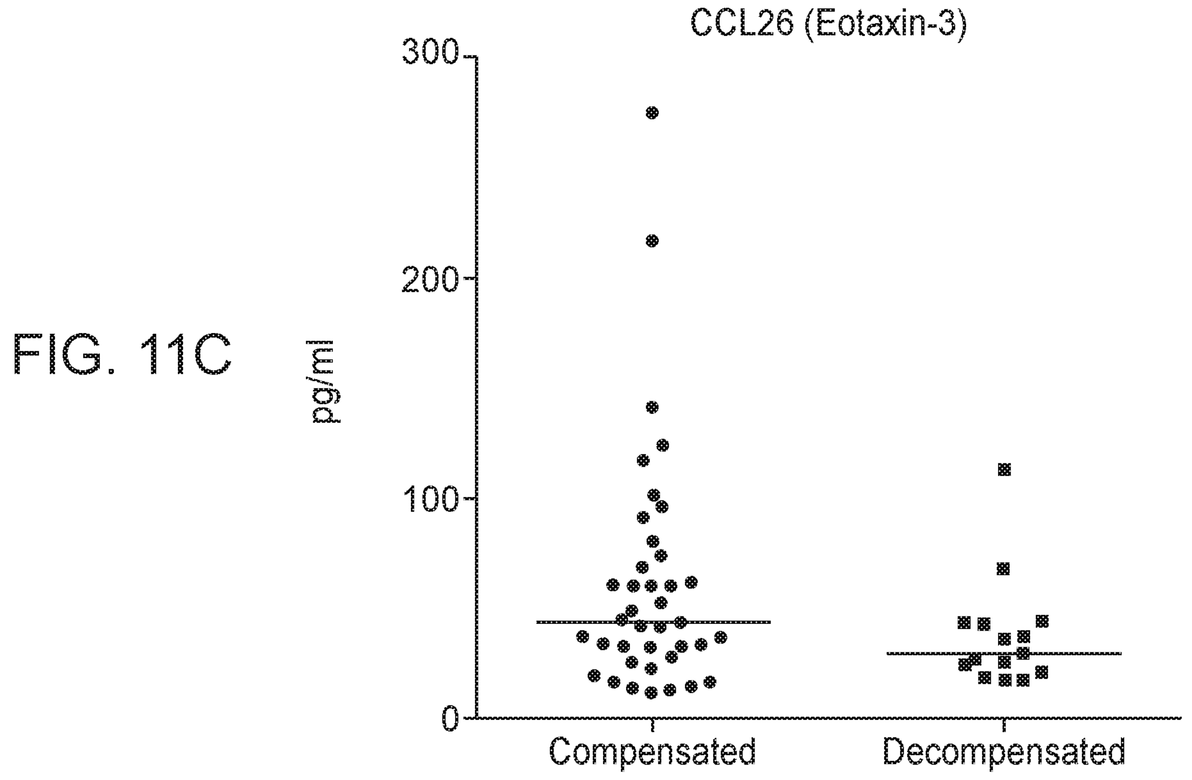
Figure 11D:
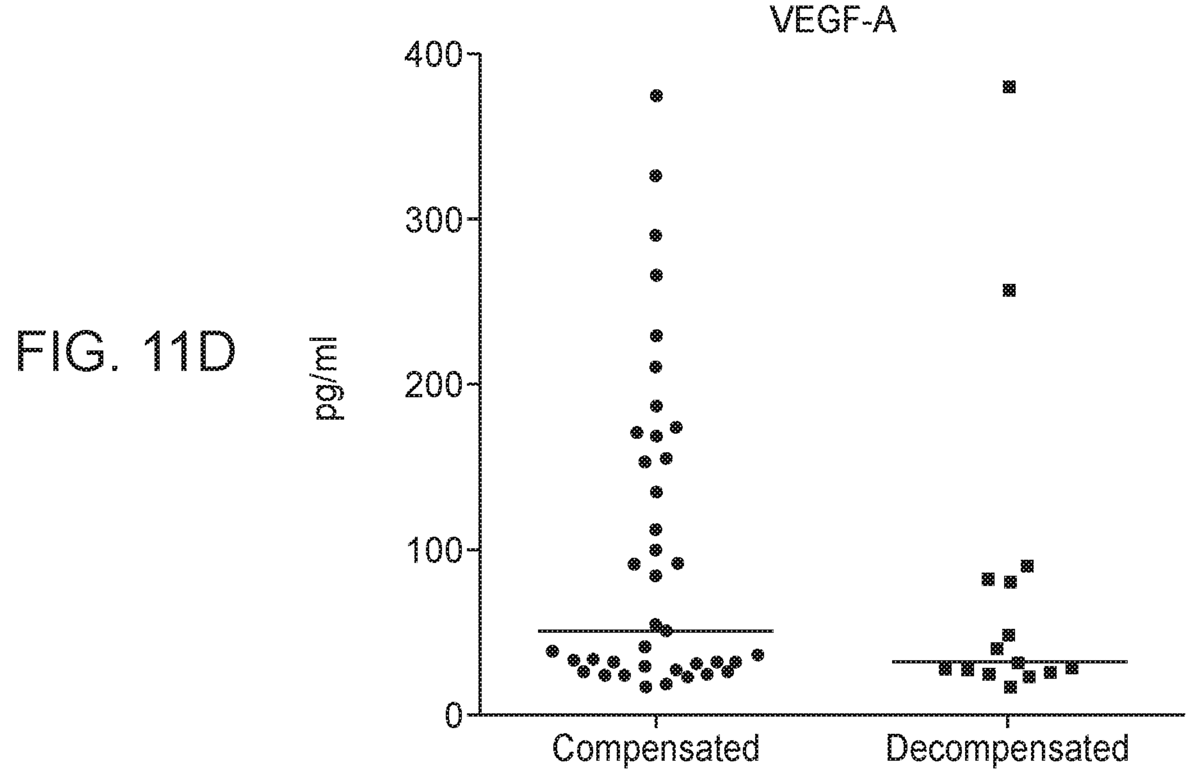
Figures 12A, 12B:
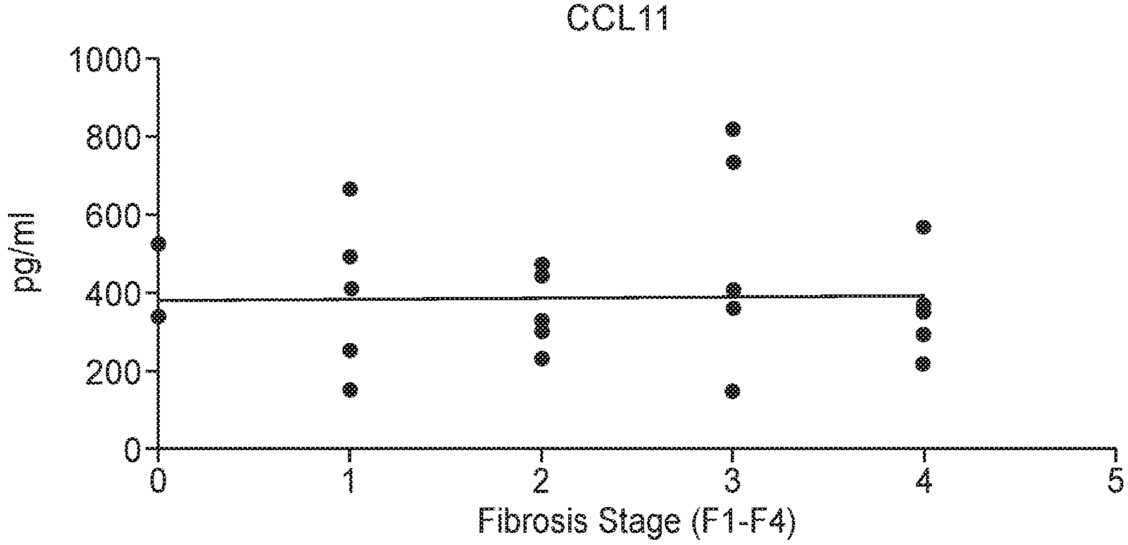
FIGS. 12A-12D. Levels of cytokines/chemokines CCL11 (Eotaxin-1) (FIG. 12A), IL-7 (FIG. 12B), CCL26 (FIG. 12C), and VEGF-A (FIG. 12D) that are not correlated with fibrosis stages in PSC patients.
Figure 12C:
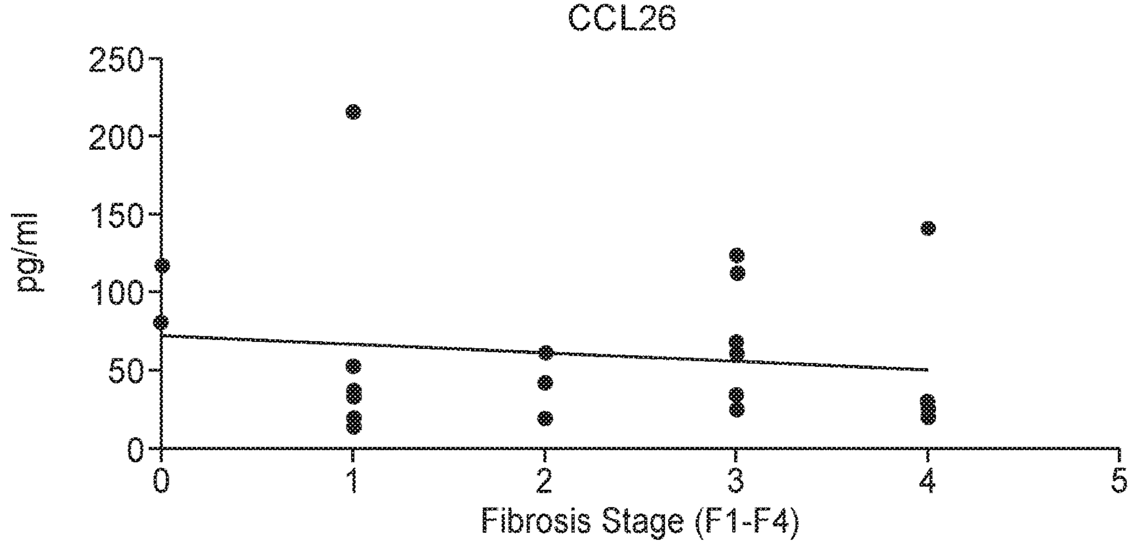
Figure 12D:
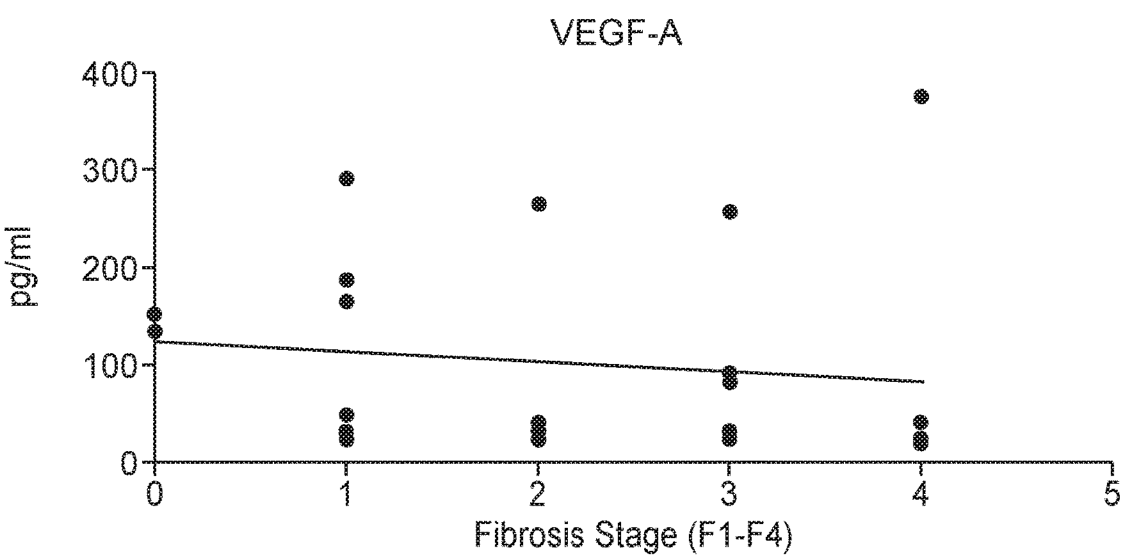
Figure 13A:
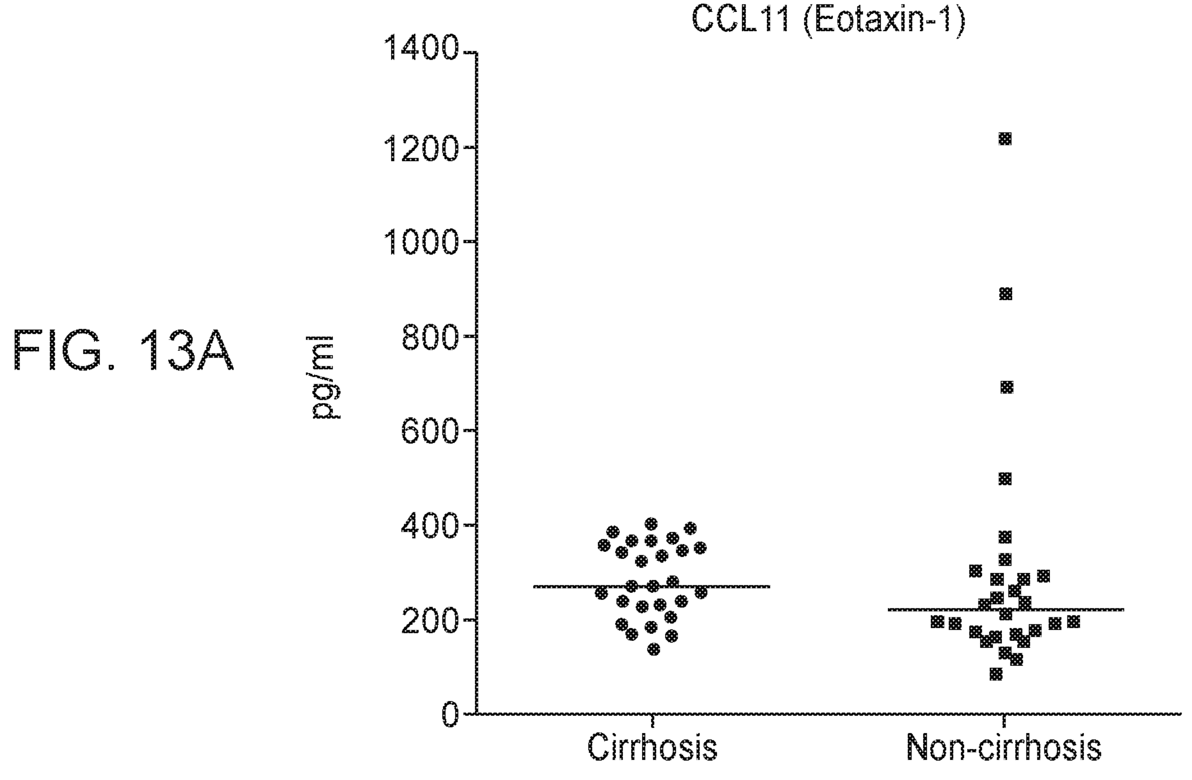
FIGS. 13A-13D. Levels of cytokines/chemokines CCL11 (Eotaxin-1) (FIG. 13A), IL-7 (FIG. 13B), CCL26 (FIG. 13C), and VEGF-A (FIG. 13D) that are not different in PBC patients with cirrhosis versus non-cirrhotic patients.
Figure 13B:
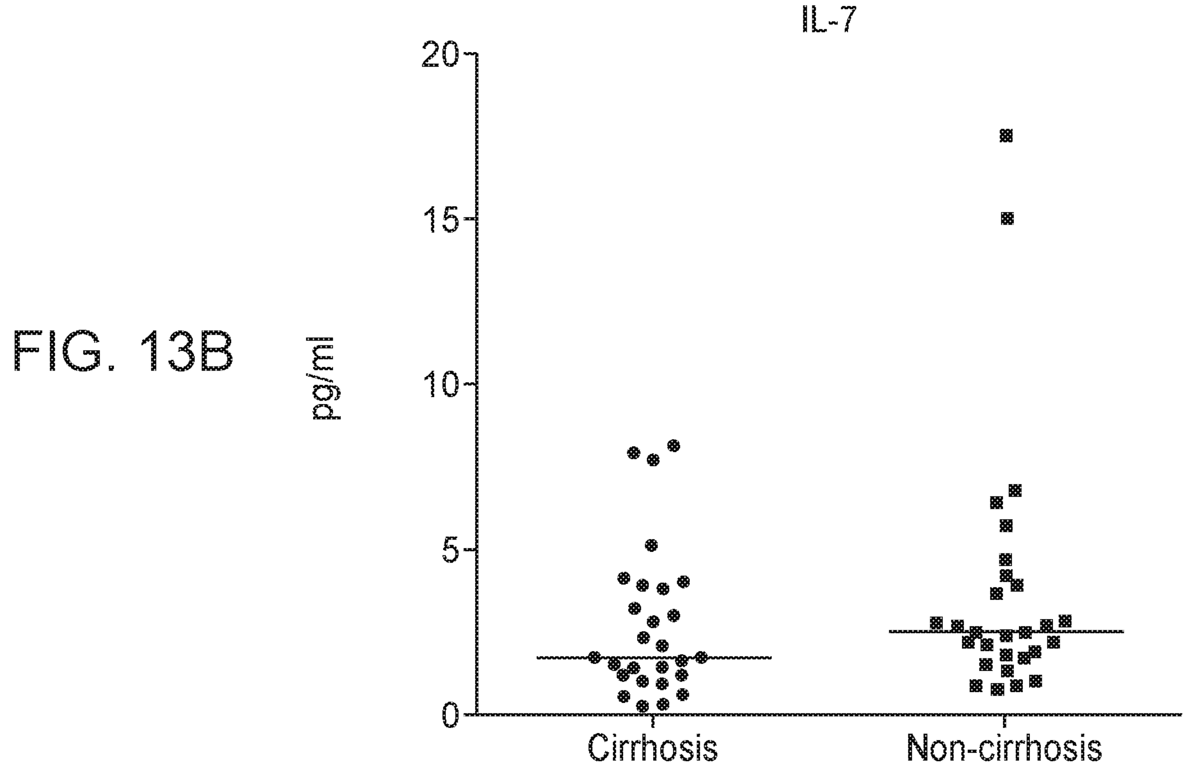
Figure 13C:
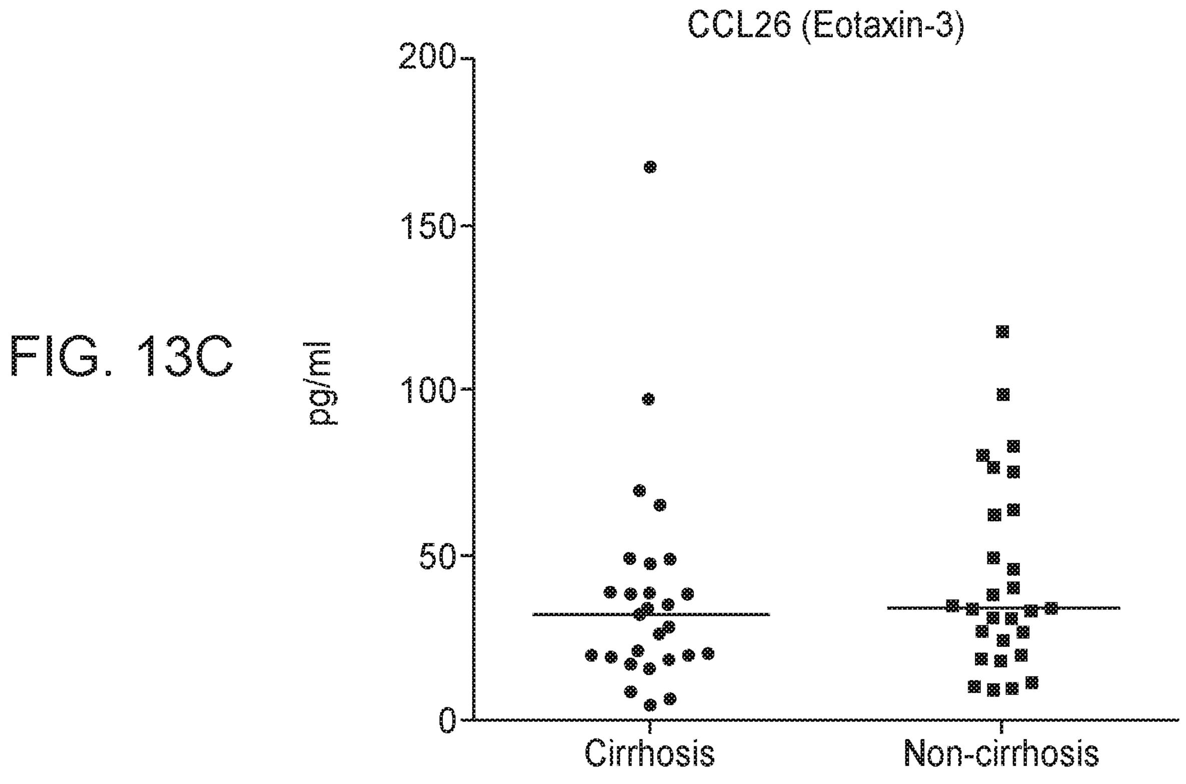
Figure 13D:
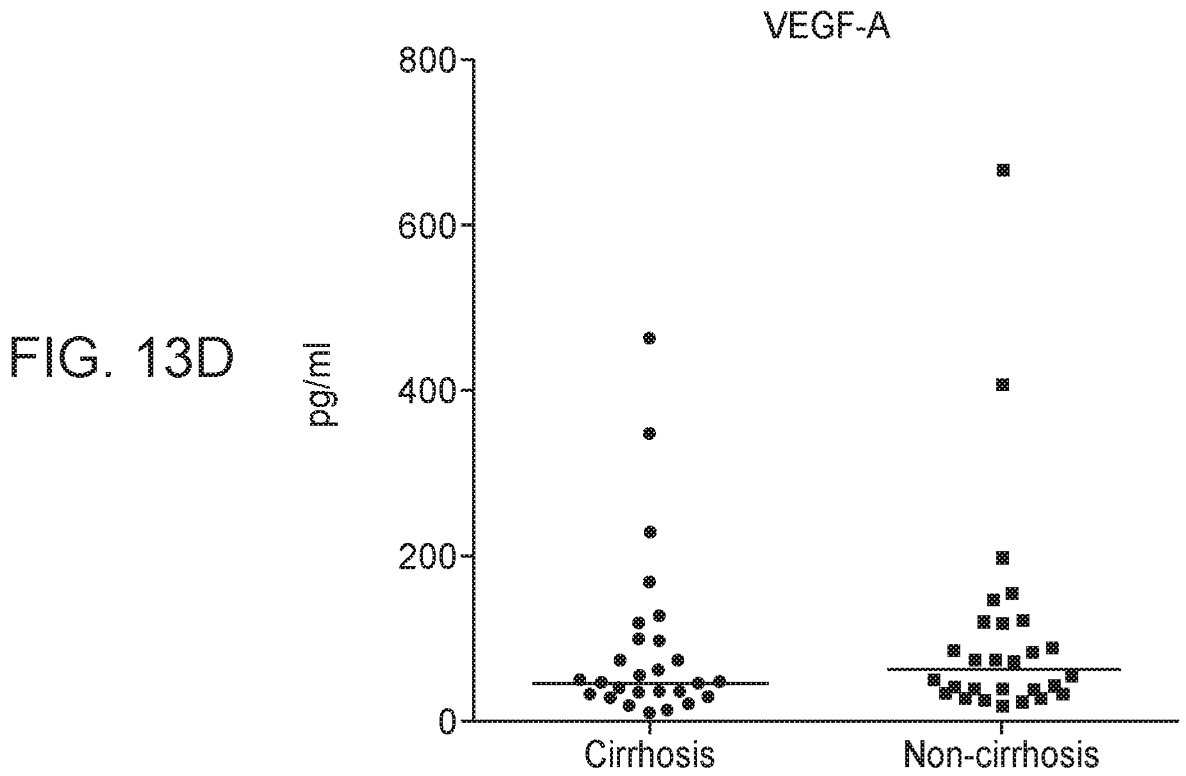
Figure 14A:
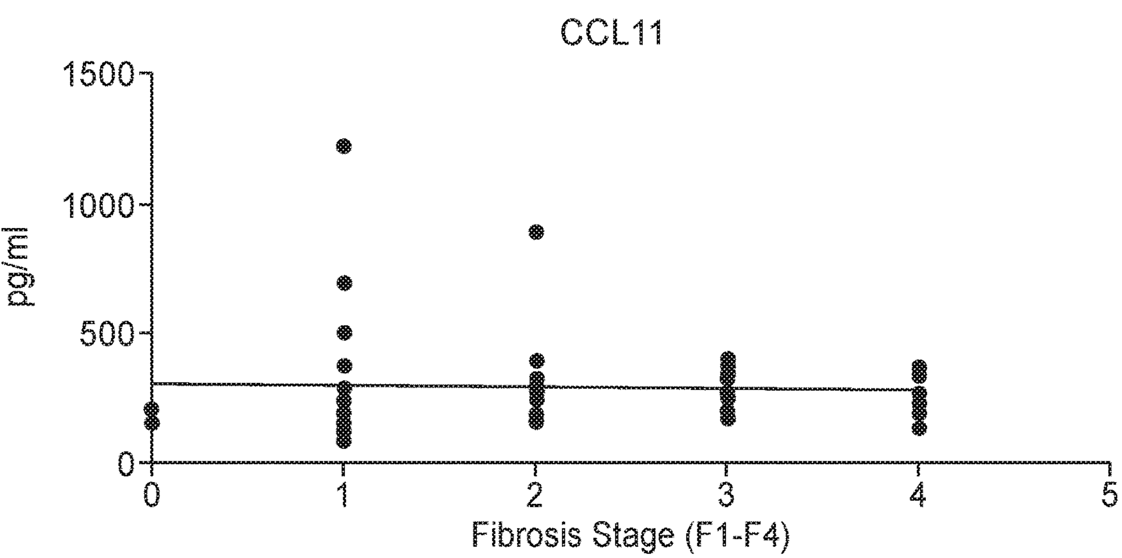
FIGS. 14A-14D. Levels of cytokines/chemokines CCL11 (Eotaxin-1) (FIG. 14A), IL-7 (FIG. 14B), CCL26 (FIG. 14C), and VEGF-A (FIG. 14D) that are not correlated with fibrosis stages in PBC patients.
Figure 14B:
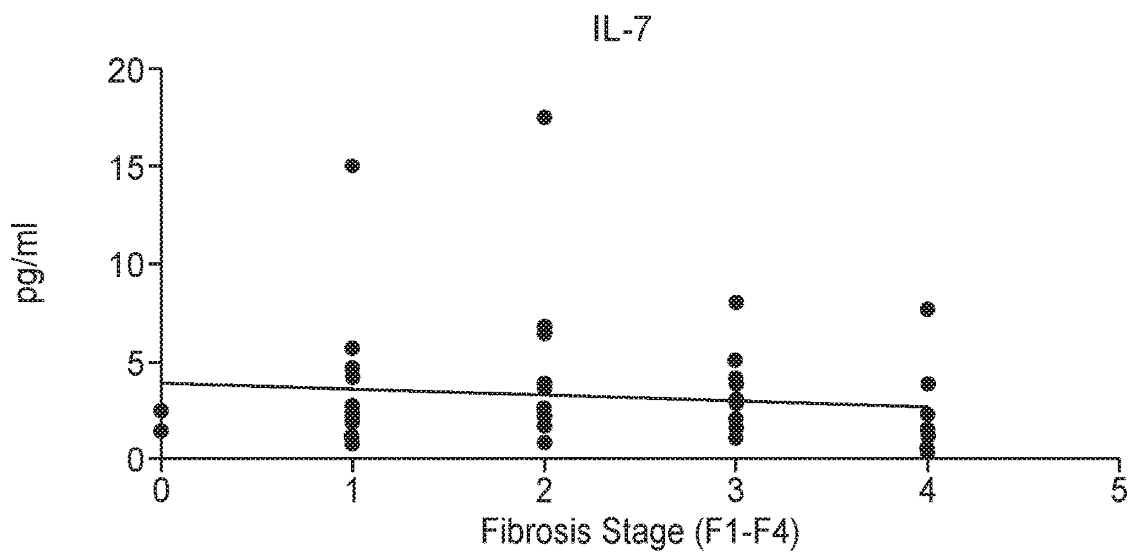
Figures 14C, 14D:
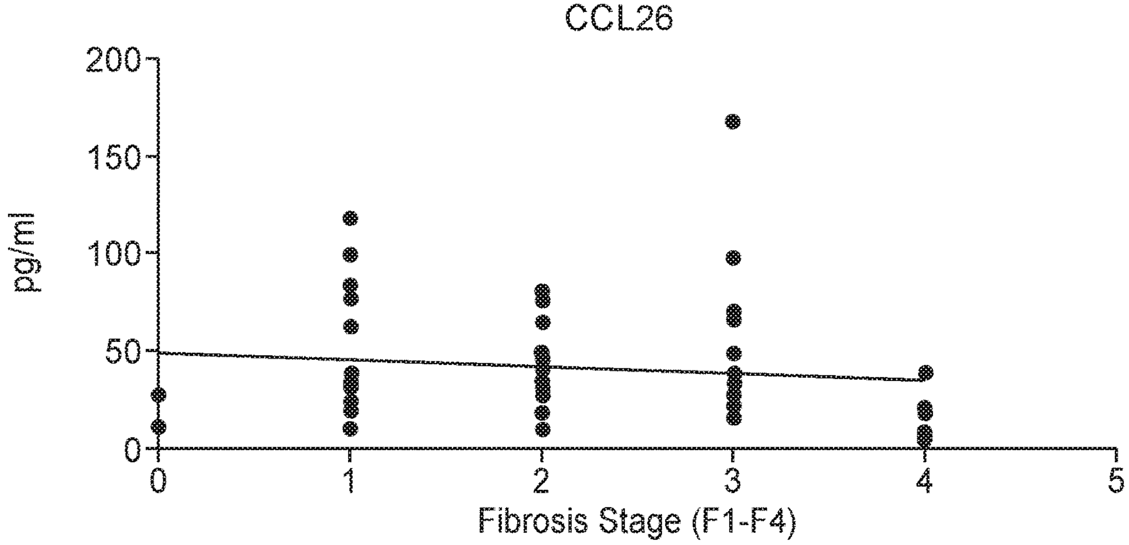

In contrast, other cytokines/chemokines such as CCL1, IL-5, IL-15, and IL-16, IL17A that are known to be increased in AIH patients did not decrease after treatment in the patients that responded to the treatment and thus were in remission. For example, see FIGS. 8A-8C, which shows that levels of CCL1 (Eotaxin-1), IL-15, and IL-16 are significantly higher in AIH patients as compared to their levels in healthy control group. FIGS. 9A-9C show that there is no significant difference in plasma levels of CCL (Eotaxin-1), IL-15, and IL-16 in AIH patients that responded to treatment versus non-responders. Thus, CCL (Eotaxin-1), IL-15, and IL-16 cannot be used to determine a remission status of a patient that has responded to AIH treatment.

Example 3: Examples of Upregulated Cytokines not Correlated to Disease Severity The following data illustrates that a number of cytokines that have increased serum/blood levels in patients having ALD (such as, PSC or PBC) do not have any correlation to disease severity.

FIGS. 10A-10D. Levels of cytokines/chemokines CCL11 (Eotaxin-1) (FIG. 10A), IL-7 (FIG. 10B), CCL26 (FIG. 10C), and VEGF-A (FIG. 10D) that are not different in PSC patients with cirrhosis versus non-cirrhotic PSC patients.

FIGS. 11A-11D. Levels of cytokines/chemokines CCL11 (Eotaxin-1) (FIG. 11A), IL-7 (FIG. 11B), CCL26 (FIG. 11C), and VEGF-A (FIG. 11D) that are not different in PSC patients with decompensated versus compensated cirrhosis.

FIGS. 12A-12D. Levels of cytokines/chemokines CCL11 (Eotaxin-1) (FIG. 12A), IL-7 (FIG. 12B), CCL26 (FIG. 12C), and VEGF-A (FIG. 12D) that are not correlated with fibrosis stages in PSC patients.

FIGS. 13A-13D. Levels of cytokines/chemokines CCL11 (Eotaxin-1) (FIG. 13A), IL-7 (FIG. 13B), CCL26 (FIG. 13C), and VEGF-A (FIG. 13D) that are not different in PBC patients with cirrhosis versus non-cirrhotic patients.

FIGS. 14A-14D. Levels of cytokines/chemokines CCL11 (Eotaxin-1) (FIG. 14A), IL-7 (FIG. 14B), CCL26 (FIG.

14C), and VEGF-A (FIG. 14D) that are not correlated with fibrosis stages in PBC patients.

Example 4: CX3CL1, CCL19, and CXCL9 Levels Correlate with Likelihood of AIH and with Severity of AIH Histopathologic grading according Ishak classification is the current gold standard for diagnosing AIH. Correlation between serum cytokines and histopathologic grading according Ishak classification in AIH patients was assessed. Inclusion criteria included—Patients with liver biopsy and defined histopathologic grading according Ishak classification and availability of serum sample prepared from blood at within ±90 days of the liver biopsy.

Results: 51 out of 70 patients underwent a liver biopsy; 37 samples were ±90 days away from the liver biopsy; 24 out of 37 samples refer to biopsies that have already a defined histopathologic grading according Ishak.

TABLE 2

Linear correlation between cytokines and grading score according Ishak classification:

| Cytokines | | Grading (Ishak) |
|---|---|---|
| E1 | ρ | 0.001 |
| | P | 0.997 |
| | n | 24 |
| E3 | ρ | 0.204 |
| | P | 0.338 |
| | n | 24 |
| IL-15 | ρ | 0.150 |
| | P | 0.484 |
| | n | 24 |
| Fractalkine | ρ | 0.517 |
| | P | 0.010 |
| | n | 24 |
| MIG | ρ | 0.626 |
| | P | 0.001 |
| | n | 24 |
| CCL19 | ρ | 0.604 |
| | P | 0.002 |
| | n | 24 |

Figure 15A:
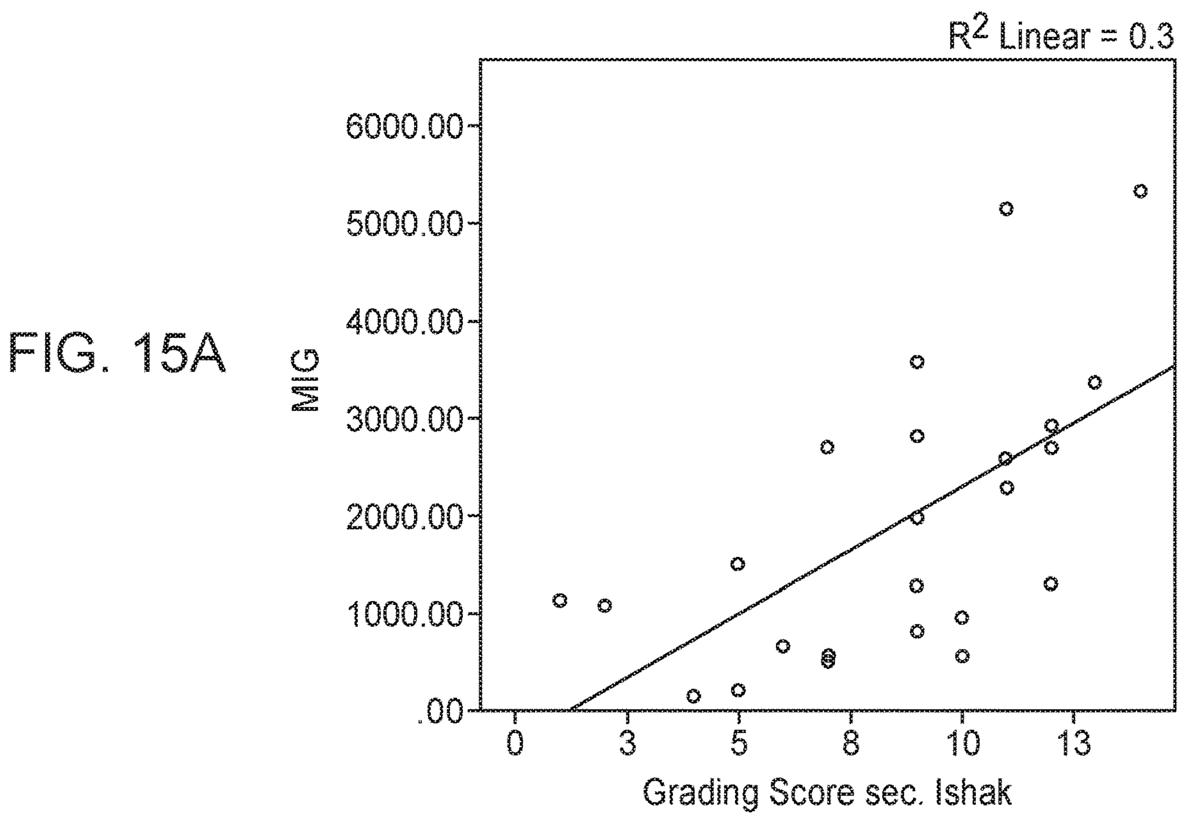
FIGS. 15A-15C. Higher serum level of MIG, CCL19, and Fractalkine correlate with higher Ishak grading score.
Figure 15B:
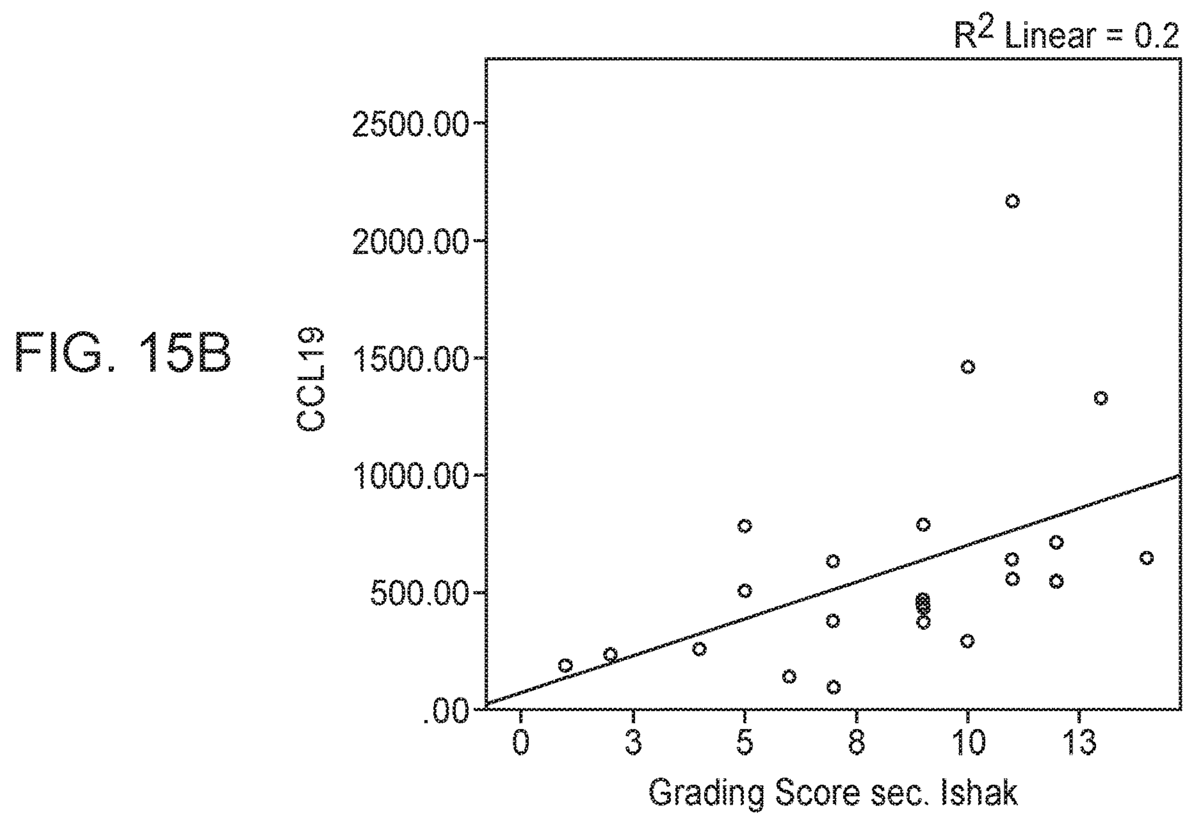
Figure 15C:
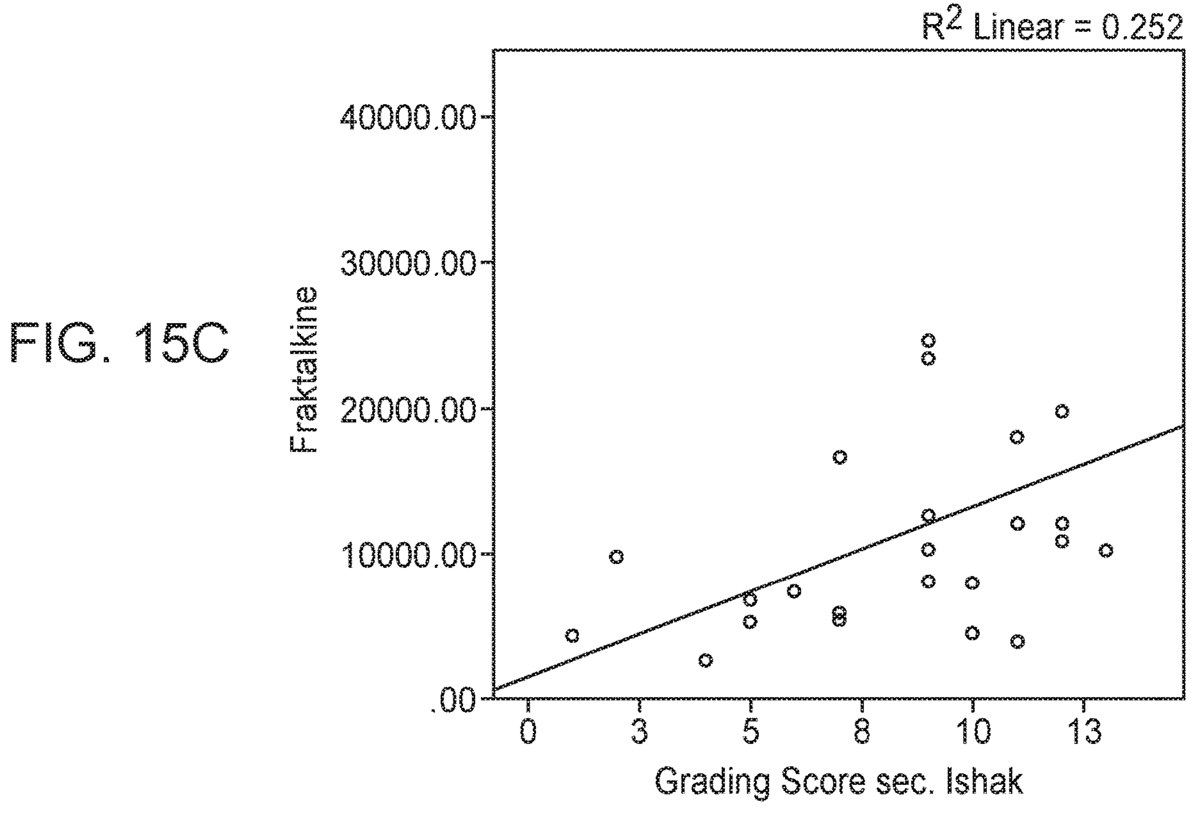

FIGS. 15A-15C demonstrate that serum levels of MIG (FIG. 15A), CCL19 (FIG. 15B), and Fractalkine (FIG. 15C) each correlate with Ishak grading score. The level of these cytokines increases in patients with higher Ishak grade.

TABLE 3 lists median and range of serum levels (in pg/ml) of listed cytokines in patients assigned either grade 0-9 or 10-18 based on Ishak classification:

| Cytokines | Grading (0-9) n = 14 | Grading (10-18) n = 10 | P |
|---|---|---|---|
| E1 | 384.30 (14-2637.10) | 373.35 (227.60-771.20) | 0.796 |
| E3 | 9.10 (3.50-49.10) | 12.15 (5.90-46.40) | 0.403 |
| IL-15 | 1.50 (0.60-4.10) | 1.35 (1.10-2.60) | 0.931 |
| Fractalkine | 7727.55 (2590.70-24490.80) | 11403.95 (3903.60-36028.20) | 0.341 |
| MIG | 1104.40 (150.70-3567.40) | 2636.25 (560.00-5322.90) | 0.042 |
| CCL19 | 406.75 (95.90-787.00) | 642.00 (289.50-2168.00) | 0.006 |

Figure 16A:
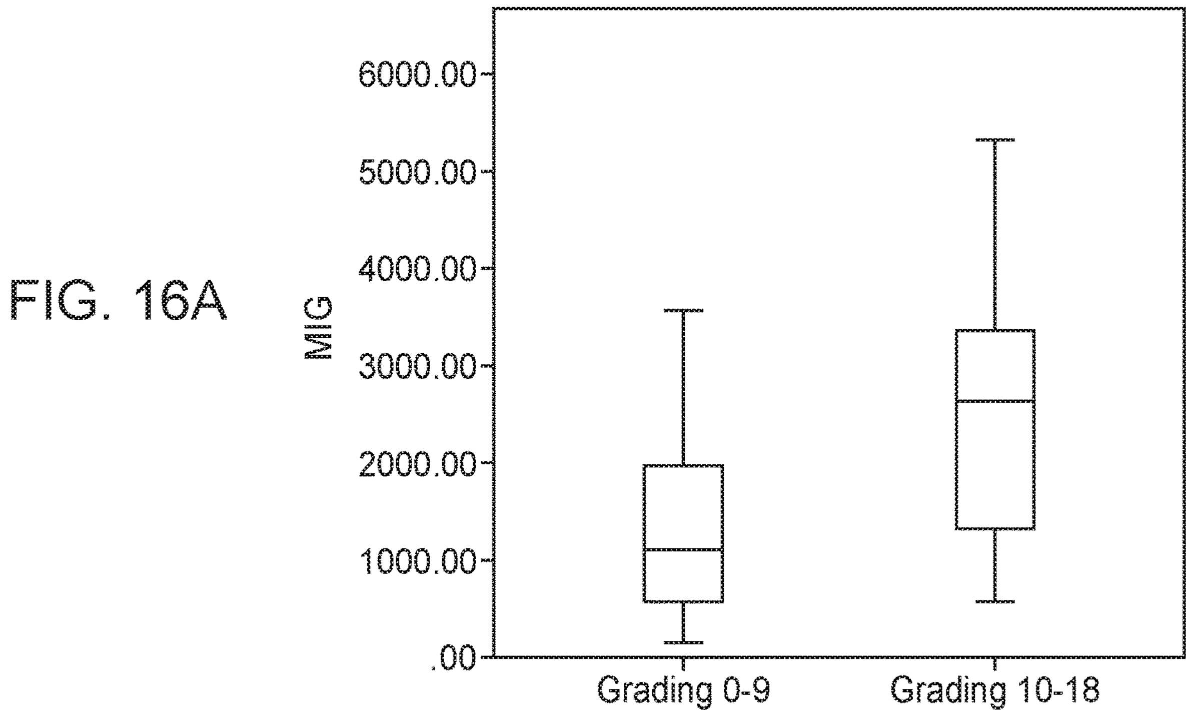
FIGS. 16A-16B. Serum level of MIG and CCL19 distinguish between Ishak grading 0-9 patients vs. Ishak grading 10-18 patients.
Figure 16B:
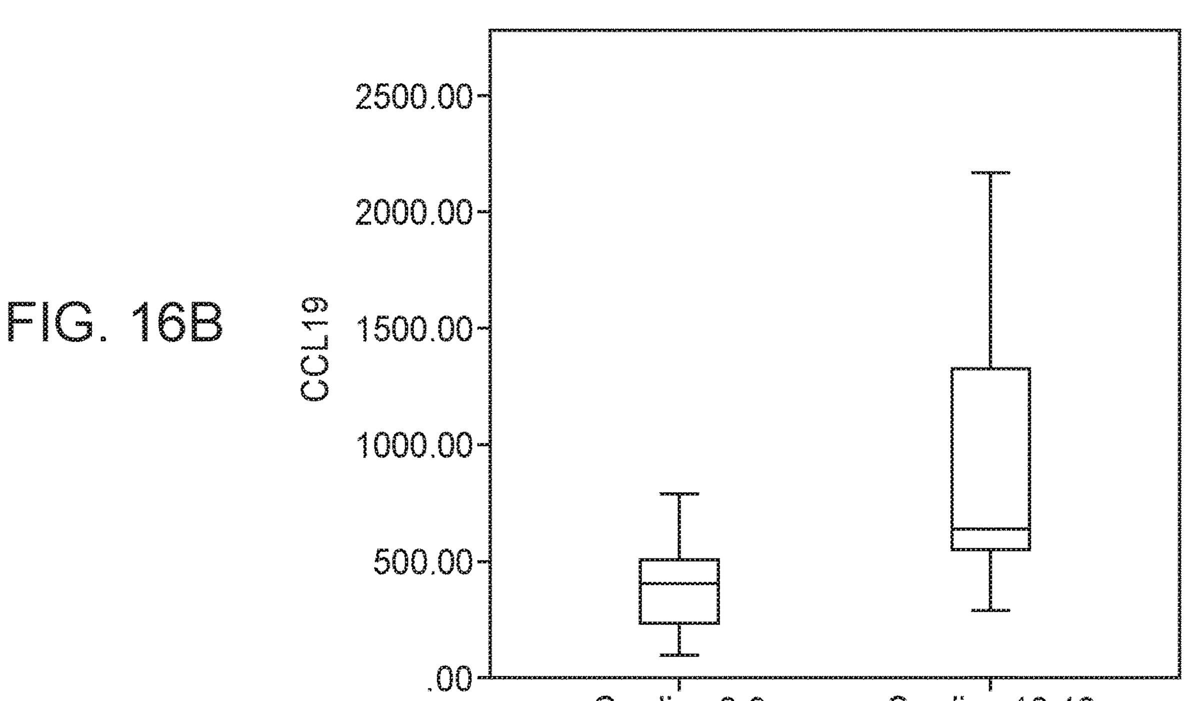

FIGS. 16A and 16B shows that higher level of MIG (FIG. 16A) and CCL19 (FIG. 16B) correlates to a higher Ishak grade.

Figure 17A:
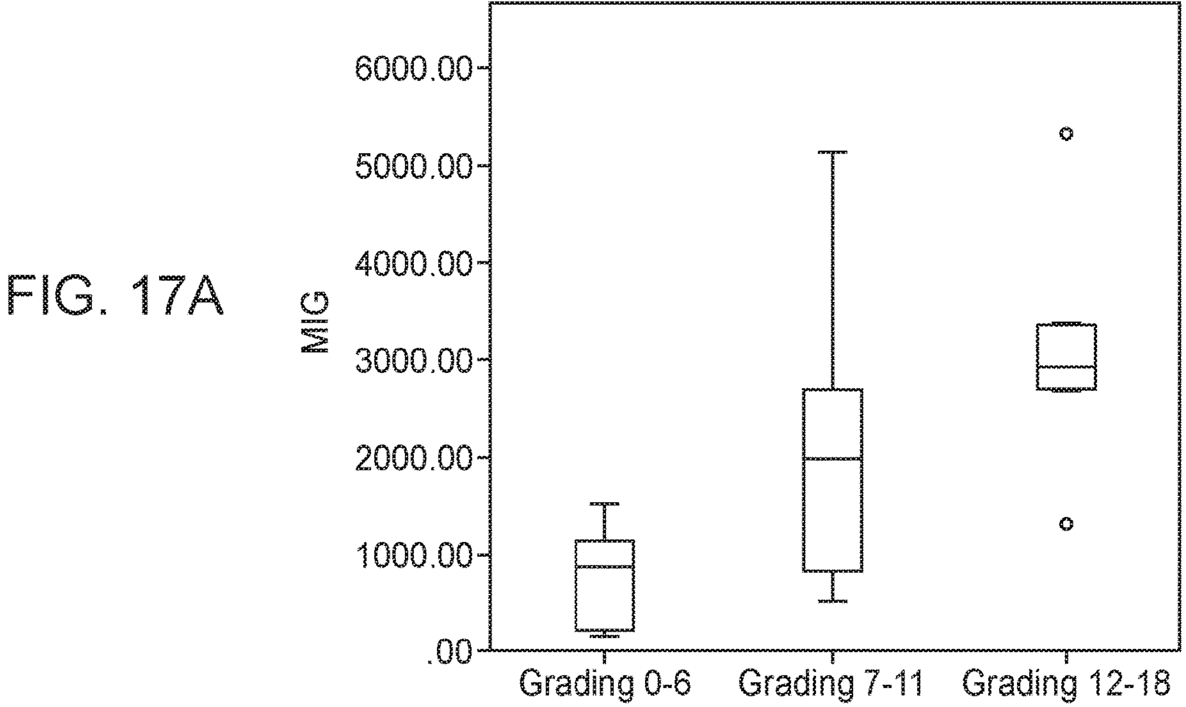
FIGS. 17A-17C. Serum level of MIG, CCL19, and Fractalkine distinguish between Ishak grading 0-6 patients, Ishak grading 7-11 patients and Ishak grading 12-18 patients.
Figure 17B:
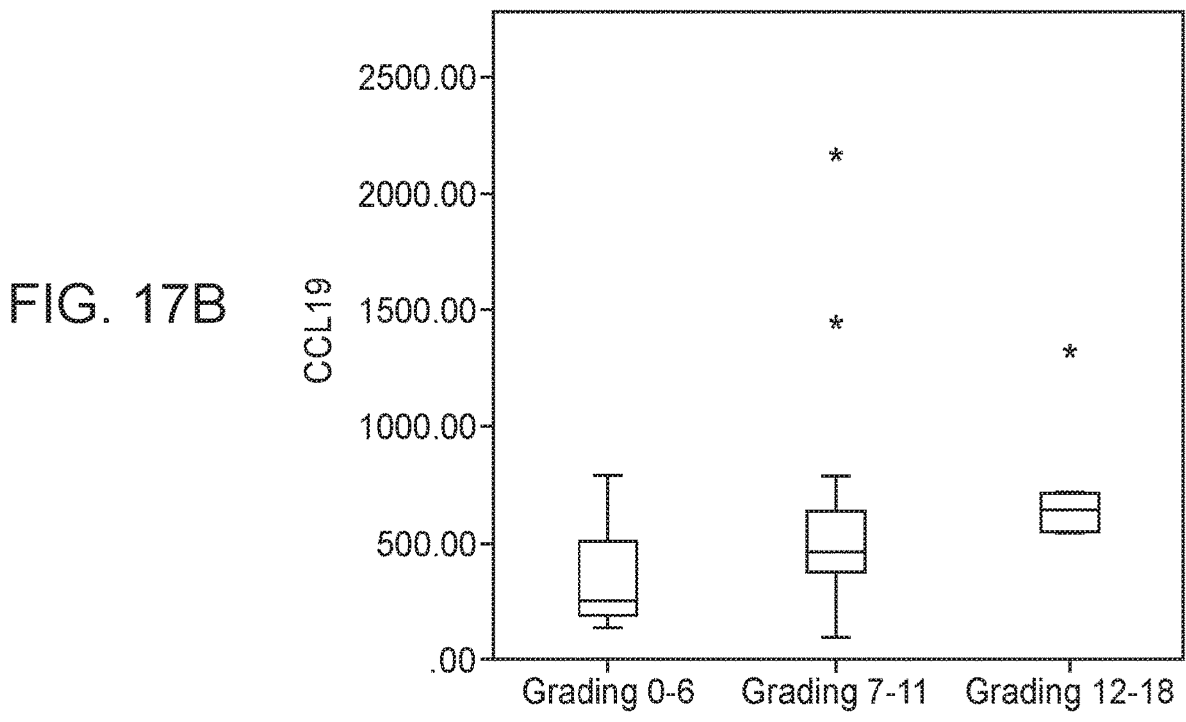
Figure 17C:
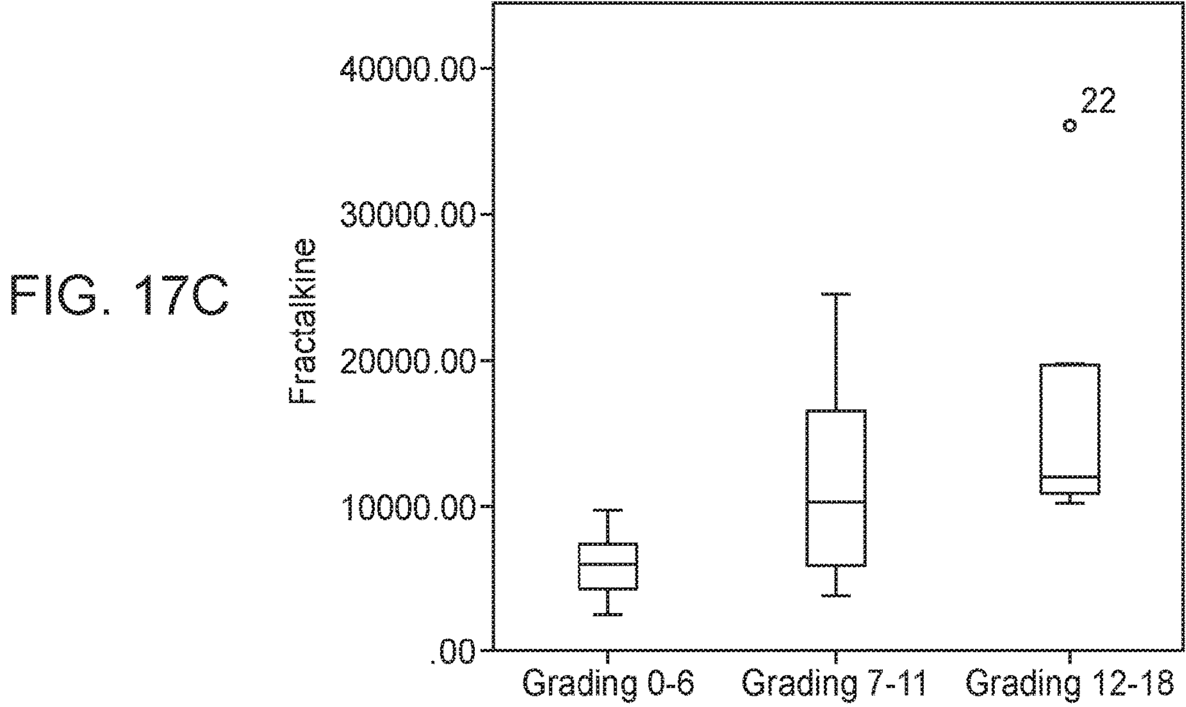

FIGS. 17A-17C show that higher levels of MIG (FIG. 17A), CCL19 (FIG. 17B), and Fractalkine (FIG. 17C) correlate with higher Ishak grade.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

Certain embodiments of the subject disclosure are set out below as separately numbered aspects:

1. A method for treating a subject diagnosed with an autoimmune liver disease (ALD), the method comprising:
administering to a subject an effective amount of an antagonist of CCL19 activity,
wherein the subject is identified as in need for treatment for an autoimmune liver disease (ALD) based on having, in a body fluid sample, a level of CCL19 higher than a threshold level of CCL19.

2. The method of aspect 1, wherein the antagonist of CCL19 activity comprises anti-CCL19 antibody.

3. The method of aspect 1, wherein the antagonist of CCL19 activity comprises an anti-CCR7 antibody.

4. A method for treating a subject diagnosed with an autoimmune liver disease (ALD), the method comprising:
administering to a subject an effective amount of an antagonist of CX3CL1 activity,
wherein the subject is identified as in need for treatment for an autoimmune liver disease (ALD) based on having, in a body fluid sample, a level of CX3CL1 higher than a threshold level of CX3CL1.

5. The method of aspect 4, wherein the antagonist of CX3CL1 activity comprises anti-CX3CL1 antibody.

6. The method of aspect 4, wherein the antagonist of CX3CL1 activity comprises an anti-CX3CR1 antibody.

7. A method for treating a subject diagnosed with an autoimmune liver disease (ALD), the method comprising:
administering to a subject an effective amount of an antagonist of CX3CL1 activity and an antagonist of CCL19 activity,
wherein the subject is identified as in need for treatment for an autoimmune liver disease (ALD) based on having, in a body fluid sample, a level of CCL19 higher than a threshold level of CCL19 and a level of CX3CL1 higher than a threshold level of CX3CL1.

8. The method of aspect 7, wherein the antagonist of CCL19 activity comprises anti-CCL19 antibody or an anti-CCR7 antibody and the antagonist of CX3CL1 comprises anti-CX3CL1 antibody or an anti-CX3CR1 antibody.

9. The method of any one of aspects 1-8, wherein the subject is identified as in need for treatment for an autoimmune liver disease (ALD) based on having, in a body fluid sample, a level of CXCL9 higher than a threshold level of CXCL9.

10. The method of aspect 9, wherein the method further comprises administering an antagonist of CXCL9 activity to the subject.

11. The method of aspect 10, wherein the antagonist of CXCL9 activity comprises anti-CXCL9 antibody or an anti-CXCR3 antibody.

12. The method of any of aspects 1-11, wherein the subject is identified as in need for treatment for an autoimmune liver disease (ALD) based on having, in a body fluid sample, a level of Eotaxin-3 higher than a threshold level of Eotaxin-3.

13. The method of any of aspects 12, wherein the method further comprises administering an antagonist of Eotaxin-3 activity to the subject.

14. The method of aspect 13, wherein the antagonist of Eotaxin-3 activity comprises anti-Eotaxin-3 antibody, an anti-CX3CR1 antibody or an anti-CCR3 antibody.

15. The method of any of aspects 1-14, wherein the ALD comprises autoimmune hepatitis (AIH), primary biliary cholangitis (PBC) or primary sclerosing cholangitis (PSC).

16. The method of any of aspects 1-15, wherein ALD is autoimmune hepatitis (AIH).

17. The method of any of aspects 1-15, wherein ALD is primary biliary cholangitis (PBC).

18. The method of any of aspects 1-15, wherein ALD is primary sclerosing cholangitis (PSC).

19. The method of any one of aspects 1-18, wherein the treating reduces inflammation in liver of the subject.

20. The method of any one of aspects 1-19, wherein the method further comprises administering an immunosuppressant therapy to the subject.

21. The method of aspect 20, wherein the immunosuppressant therapy comprises administering prednisone.

22. The method of aspect 20 or 21, wherein the immunosuppressant therapy comprises administering azathioprine.

23. The method of aspect 17, further comprising administering one or more of ursodeoxycholic acid, obeticholic acid, fenofibrate, bezafibrate, or a derivative thereof to the subject.

24. The method of any of aspects 1-23, wherein the body fluid sample is serum, plasma, or blood.

What is claimed is:

1. A method for treating a subject diagnosed with autoimmune hepatitis (AIH), the method comprising:

identifying a subject as having AIH based on having, in a body fluid sample, a level of CCL19 higher than a threshold level of CCL19 and a level of CX3CL1 higher than a threshold level of CX3CL1; and administering to the subject an effective amount of:

an anti-CCL19 antibody, wherein the anti-CCL19 antibody is an antagonist of CCL19 activity, or an anti-CX3CL1 antibody wherein the anti-CX3CL1 antibody is an antagonist of CX3CL1.

2. The method of claim 1, wherein the subject has in a body fluid sample, a level of Eotaxin-3 higher than a threshold level of Eotaxin-3.

3. The method of claim 1, wherein the treating reduces inflammation in the liver of the subject.

4. The method of claim 1, wherein the method further comprises administering an immunosuppressant therapy to the subject.

5. The method of claim 4, wherein the immunosuppressant therapy comprises administering prednisone and/or azathioprine.

6. The method of claim 1, wherein the body fluid sample is serum, plasma, or blood.

7. The method of claim 1, wherein the body fluid sample is serum.

8. The method of claim 6, wherein the administering comprises administering to the subject an effective amount of the anti-CCL19 antibody.

9. The method of claim 6, wherein the administering comprises administering to the subject an effective amount of the anti-CX3CL1 antibody.

10. The method of claim 7, wherein the administering comprises administering to the subject an effective amount of the anti-CCL19 antibody.

11. The method of claim 7, wherein the administering comprises administering to the subject an effective amount of the anti-CX3CL1 antibody.

* * * * *